US012262951B2

(12) United States Patent
Panescu et al.

(10) Patent No.: US 12,262,951 B2
(45) Date of Patent: Apr. 1, 2025

(54) QUANTITATIVE THREE-DIMENSIONAL VISUALIZATION OF INSTRUMENTS IN A FIELD OF VIEW

(71) Applicant: Intuitive Surgical Operations, Inc., Sunnyvale, CA (US)

(72) Inventors: Dorin Panescu, San Jose, CA (US); Daniel H Jones, Alexandria, VA (US); Christopher B. Allenby, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 176 days.

(21) Appl. No.: 17/671,396

(22) Filed: Feb. 14, 2022

(65) Prior Publication Data

US 2022/0241013 A1    Aug. 4, 2022

Related U.S. Application Data

(63) Continuation of application No. 15/300,258, filed as application No. PCT/US2015/023211 on Mar. 28, 2015, now Pat. No. 11,266,465.

(Continued)

(51) Int. Cl.
*A61B 34/00* (2016.01)
*A61B 34/20* (2016.01)
(Continued)

(52) U.S. Cl.
CPC .............. *A61B 34/00* (2016.02); *A61B 34/20* (2016.02); *A61B 34/30* (2016.02); *A61B 34/35* (2016.02);
(Continued)

(58) Field of Classification Search
CPC ......... A61B 34/00; A61B 34/20; A61B 34/30; A61B 34/35; A61B 1/00; A61B 2034/107; A61B 2034/2065; A61B 2090/364
See application file for complete search history.

(56) References Cited

U.S. PATENT DOCUMENTS 5,394,455 A    2/1995  Roeck et al.
5,631,973 A *  5/1997  Green ................... B25J 9/1689
                                                            382/128
(Continued)

FOREIGN PATENT DOCUMENTS

BR    PI0803388 A2    6/2010
CA    2859998 A1      5/2013
(Continued)

OTHER PUBLICATIONS

Office Action for Chinese Application No. CN202010137786.7, mailed Jun. 22, 2023, 13 pages.
(Continued)

*Primary Examiner* — Anh Tuan T Nguyen
*Assistant Examiner* — Shankar Raj Ghimire
(74) *Attorney, Agent, or Firm* — Foley & Lardner LLP

(57) ABSTRACT

A system is provided that includes a Q3D endoscope disposed to image a field of view and a processor that produces a Q3D model of a scene and identifies target instruments and structures. The processor is configured to display the scene from a virtual field of view of an instrument, to determine a no fly zone around targets, to determine a predicted path for said instruments or to provide 3D tracking of said instruments.

18 Claims, 41 Drawing Sheets

Related U.S. Application Data

(60) Provisional application No. 62/096,509, filed on Dec. 23, 2014, provisional application No. 61/971,749, filed on Mar. 28, 2014.

(51) Int. Cl.
| | | |
|---|---|---|
| *A61B 34/30* | (2016.01) | |
| *A61B 34/35* | (2016.01) | |
| *A61B 34/37* | (2016.01) | |
| *A61B 90/00* | (2016.01) | |
| *A61B 1/00* | (2006.01) | |
| *A61B 17/00* | (2006.01) | |
| *A61B 17/062* | (2006.01) | |
| *A61B 17/072* | (2006.01) | |
| *A61B 34/10* | (2016.01) | |

(52) U.S. Cl.
CPC .............. *A61B 34/37* (2016.02); *A61B 90/37* (2016.02); *A61B 1/00* (2013.01); *A61B 2017/00119* (2013.01); *A61B 17/062* (2013.01); *A61B 17/07207* (2013.01); *A61B 2034/107* (2016.02); *A61B 2034/2065* (2016.02); *A61B 2034/301* (2016.02); *A61B 2090/065* (2016.02); *A61B 2090/364* (2016.02)

(56) References Cited

U.S. PATENT DOCUMENTS

| | | | |
|---|---|---|---|
| 5,704,897 | A | 1/1998 | Truppe |
| 5,735,277 | A | 4/1998 | Schuster |
| 5,749,362 | A | 5/1998 | Funda et al. |
| 5,833,633 | A | 11/1998 | Sarvazyan |
| 6,320,979 | B1 | 11/2001 | Melen |
| 6,346,940 | B1 | 2/2002 | Fukunaga |
| 6,490,475 | B1* | 12/2002 | Seeley ................... A61B 6/547 600/431 |
| 6,491,702 | B2 | 12/2002 | Heilbrun et al. |
| 6,503,195 | B1 | 1/2003 | Keller et al. |
| 6,522,906 | B1 | 2/2003 | Salisbury, Jr. et al. |
| 6,594,552 | B1 | 7/2003 | Nowlin et al. |
| 6,650,927 | B1 | 11/2003 | Keidar |
| 6,932,610 | B2 | 8/2005 | Ono et al. |
| 6,950,550 | B1 | 9/2005 | Sumi et al. |
| 7,728,868 | B2 | 6/2010 | Razzaque et al. |
| 7,907,166 | B2 | 3/2011 | Lamprecht et al. |
| 8,231,522 | B2 | 7/2012 | Endo et al. |
| 8,262,559 | B2 | 9/2012 | Krattiger |
| 8,334,900 | B2 | 12/2012 | Qu et al. |
| 8,514,491 | B2 | 8/2013 | Duparre |
| 8,561,473 | B2 | 10/2013 | Blumenkranz |
| 8,861,089 | B2 | 10/2014 | Duparre |
| 8,866,920 | B2 | 10/2014 | Venkataraman et al. |
| 8,902,321 | B2 | 12/2014 | Venkataraman et al. |
| 9,041,829 | B2 | 5/2015 | Venkataraman et al. |
| 9,060,142 | B2 | 6/2015 | Venkataraman et al. |
| 9,119,552 | B2* | 9/2015 | Baumann ............ G01S 7/4808 |
| 9,188,765 | B2 | 11/2015 | Venkataraman et al. |
| 9,235,898 | B2 | 1/2016 | Venkataraman et al. |
| 9,264,610 | B2 | 2/2016 | Duparre |
| 9,485,496 | B2 | 11/2016 | Venkataraman et al. |
| 10,052,157 | B2 | 8/2018 | Frimer et al. |
| 10,334,227 | B2 | 6/2019 | Panescu et al. |
| 10,350,009 | B2 | 7/2019 | Panescu et al. |
| 10,368,054 | B2 | 7/2019 | Panescu et al. |
| 10,555,788 | B2 | 2/2020 | Panescu et al. |
| 11,266,465 | B2 | 3/2022 | Panescu et al. |
| 11,304,771 | B2 | 4/2022 | Panescu et al. |
| 2001/0051761 | A1 | 12/2001 | Khadem |
| 2002/0022765 | A1 | 2/2002 | Belson |
| 2002/0049375 | A1 | 4/2002 | Strommer et al. |
| 2002/0054208 | A1 | 5/2002 | Goldstein et al. |
| 2003/0036714 | A1 | 2/2003 | Kuth |
| 2003/0158477 | A1 | 8/2003 | Panescu |
| 2003/0181800 | A1 | 9/2003 | Bonutti |
| 2003/0220541 | A1 | 11/2003 | Salisbury et al. |
| 2004/0138556 | A1* | 7/2004 | Cosman ................... G06T 3/00 600/473 |
| 2005/0018888 | A1* | 1/2005 | Zonneveld .............. A61B 6/00 382/128 |
| 2005/0151839 | A1* | 7/2005 | Ito ........................... G06T 15/04 348/42 |
| 2005/0182295 | A1 | 8/2005 | Soper et al. |
| 2005/0219205 | A1 | 10/2005 | Bailey et al. |
| 2005/0254720 | A1 | 11/2005 | Tan et al. |
| 2006/0183992 | A1* | 8/2006 | Kawashima ............ A61B 8/12 600/478 |
| 2006/0281971 | A1 | 12/2006 | Sauer et al. |
| 2007/0055128 | A1* | 3/2007 | Glossop ................. A61B 1/018 600/407 |
| 2007/0060792 | A1 | 3/2007 | Draxinger et al. |
| 2007/0083098 | A1 | 4/2007 | Stern et al. |
| 2007/0135803 | A1* | 6/2007 | Belson ............... A61B 1/00154 606/1 |
| 2007/0147707 | A1 | 6/2007 | Coste-Maniere et al. |
| 2007/0151391 | A1* | 7/2007 | Larkin ................... A61B 34/76 74/490.06 |
| 2007/0171369 | A1 | 7/2007 | Grundig |
| 2007/0236514 | A1 | 10/2007 | Agusanto et al. |
| 2007/0265527 | A1* | 11/2007 | Wohlgemuth ......... A61B 90/36 606/131 |
| 2007/0276501 | A1 | 11/2007 | Betz et al. |
| 2008/0004603 | A1 | 1/2008 | Larkin et al. |
| 2008/0009674 | A1* | 1/2008 | Yaron .................... A61B 90/36 600/117 |
| 2008/0058593 | A1 | 3/2008 | Gu et al. |
| 2008/0071140 | A1* | 3/2008 | Gattani ................. A61B 34/20 600/117 |
| 2008/0188716 | A1 | 8/2008 | Heckele et al. |
| 2008/0207997 | A1 | 8/2008 | Higgins et al. |
| 2009/0010519 | A1* | 1/2009 | Wakai .................... G16H 30/20 382/131 |
| 2009/0043161 | A1 | 2/2009 | Doi |
| 2009/0054910 | A1 | 2/2009 | Zheng et al. |
| 2009/0076476 | A1 | 3/2009 | Barbagli et al. |
| 2009/0088634 | A1* | 4/2009 | Zhao ................... A61B 1/00193 600/425 |
| 2009/0088897 | A1 | 4/2009 | Zhao et al. |
| 2009/0133260 | A1 | 5/2009 | Durbin et al. |
| 2009/0157059 | A1 | 6/2009 | Allen et al. |
| 2009/0189749 | A1 | 7/2009 | Salada et al. |
| 2009/0192524 | A1 | 7/2009 | Itkowitz et al. |
| 2009/0221908 | A1 | 9/2009 | Glossop et al. |
| 2009/0259102 | A1 | 10/2009 | Koninckx et al. |
| 2009/0306474 | A1 | 12/2009 | Wilson |
| 2009/0317727 | A1 | 12/2009 | Beck |
| 2009/0324009 | A1* | 12/2009 | Schulz ..................... G06T 7/73 382/103 |
| 2010/0111389 | A1 | 5/2010 | Strobel et al. |
| 2010/0149183 | A1* | 6/2010 | Loewke .................. G06V 20/693 345/424 |
| 2010/0169815 | A1 | 7/2010 | Zhao et al. |
| 2010/0249506 | A1 | 9/2010 | Prisco |
| 2010/0274087 | A1 | 10/2010 | Diolaiti et al. |
| 2010/0281370 | A1 | 11/2010 | Rohaly et al. |
| 2010/0312096 | A1 | 12/2010 | Guttman et al. |
| 2010/0312129 | A1 | 12/2010 | Schecter et al. |
| 2011/0032088 | A1 | 2/2011 | Kim et al. |
| 2011/0044521 | A1 | 2/2011 | Tewfik et al. |
| 2011/0122229 | A1 | 5/2011 | Cinquin et al. |
| 2011/0163946 | A1 | 7/2011 | Tartz et al. |
| 2011/0193938 | A1 | 8/2011 | Oderwald et al. |
| 2011/0234780 | A1* | 9/2011 | Ito ............................ A61B 1/05 348/E7.085 |
| 2011/0282143 | A1 | 11/2011 | Matsumoto |
| 2011/0282151 | A1 | 11/2011 | Trovato et al. |
| 2012/0041345 | A1 | 2/2012 | Rajamani et al. |
| 2012/0063644 | A1 | 3/2012 | Popovic et al. |
| 2012/0101370 | A1 | 4/2012 | Razzaque et al. |
| 2012/0139828 | A1 | 6/2012 | Lok et al. |
| 2012/0155731 | A1 | 6/2012 | Weersink et al. |
| 2012/0182294 | A1 | 7/2012 | Cordon Garcia et al. |

(56) References Cited

U.S. PATENT DOCUMENTS

| | | | |
|---|---|---|---|
| 2012/0190923 A1 | 7/2012 | Kunz et al. | |
| 2012/0265062 A1 | 10/2012 | Sliwa et al. | |
| 2012/0289777 A1 | 11/2012 | Chopra et al. | |
| 2012/0327186 A1* | 12/2012 | Kitamura | A61B 5/064 348/45 |
| 2013/0018255 A1* | 1/2013 | Kitamura | G06T 19/003 600/424 |
| 2013/0023730 A1* | 1/2013 | Kitamura | A61B 1/3132 600/104 |
| 2013/0035583 A1 | 2/2013 | Park et al. | |
| 2013/0038689 A1 | 2/2013 | McDowall | |
| 2013/0070060 A1 | 3/2013 | Chatterjee et al. | |
| 2013/0079620 A1 | 3/2013 | Kuth et al. | |
| 2013/0085329 A1 | 4/2013 | Morrissette et al. | |
| 2013/0197357 A1 | 8/2013 | Green et al. | |
| 2013/0202676 A1 | 8/2013 | Koob et al. | |
| 2013/0211244 A1 | 8/2013 | Nathaniel et al. | |
| 2013/0211418 A1 | 8/2013 | Lim et al. | |
| 2013/0230837 A1 | 9/2013 | Meglan et al. | |
| 2013/0250081 A1 | 9/2013 | Pandey | |
| 2013/0296872 A1 | 11/2013 | Davison et al. | |
| 2013/0321262 A1 | 12/2013 | Schecter et al. | |
| 2013/0345718 A1* | 12/2013 | Crawford | A61B 17/8866 606/130 |
| 2014/0005684 A1 | 1/2014 | Kim et al. | |
| 2014/0039527 A1 | 2/2014 | Avelar et al. | |
| 2014/0071239 A1 | 3/2014 | Yokota et al. | |
| 2014/0142422 A1* | 5/2014 | Manzke | A61B 8/12 600/424 |
| 2014/0147729 A1 | 5/2014 | Moon et al. | |
| 2014/0163359 A1 | 6/2014 | Sholev et al. | |
| 2014/0194896 A1 | 7/2014 | Frimer et al. | |
| 2014/0253684 A1 | 9/2014 | Kumar et al. | |
| 2014/0276093 A1 | 9/2014 | Zeien et al. | |
| 2014/0336501 A1* | 11/2014 | Masumoto | A61B 1/31 600/417 |
| 2015/0011894 A1 | 1/2015 | Sarrafzadeh et al. | |
| 2015/0025316 A1 | 1/2015 | Hasegawa et al. | |
| 2015/0031990 A1* | 1/2015 | Boctor | A61B 8/483 600/440 |
| 2015/0049167 A1 | 2/2015 | Suzuki et al. | |
| 2015/0062299 A1 | 3/2015 | Brown et al. | |
| 2015/0112237 A1 | 4/2015 | Amedi et al. | |
| 2015/0134095 A1 | 5/2015 | Hemani et al. | |
| 2015/0185849 A1 | 7/2015 | Levesque et al. | |
| 2015/0209003 A1 | 7/2015 | Halmann et al. | |
| 2015/0230697 A1 | 8/2015 | Phee et al. | |
| 2015/0230869 A1 | 8/2015 | Shim et al. | |
| 2015/0238276 A1* | 8/2015 | Atarot | A61B 1/00064 606/130 |
| 2015/0271483 A1 | 9/2015 | Sun et al. | |
| 2015/0374210 A1 | 12/2015 | Durr et al. | |
| 2016/0151646 A1 | 6/2016 | Bonutti et al. | |
| 2016/0183841 A1* | 6/2016 | Duindam | A61B 34/25 |
| 2017/0172382 A1* | 6/2017 | Nir | A61B 18/22 |
| 2017/0172662 A1 | 6/2017 | Panescu et al. | |
| 2017/0181809 A1 | 6/2017 | Panescu et al. | |
| 2017/0212723 A1 | 7/2017 | Atarot et al. | |
| 2018/0303558 A1* | 10/2018 | Thomas | A61B 34/20 |
| 2019/0167354 A1 | 6/2019 | Heaney et al. | |
| 2019/0374130 A1* | 12/2019 | Bydlon | A61B 10/04 |
| 2020/0022769 A1 | 1/2020 | Panescu et al. | |
| 2022/0020219 A1* | 1/2022 | Chav | G06F 3/017 |
| 2022/0241013 A1* | 8/2022 | Panescu | A61B 34/00 |
| 2023/0260427 A1* | 8/2023 | Driscoll | G09B 23/286 |

FOREIGN PATENT DOCUMENTS

| | | | |
|---|---|---|---|
| CN | 1788684 A | 6/2006 | |
| CN | 1874734 A | 12/2006 | |
| CN | 100998511 A | 7/2007 | |
| CN | 101053517 A | 10/2007 | |
| CN | 101065052 A | 10/2007 | |
| CN | 101090670 A | 12/2007 | |
| CN | 102046065 A | 5/2011 | |
| CN | 102595998 A | 7/2012 | |
| CN | 102625670 A | 8/2012 | |
| CN | 102636130 A | 8/2012 | |
| CN | 102711650 A | 10/2012 | |
| CN | 102781303 A | 11/2012 | |
| CN | 102811655 A | 12/2012 | |
| CN | 102908158 A | 2/2013 | |
| CN | 102933163 A | 2/2013 | |
| CN | 103108602 A | 5/2013 | |
| CN | 103269430 A | 8/2013 | |
| CN | 103315696 A | 9/2013 | |
| CN | 103356155 A | 10/2013 | |
| CN | 103596521 A | 2/2014 | |
| EP | 1382297 A1 | 1/2004 | |
| EP | 1577010 A2 | 9/2005 | |
| EP | 1710828 A2 | 10/2006 | |
| EP | 1826726 A1 | 8/2007 | |
| EP | 2043499 A1 | 4/2009 | |
| EP | 2245982 A1 | 11/2010 | |
| EP | 2444006 A2 | 4/2012 | |
| EP | 2548495 A1 | 1/2013 | |
| EP | 2641561 A1 | 9/2013 | |
| JP | S6160087 A | 3/1986 | |
| JP | H04176429 A | 6/1992 | |
| JP | H04325147 A | 11/1992 | |
| JP | H0630896 A | 2/1994 | |
| JP | H06160087 A | 6/1994 | |
| JP | H07240945 A | 9/1995 | |
| JP | H0998985 A | 4/1997 | |
| JP | H11309 A | 1/1999 | |
| JP | 2000065532 A | 3/2000 | |
| JP | 2000149017 A | 5/2000 | |
| JP | 2002027502 A | 1/2002 | |
| JP | 2002171537 A | 6/2002 | |
| JP | 2003235785 A | 8/2003 | |
| JP | 2005087468 A | 4/2005 | |
| JP | 2005091265 A | 4/2005 | |
| JP | 2006109939 A | 4/2006 | |
| JP | 2006305332 A | 11/2006 | |
| JP | 2009204991 A | 9/2009 | |
| JP | 2010085240 A | 4/2010 | |
| JP | 2011200515 A | 10/2011 | |
| JP | 2011253300 A * | 12/2011 | |
| JP | 2012518517 A | 8/2012 | |
| JP | 2013515959 A | 5/2013 | |
| JP | 2014000118 A | 1/2014 | |
| KR | 20020014751 A | 2/2002 | |
| KR | 20130015146 A | 2/2013 | |
| WO | WO-2006080076 A1 | 8/2006 | |
| WO | WO-2007047782 A2 | 4/2007 | |
| WO | WO-2007111955 A2 * | 10/2007 | A61B 34/20 |
| WO | WO-2010122145 A1 | 10/2010 | |
| WO | WO-2010147729 A1 | 12/2010 | |
| WO | WO-2012059253 A1 | 5/2012 | |
| WO | WO-2012136223 A1 | 10/2012 | |
| WO | WO-2012155152-41 | 11/2012 | |
| WO | WO-2013027201 A2 | 2/2013 | |
| WO | WO-2013038403 A2 | 3/2013 | |
| WO | WO-2013073061 A1 | 5/2013 | |
| WO | WO-2013134782 A1 | 9/2013 | |
| WO | WO-2013156893 A1 * | 10/2013 | A61B 1/00009 |
| WO | WO-2014002849 A1 | 1/2014 | |

OTHER PUBLICATIONS

Office Action for Chinese Application No. CN202010137786, mailed Oct. 17, 2022, 17 pages.

Agus M., et al., "Real-time Cataract Surgery Simulation for Training," In Eurographics Italian Chapter Conference, Eurographics Association, 2006, 5 pages.

Coelho M., et al., "Shape-Changing Interfaces," Personal and Ubiquitous Computing, M. Coelho, et al., MIT Media Lab, 75 Amherst St., E14-548H, Cambridge, MA, USA, Springer-Verlag, published online Jul. 29, 2010, vol. 15 (2), pp. 161-173.

Cotin S., et al., "Real-time Elastic Deformations of Soft Tissues for Surgery Simulation," IEEE Transactions on Visualization and Computer Graphics, 1999, vol. 5, pp. 62-73.

(56) References Cited

OTHER PUBLICATIONS

Culijat M., et al., "Pneumatic Balloon Actuators for Tactile Feedback in Robotic Surgery," Industrial Robot: An International Journal, 2008, vol. 35 (5), pp. 449-455.
Delingette H., "Simplex Meshes: A General Representation for 3D Shape Reconstruction," Technical Report 2214, INRIA, Mar. 1994, 59 pages.
Eltaib, M.E.H., et al., "Tactile Sensing Technology for Minimal Access Surgery—a Review." Mechatronics, Pergamon Press, Oxford, GB, vol. 13(10), Dec. 1, 2003 (Dec. 1, 2003), pp. 1163-1177, XP004448741, DOI: 10.1016/S0957-4158(03)00048-5.
Extended European Search Report for Application No. 15769234.4, mailed on Oct. 17, 2017, 11 pages (ISRG05865/EP).
Extended European Search Report for Application No. EP15767964.8, mailed on Apr. 24, 2018, 19 pages (ISRG05863/EP).
Extended European Search Report for Application No. EP15768409.3, mailed on Feb. 26, 2018, 9 pages (ISRG05860/EP).
Extended European Search Report for Application No. EP15769289.8, mailed on Dec. 12, 2017, 11 pages (ISRG05862/EP).
Extended European Search Report for Application No. EP15770100.4, mailed on Feb. 16, 2018. 14 pages (ISRG05861/EP).
Extended European Search Report for Application No. EP15770259.8, mailed on Feb. 21, 2018, 18 pages (ISRG05864/EP).
Follmer S., et al., "inFORM: Dynamic Physical Affordances and Constraints through Shape and Object Actuation," Proceedings of the 26th Annual ACM Symposium on UIST, ACM, 2013,New York, NY, USA, vol. 13, pp. 417-426.
Garcia O., et al., "Real-time 3D Modeling from Endoscope Image Sequences," ICRA 2009 Workshop—Advanced Sensing and Sensor Integration in Medical Robotics, May 13, 2009 (May 13, 2009), Retrieved from the Internet: URL: http://webdiis.unizar.es/~jcivera/papers/garcia_etal_icra09.pdf [retrieved on Oct. 5, 2017], 3 pages, XP055412801.
Hassanfiroozi A., et al., Liquid Crystal Lens Array for 3D Endoscope Application, in: Three-Dimensional Imaging, Visualization, and Display, Javidi B., et al., eds., Proceedings of SPIE, vol. 9117 91170E 1-7, 7 pages, [online], [retrieved Aug. 21, 2014]. Retrieved from the Internet: URL: http://proceedings.spiedigitallibrary.org/.
Howe, Robert D. et al., "Remote Palpation Technology," IEEE Engineering in Medicine and Biology, 1995, pp. 318-323, vol. 14—Issue 3, IEEE.
International Preliminary Report on Patentability for Application No. PCT/US2015/023210, mailed on Oct. 13, 2016, 12 pages (ISRG0580/PCT).
International Preliminary Report on Patentability for Application No. PCT/US2015/023211, mailed on Oct. 13, 2016, 10 pages (ISRG05861/PCT).
International Preliminary Report on Patentability for Application No. PCT/US2015/023212, mailed on Oct. 13, 2016, 7 pages (ISRG05862/PCT).
International Preliminary Report on Patentability for Application No. PCT/US2015/023213, mailed on Oct. 13, 2016, 11 pages (ISRG05863/PCT).
International Preliminary Report on Patentability for Application No. PCT/US2015/023214, mailed on Oct. 13, 2016, 7 pages (ISRG05864/PCT).
International Preliminary Report on Patentability for Application No. PCT/US2015/023217, mailed on Oct. 13, 2016, 08 pages (ISRG05865/PCT).
International Search Report and Written Opinion for Application No. PCT/US15/23210, mailed on Jun. 29, 2015, 17 pages (ISRG05860/PCT).
International Search Report and Written Opinion for Application No. PCT/US15/23211, mailed on Jul. 1, 2015, 13 pages (ISRG05861/PCT).
International Search Report and Written Opinion for Application No. PCT/US15/23217, mailed on Jun. 29, 2015, 12 pages (ISRG05865/PCT).
International Search Report and Written Opinion for Application No. PCT/US2015/023214, mailed on Jun. 29, 2015, 10 pages (ISRG05864/PCT).
International Search Report and Written Opinion for Application No. PCT/US2015/23212. mailed on Jun. 30, 2015, 8 pages (ISRG05862/PCT).
International Search Report and Written Opinion for Application No. PCT/US2015/23213, mailed on Jul. 14, 2015, 13 pages (ISRG05863/PCT).
Iwata H., et al., "Project FEELEX: Adding Haptic Surface to Graphics," SIGGRAPH'01, 2001, pp. 469-476.
J. Montagnat and H. Delingette, "Volumetric Medical Images Segmentation Using Shape Constrained Deformable Models," Proceedings of CVRMed-MRCAS '97, Grenoble, France,J. Troccaz, E. Grimson, and R. Mosges, eds. Mar. 1997, pp. 13-22.
K. Chinzei and K. Miller, "Compression of Swine Brain Tissue; Experiment in Vitro," Journel of Mechanical Engineering Laboratory, Jul. 1996, vol. 50(4), pp. 106-115.
Kaczmarek K.A. et al., "Maximal Dynamic Range Electrotactile Stimulation Waveforms," IEEE Transactions on Biomedical Engineering, Jul. 1999, vol. 39 (7), pp. 701-715.
Killebrew J.H., et al., "A Dense Array Stimulator to Generate Arbitrary Spatia-Temporal Tactile Stimuli," Journal of Neuroscience Methods, 2007, vol. 161 (1), pp. 62-74.
Laks Raghupathi, Laurent Grisoni, Fran?ois Faure, Damien Marchal, Marie-Paule Cani, Christophe Chaillou, "An Intestinal Surgery Simulator: Real-Time Collision Processing and Visualization," IEEE Transactions on Visualization and Computer Graphics, vol. 10, No. 6, pp. 708-718, Nov./Dec. 2004.
Monserrat C., et al., "GeRTISS: A Generic Multi-model Surgery Simulator," Springer-Verlag Berlin Heidelberg, IS4TM 2003, LNCS 2673, 2003, pp. 59-66.
Moore M., et al., "Collision Detection and Response for Computer Animation," Computer Graphics, SIGGRAPH, 1988, vol. 22 (4), pp. 289-298.
Moy G., et al., "A Compliant Tactile Display for Teletaction." Proceedings of ICRA in Robotics and Automation, 2000, IEEE, vol. 4, 7 pages.
Office Action mailed Sep. 1, 2017 for Chinese Application No. 201580024436.7 filed Mar. 28, 2015, 25 pages (ISRG05862/CN).
Office Action mailed Jul. 4, 2018 for Chinese Application No. 201580024439.0 filed Mar. 28, 2015, 13 pages (ISRG05865/CN).
Okamura A.M., "Haptic Feedback in Robot-Assisted Minimally Invasive Surgery," Current Opinion in Urology, 2009, vol. 19 (1), pp. 102-107.
Oosten J.V., "Understanding the View Matrix—3D Game Engine Programming 3D Game Engine Programming," Jul. 6, 2011 (Jul. 6, 2017), Retrieved from the Internet: URL: http://www.3dgep.com/understading-the-view-matrix/ [retrieved on Oct. 14, 2015], 34 pages, XP055220667.
Ottermo M.V., et al., "Electromechanical Design of a Miniature Tactile Shape Display for Minimally Invasive Surgery," Proceedings of the First Joint Eurohaptics Conference and Symposium on Haptic Interfaces for Virtual Environment and Teleoperator Systems, IEEE, 2005, 2 pages.
Partial Supplementary European Search Report for Application No. 15767964.8, mailed on Dec. 13, 2017, 17 pages (ISRG05863/EP).
Partial Supplementary European Search Report for Application No. 15770100.4, mailed on Oct. 18, 2017, 17 pages (ISRG05861/EP).
Partial Supplementary European Search Report for Application No. EP15770259.8, mailed on Oct. 24, 2017, 20 pages (ISRG05864/EP).
Rasmussen M.K., et al., "Shape-Changing Interfaces: A Review of the Design Space and Open Research Questions," Proceedings of the SIGCHI Conference on Human Factors in Computing Systems on CHI, ACM, 2012, pp. 735-744.
Reiley, Carol E. et al., "Effects of visual force feedback on robot-assisted surgical task performance," Journal of Thoracic and Cardiovascular Surgery, Jan. 2008, vol. 35 (1), pp. 196-202.
Rigel, D. S., et al., "The Evolution of Melanoma Diagnosis: 25 Years Beyond the ABCDs," CA Cancer J Clin, vol. 60 (5), Jul. 29, 2010 (Jul. 29, 2010), pp. 301-316, XP055384411, ISSN: 0007-9235, DOI: 10.3322/caac.20074.

(56) References Cited

OTHER PUBLICATIONS

Schick, A et al., "3D Measuring in the Field of Endoscopy," Proceedings of the SPIE, vol. 8082, 2011, pp. 1-12.
Schmalz, C. et al., "An Endoscopic 3D Scanner Based on Structured Light," Medical Image Analysis, vol. 16 (5) Jul. 2012, pp. 1063-1072.
Thormahlen T., et al., "Three-Dimensional Endoscopy," Falk Symposium, vol. 124, Jan. 1, 2002 (Jan. 1, 2002), 6 pages, XP055413139, ISBN: 978-0-7923-8774-9.
Vertut. J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
Wu C., "3D Reconstruction of Anatomical Structures from Endoscopic Images," CMU-R1-TR-10-04, Jan. 1, 2010 (Jan. 1, 2010), Retrieved from the Internet: URL:https://www.cs.cmu.edu/-ILIM/publications/PDFs/W-THESIS09.pdf [retrieved on Oct. 5, 2017], pp. 1-113, XP055412730.

\* cited by examiner

QUANTITATIVE THREE-DIMENSIONAL VISUALIZATION OF INSTRUMENTS IN A FIELD OF VIEW

RELATED APPLICATIONS

This application is a continuation of and claims the benefit of priority under 35 U.S.C. § 120 to U.S. patent application Ser. No. 15/300,258, filed on Sep. 28, 2016, which is a U.S. National Stage Filing under 35 U.S.C. 371 from International Application No. PCT/US2015/023211, filed on Mar. 28, 2015, and published as WO 2015/149041 A1 on Oct. 1, 2015, which claims the benefit of priority to U.S. provisional patent application No. 61/971,749, filed on Mar. 28, 2014, and entitled "QUANTITATIVE THREE-DIMENSIONAL IMAGING OF SURGICAL SCENES"; and to U.S. provisional patent application No. 62/096,509, filed on Dec. 23, 2014, and entitled "QUANTITATIVE THREE-DIMENSIONAL VISUALIZATION OF INSTRUMENTS IN A field of view"; each of which is incorporated herein by reference in its entirety.

FIELD

The invention relates in general to surgical endoscopy systems having associated image sensors, and more particularly, to determining three-dimensional coordinates of physical structures displayed in surgical images.

BACKGROUND

Quantitative three-dimensional (Q3D) vision provides numerical information about the actual physical (x, y, z) 3D coordinates of target points in a real world scene. With quantitative 3D vision, a person not only can obtain a three-dimensional perception of a real world scene, but also can obtain numerical information about physical dimensions of objects in the scene and physical distances between objects in the scene. In the past, some Q3D systems have been proposed that use time-of-flight related information or phase information to determine 3D information about a scene. Other Q3D systems have used structured light to determine 3D information about a scene.

The use of time-of-flight information is disclosed in U.S. Pat. No. 6,323,942, entitled "CMOS-compatible three-dimensional image sensor IC", which discloses a three-dimensional imaging system that includes a two-dimensional array of pixel light sensing detectors fabricated on a common IC using CMOS fabrication techniques. Each detector has an associated high speed counter that accumulates clock pulses in number directly proportional to time-of-flight (TOF) for a system-emitted pulse to reflect from an object point and be detected by a pixel detector focused upon that point. The TOF data provides a direct digital measure of distance from the particular pixel to a point on the object reflecting the emitted light pulse. In a second embodiment, the counters and high speed clock circuits are eliminated, and instead each pixel detector is provided with a charge accumulator and an electronic shutter. The shutters are opened when a light pulse is emitted and closed thereafter such that each pixel detector accumulates charge as a function of return photon energy falling upon the associated pixel detector. The amount of accumulated charge provides a direct measure of round-trip TOF.

The use of time delay information is disclosed in U.S. Pat. No. 8,262,559, entitled, "Apparatus and method for endoscopic 3D data collection", which discloses a modulated measuring beam and a light-transmitting mechanism for conducting the measuring beam onto an area to be observed, where the light-transmitting mechanism includes an illuminating lens, in addition to a light-imaging mechanism for imaging a signal beam from the area to be observed at least onto a phase-sensitive image sensor. Time delays, which may correspond to differences in depth in the millimeter range, result in phase information that makes possible the production of an image that depicts depth and distance information.

The use of structured light to determine physical coordinates of objects in a visual image is disclosed in U.S. Pat. App. Pub. No. 2012/0190923, entitled "Endoscope"; and in C. Schmalz, et al., "An endoscopic 3D scanner based on structured light", Medical Image Analysis, 16 (2012) 1063-1072. A triangulation method is used to measure the topography of a surface. Structured light in the form of projection rays, which may have a range of different color spectra, are incident upon and are reflected from a surface. The reflected rays are observed by a camera that is calibrated to use the reflected color spectra information to determine 3D coordinates of the surface. More specifically, the use of structured light typically involves shining a light pattern on a 3D surface, and determining physical distances based upon a deformation pattern of the light due to contours of the physical object.

An imager array camera has been built that includes a plurality of pixel arrays that can be used to compute scene depth information for pixels in the array. High resolution (HR) images are generated from multiple low resolution (LR) images. A reference viewpoint is selected and an HR image is generated as seen by that viewpoint. A parallax processing technique utilizes the effects of aliasing to determine pixel correspondences for non-reference images with respect to the reference image pixels. Fusion and superresolution are utilized to produce the HR image from the multiple LR images. See e.g., U.S. Pat. No. 8,514,491, entitled "Capturing and Processing Images using Monolithic Camera Array with Heterogeneous Imager"; U.S. Pat. App. Pub. No. 2013/0070060, entitled, "Systems and Methods for Determining Depth from multiple Views of a Scene that Include Aliasing using Hypothesized Fusion"; and K. Venkataramnan et al., "PiCam: An ultra-Thin high Performance Monolithic Camera Array".

FIG. 1 is an illustrative drawing showing details of a known imager sensor 180 in accordance with some embodiments. The image sensor 180 includes an arrangement of sensors 184. Each sensor in the arrangement includes a two dimensional arrangement of pixels having at least two pixels in each dimension. Each sensor includes a lens stack 186. Each lens stack 186 has a corresponding focal plane 188. Each lens stack 186 creates a separate optical channel that resolves an image onto a corresponding arrangement of pixels disposed in its corresponding focal 188 plane. The pixels act as light sensors, and each focal plane 188 with its multiple pixels acts as an image sensor. Each sensor with its focal plane 188 occupies a region of the sensor arrangement different from regions of the sensor arrangement occupied by other sensors and focal planes.

FIG. 2 is an illustrative drawing showing a simplified plan view of the known arrangement of sensors 184 of FIG. 1 that includes sensors labeled as sensors $S_{11}$ through $S_{33}$. The imager sensor arrangement 184 is fabricated on a semiconductor chip to include a plurality of sensors $S_{11}$ through $S_{33}$. Each of the sensors $S_{11}$ through $S_{33}$ includes a plurality of pixels (e.g., 0.32 megapixels) and is coupled to peripheral circuitry (not shown) that includes independent read-out control and pixel digitization. In some embodiments, the sensors $S_{11}$ through $S_{33}$ are arranged into a grid format as illustrated in FIG. 2. In other embodiments, the sensors are arranged in a non-grid format. For example, the sensors may be arranged in a circular pattern, zigzagged pattern, scattered pattern, or irregular pattern including sub-pixel offsets.

Each individual pixel of the sensors 184 of FIGS. 1-2 includes a microlens pixel stack. FIG. 3 is an illustrative drawing of a known microlens pixel stack of the sensors of FIGS. 1-2. The pixel stack 800 includes a microlens 802, which is positioned above an oxide layer 804. Typically beneath the oxide layer 804 there may be a color filter 806, which is disposed above a nitride layer 808, which is disposed above a second oxide layer 810, which sits atop a silicon layer 812 that includes the active area 814 (typically a photodiode) of the individual pixel. The primary role of the microlens 802 is to gather the light incident on its surface and to focus that light onto the small active area 814. The pixel aperture 816 is determined by the spread of the microlens.

Additional information concerning the above-described known imager sensor arrangement architecture is provided in U.S. Pat. No. 8,514,491 B2 (filed Nov. 22, 2010), and in U.S. Patent Application Pub. No. US 2013/0070060 A1 (filed Sep. 19, 2012).

SUMMARY

In one aspect, a system determines a Q3D model of the scene imaged by a Q3D sensor of an endoscope. 3D coordinates are determined for a target instrument within the Q3D model. A geometrical transformation of the endoscope pose is determined to align it with the pose of the identified target instrument. Based on this geometrical transformation, the Q3D model of an anatomical structure is transformed so that to provide an observer with a virtual view according to the pose of the target instrument.

In another aspect, a Q3D system determines a "no fly zone" adjacent to at least one target within a Q3D model. A determination is made as to whether the "no fly zone" is violated based at least in part upon whether a closest distance between the first target and a second target is less than a threshold distance. An output signal is provided in response to a determination that the closest distance between the first and second targets is less than the threshold distance. Said targets may be an instrument, a structure or an anatomic organ.

In another aspect, a Q3D system identifies an instrument within an imaged scene. A predicted path of the identified instrument is determined based at least in part upon extrapolation from a previous path followed by the identified instrument or based at least in part upon an extension of the identified instrument.

In another aspect, a Q3D system identifies a target instrument within a scene. A mark is produced in a visual 3D representation of the scene that indicates a Q3D location of the identified target instrument within the visual 3D representation of the scene.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

Figure 16:
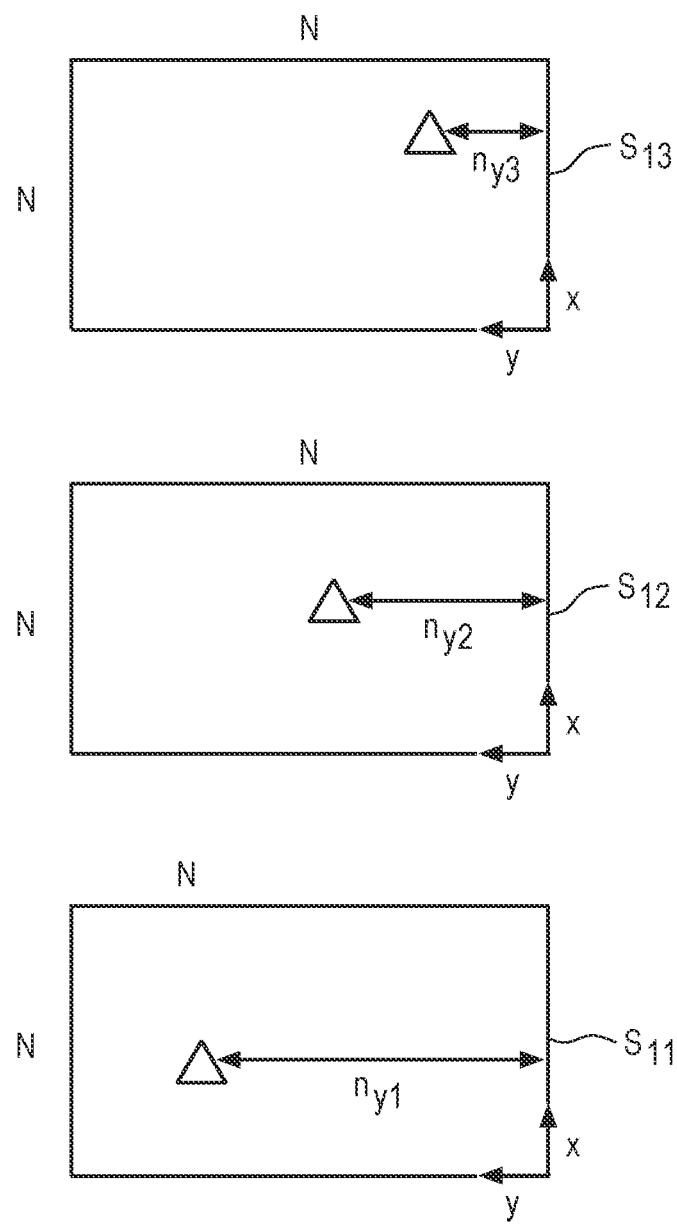
FIG. 16 is an illustrative drawing showing projections of a selected target point onto multiple sensors in accordance with some embodiments.
Figure 18:
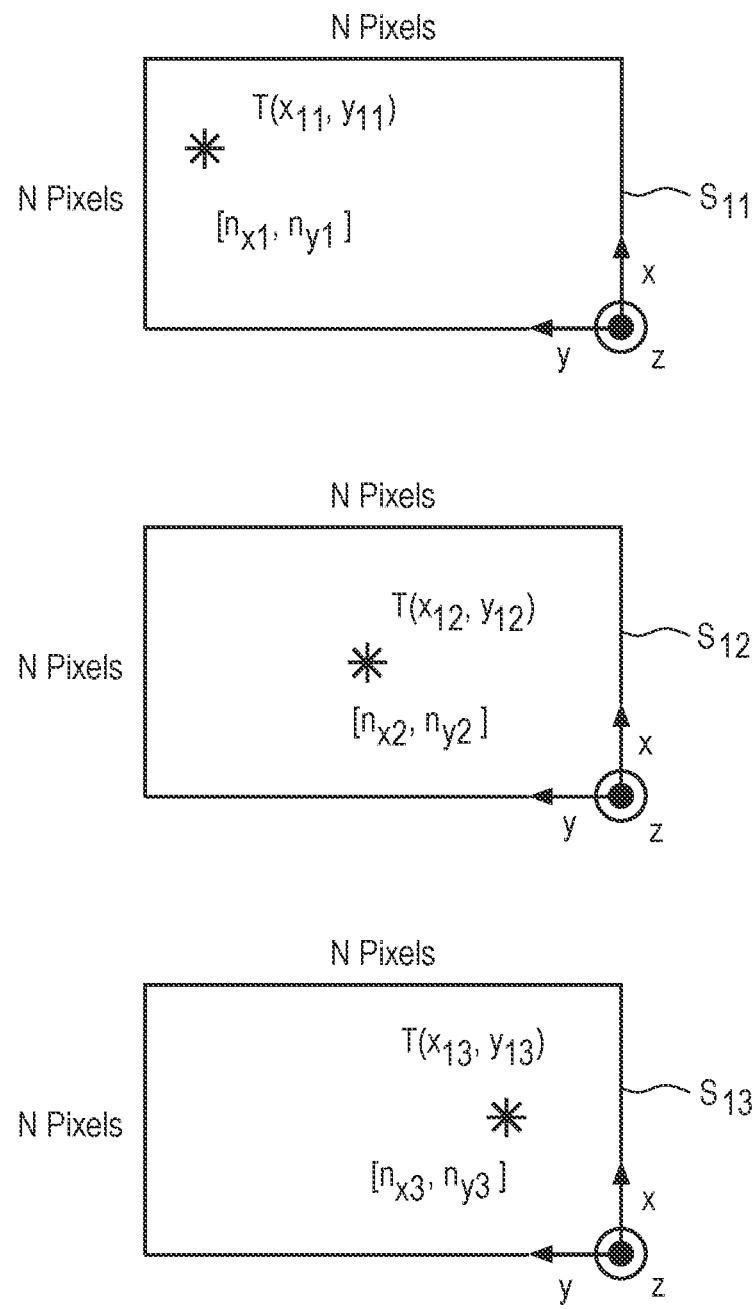

FIG. 18 is an illustrative elevation view of the projection of the currently selected target point T onto the multiple image sensors of FIG. 16 in accordance with some embodiments.

Figure 19:
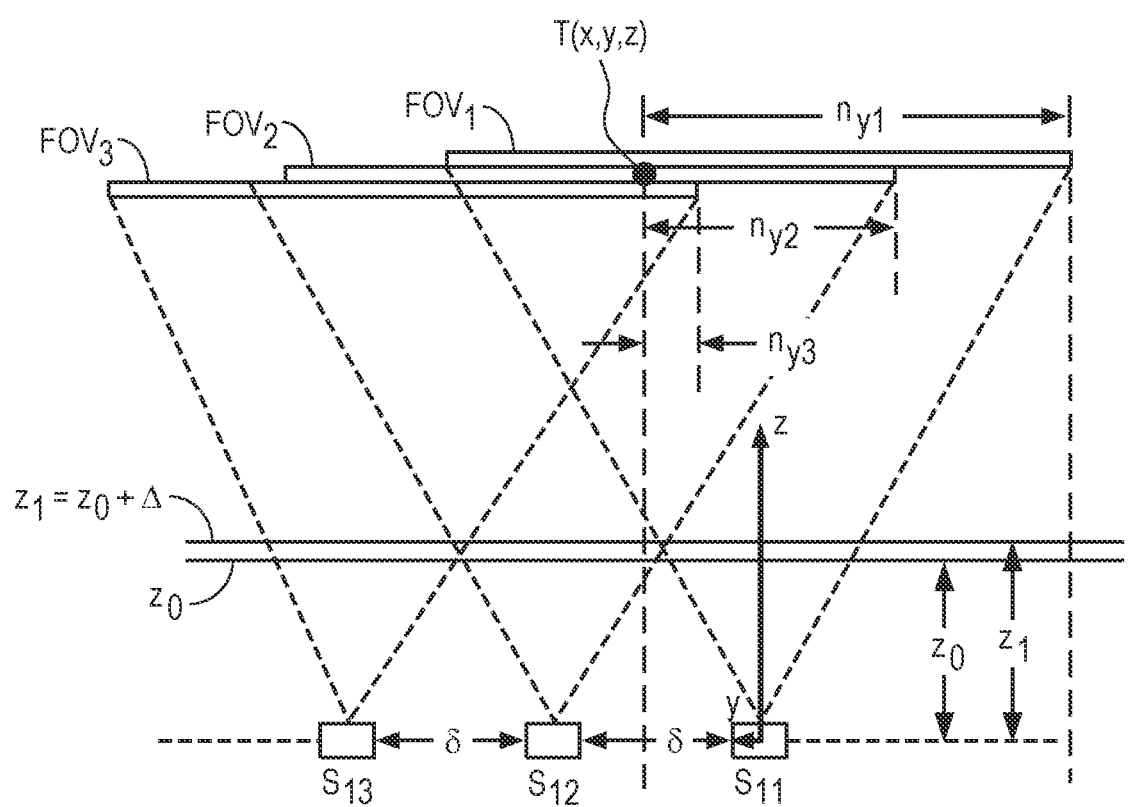

FIG. 19 is an illustrative drawing showing the disposition of a currently selected target relative to the multiple sensors as described above with reference to FIG. 17 and also showing y-direction pixel offsets for the candidate pixel in each of the sensors in accordance with some embodiments.

Figure 20:
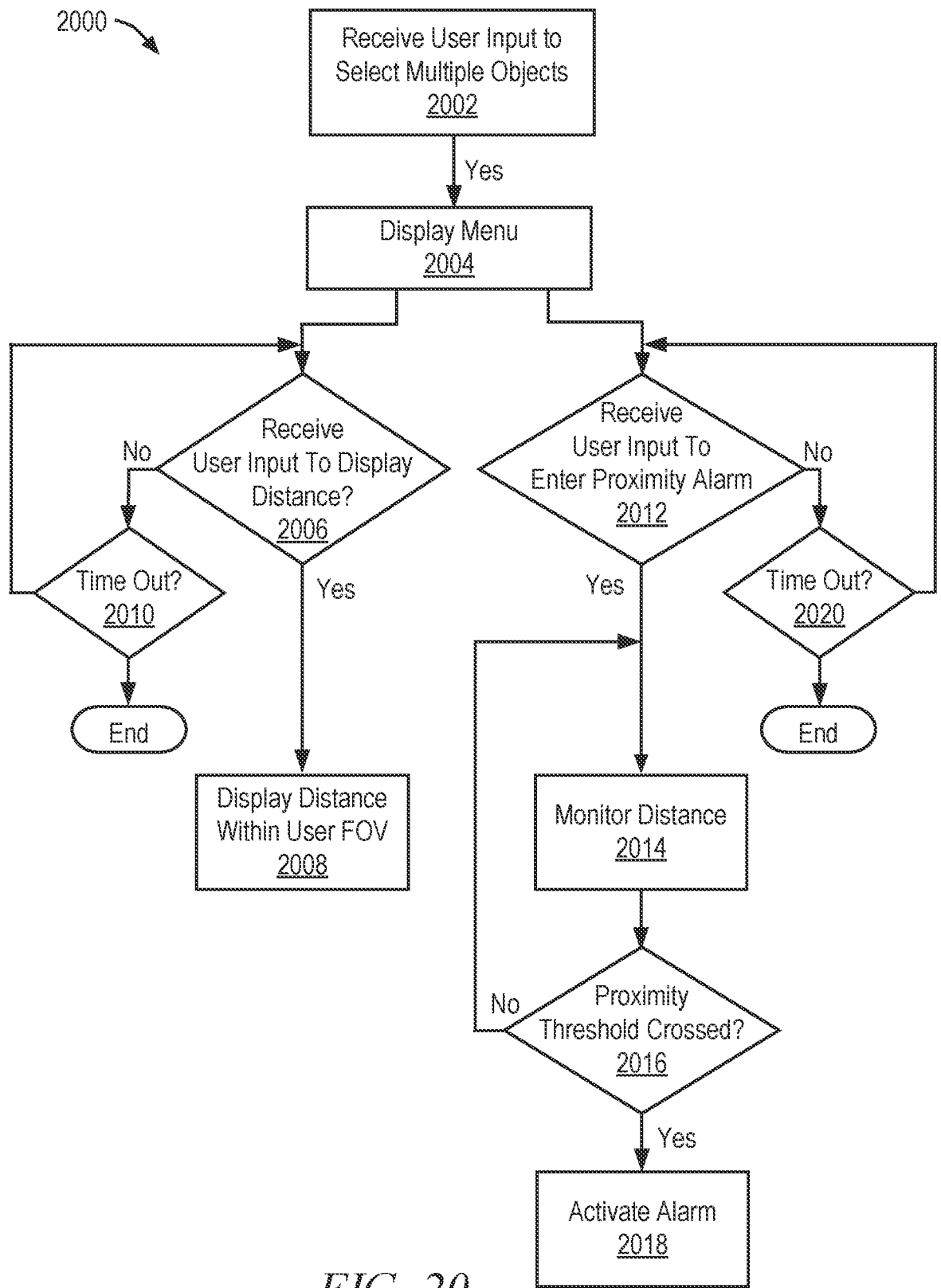

FIG. 20 is an illustrative flow diagram representing a first process to use Q3D information during a surgical procedure in accordance with some embodiments.

Figure 21:
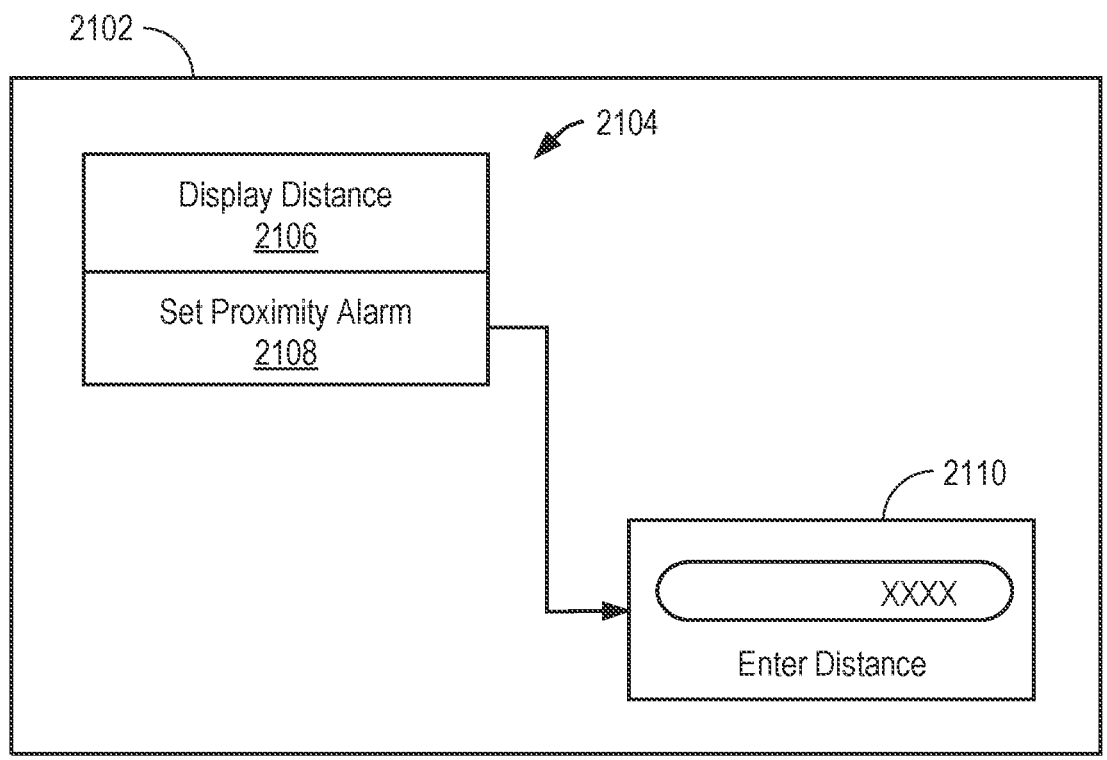

FIG. 21 is an illustrative drawing showing menu selections displayed on a display screen in accordance with the process of FIG. 20 in accordance with some embodiments.

Figure 22A:
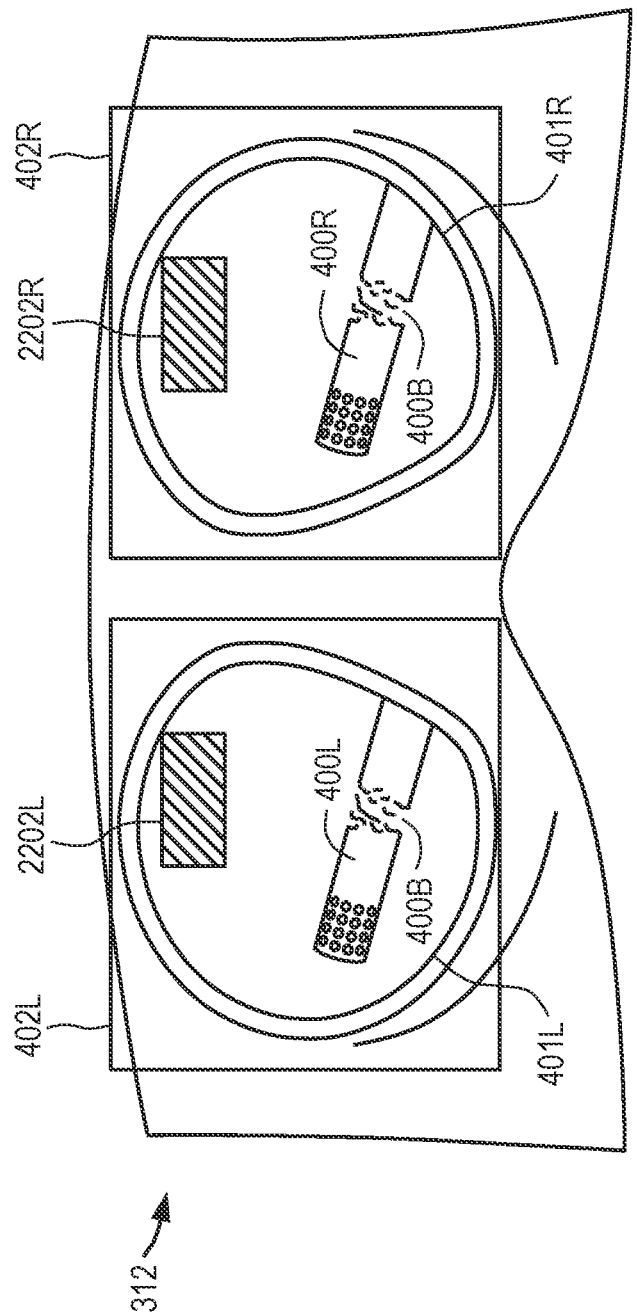
Figure 22B:
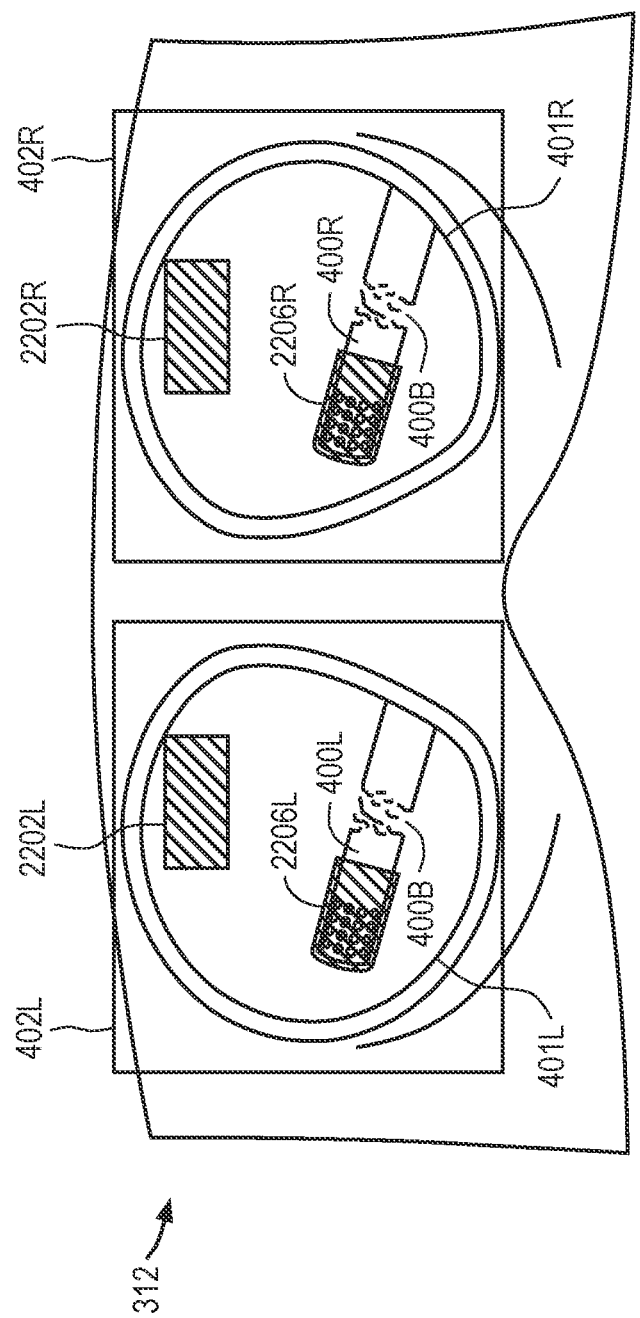

FIGS. 22A-22B are illustrative drawings representing certain details of receiving user input in accordance with the process of FIG. 20 in accordance with some embodiments.

Figure 23:
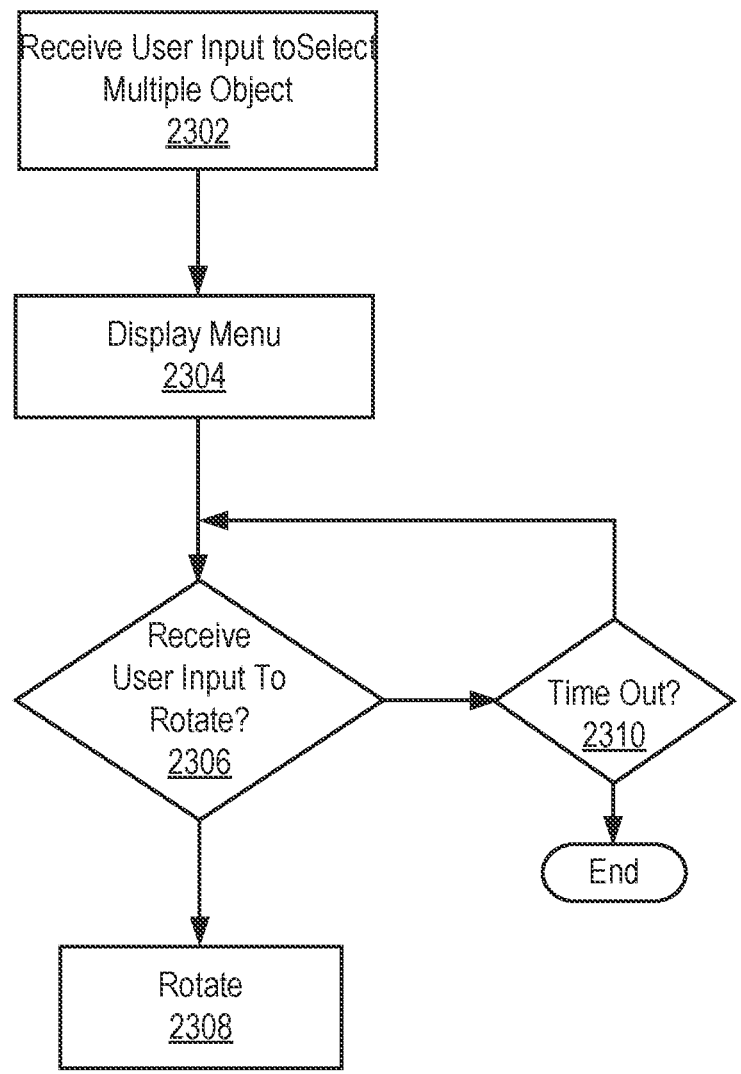

FIG. 23 is an illustrative flow diagram representing a second process to use Q3D information during a surgical procedure in accordance with some embodiments.

Figure 24:
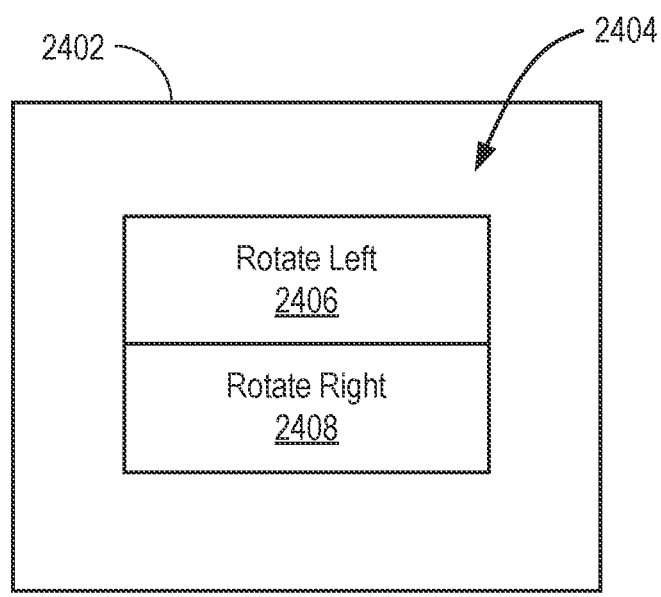

FIG. 24 is an illustrative drawing showing menu selections displayed on a display screen in accordance with the process of FIG. 23 in accordance with some embodiments.

Figure 25:
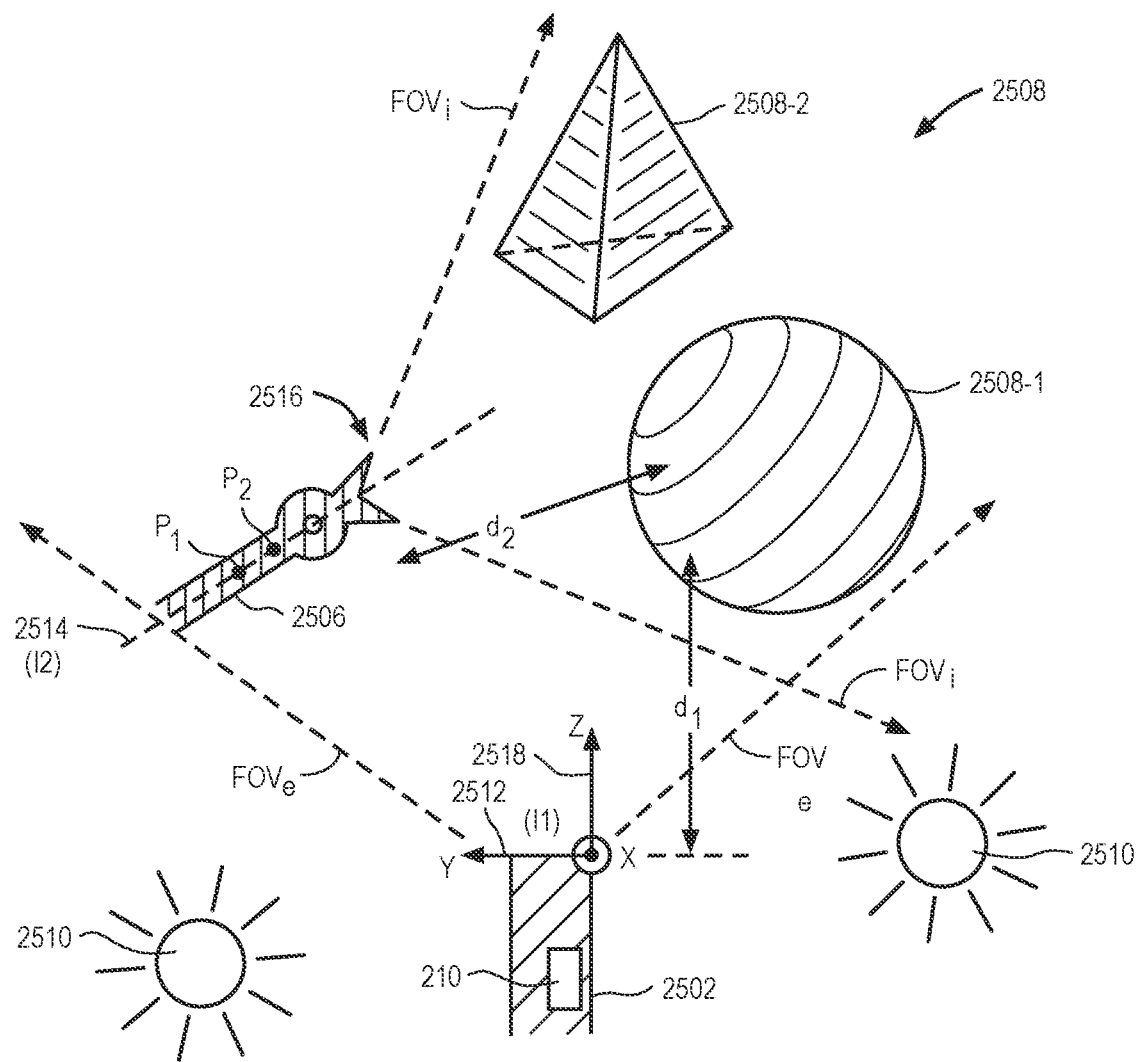

FIG. 25 is an illustrative drawing showing a perspective view of a Q3D endoscope that is associated with an image sensor array and that has a field of view that encompasses a portion of a surgical instrument and one or more anatomical structures in accordance with some embodiments.

Figure 26:
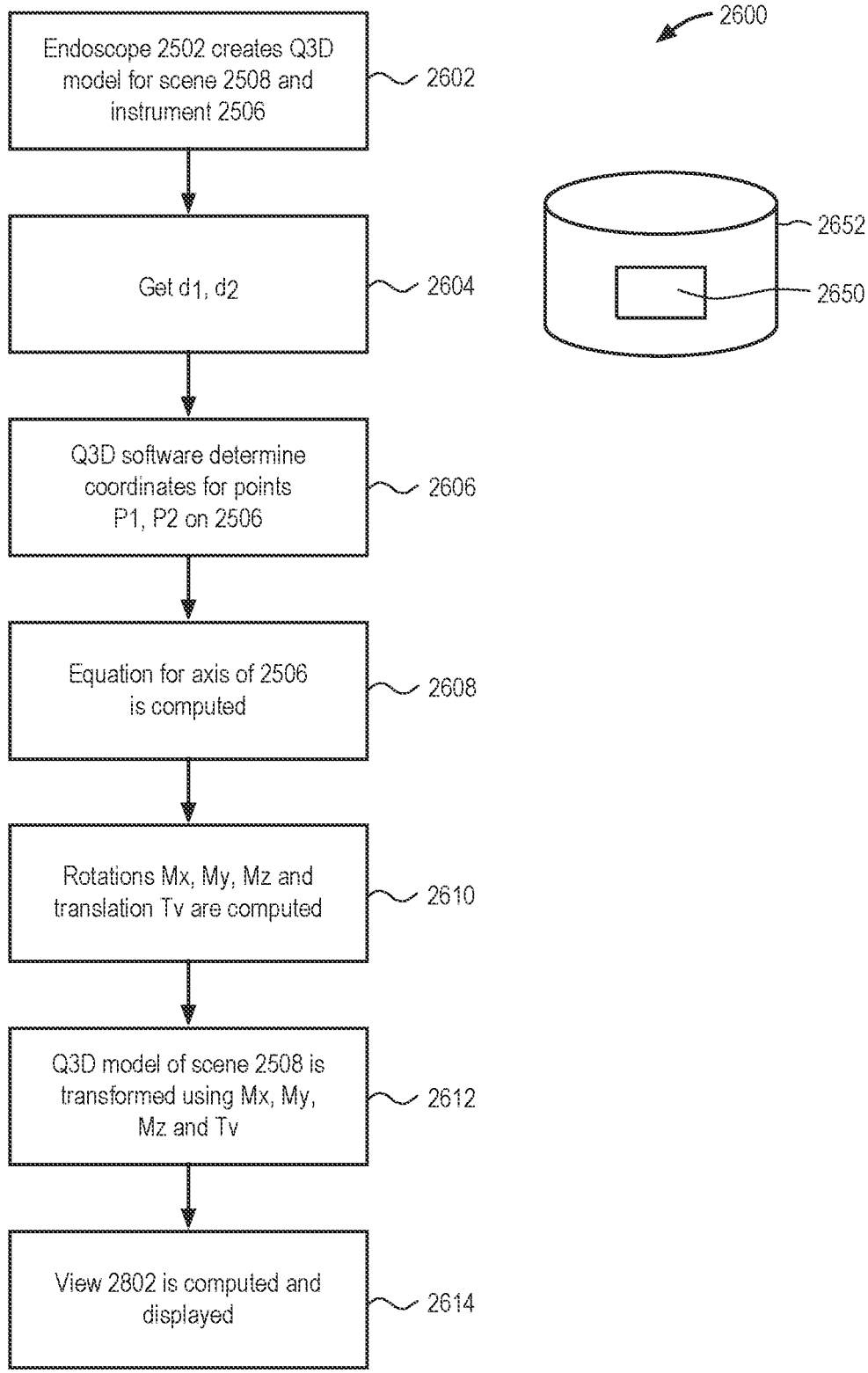

FIG. 26 is an illustrative flow diagram representing a process to convert a Q3D scene from an endoscope viewing perspective to a Q3D scene from a perspective of a target instrument within the endoscope viewing perspective in accordance with some embodiments.

Figure 27A:
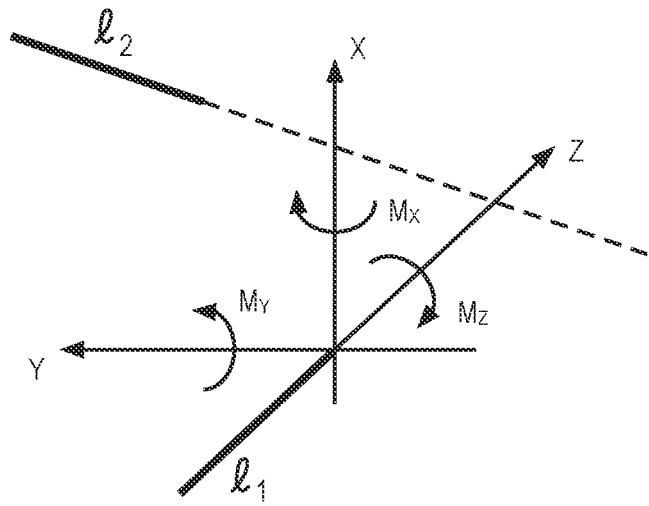
Figure 27B:
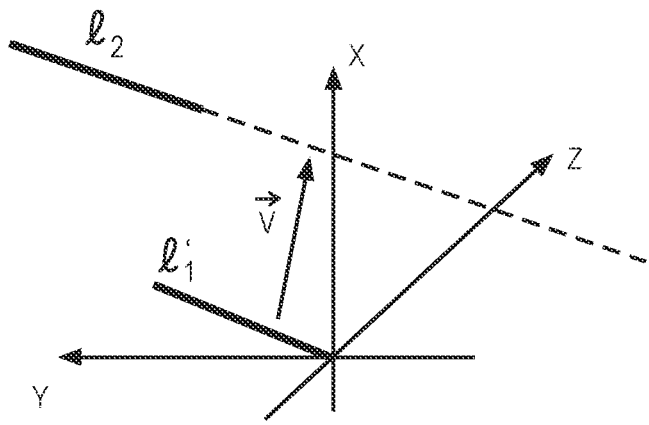
Figure 27C:
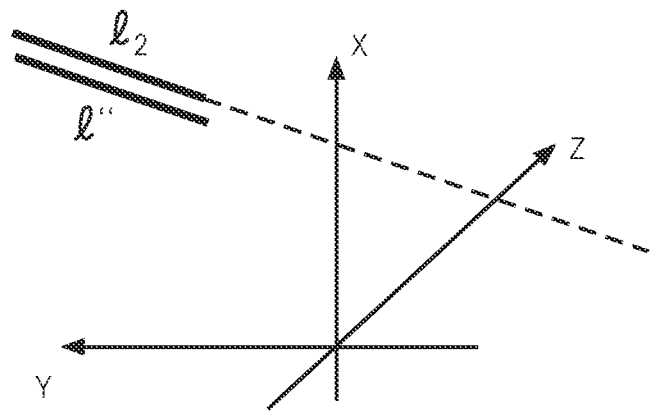

FIGS. 27A-27C are illustrative drawings representing virtual orientation transformations (FIG. 27A), virtual location transformation (FIG. 27B) and a resulting virtual alignment (FIG. 27C) in accordance with some embodiments.

Figure 28A:
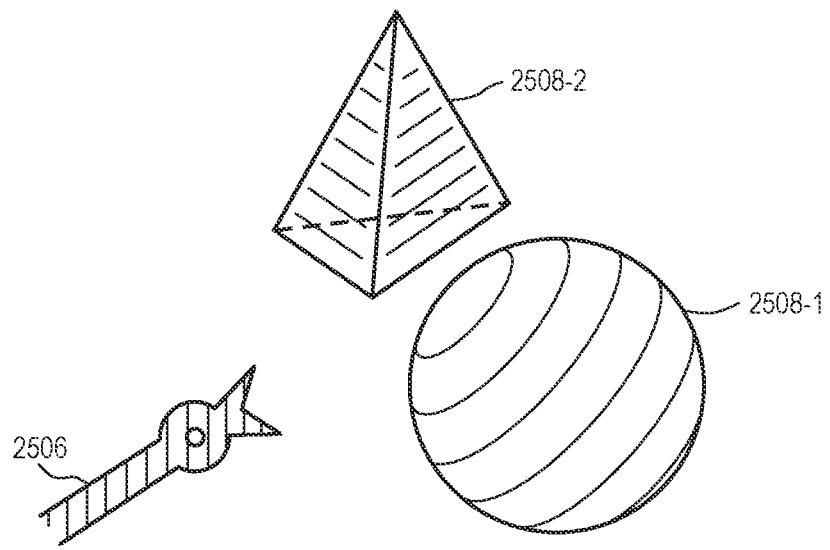
Figure 28B:
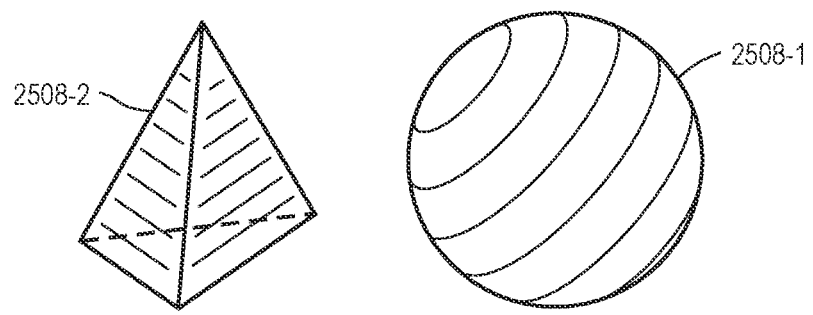

FIG. 28A-28B are example Q3D views of the surgical scene from a perspective of the endoscope tip (FIG. 28A) and from a perspective of the target surgical instrument (FIG. 28B) in accordance with some embodiments.

Figure 29:
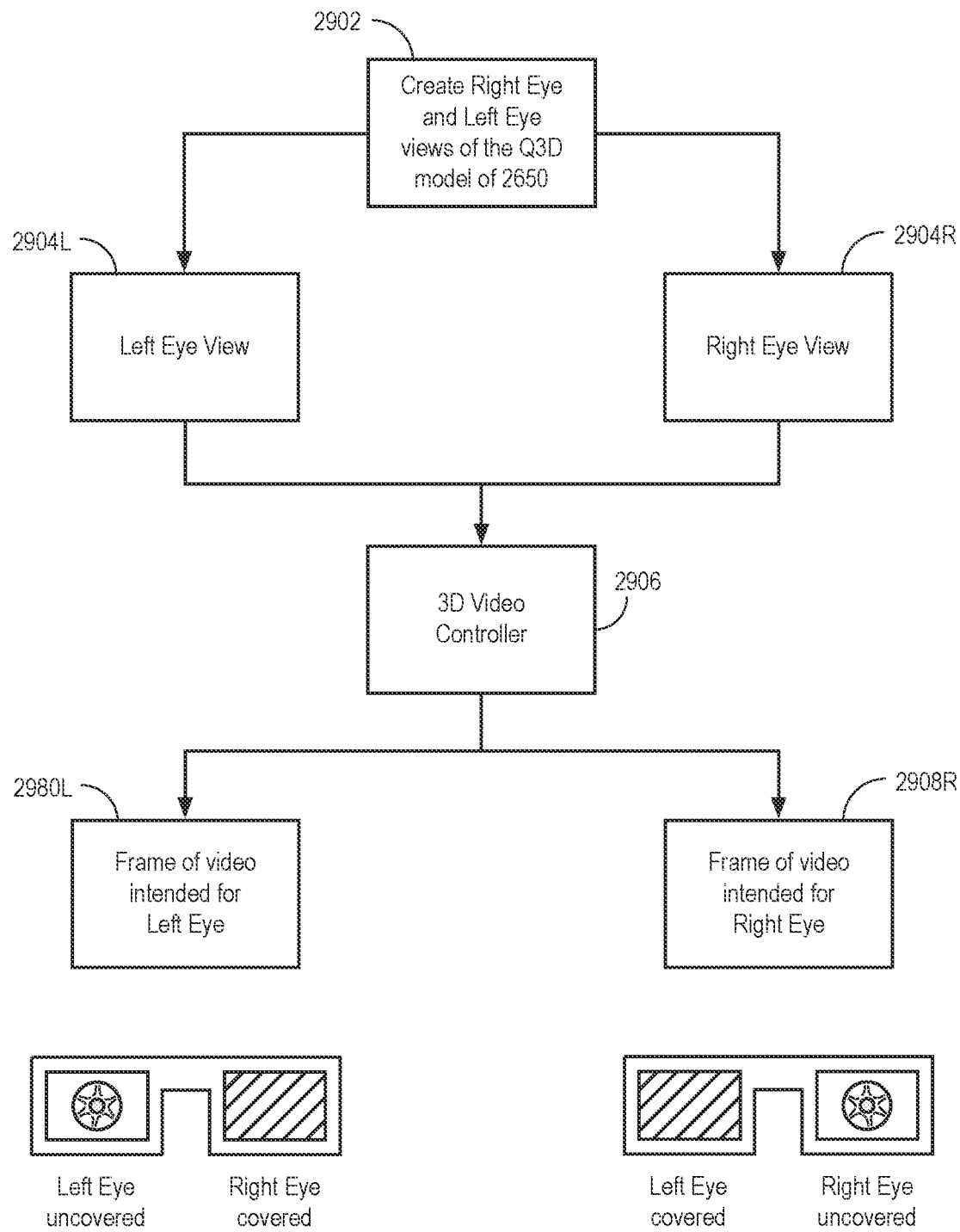

FIG. 29 is an illustrative drawing showing details of a processor that displays the Q3D model in a 3D) perspective on a 3D display in accordance with some embodiments.

Figure 5:
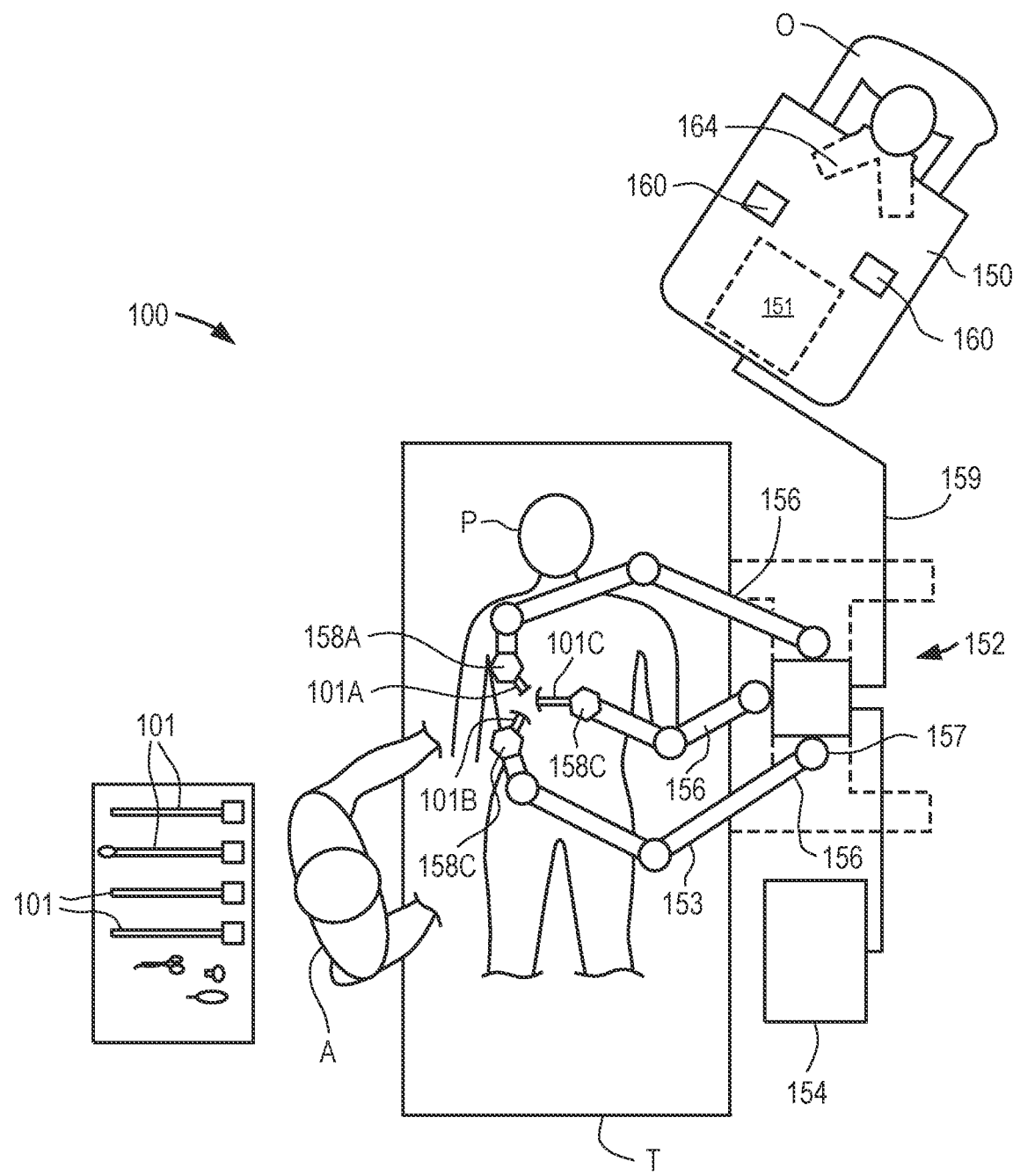
FIG. 5 is an illustrative block diagram of a teleoperation surgery system to perform minimally invasive surgical procedures using one or more mechanical arms in accordance with some embodiments.
Figure 6:
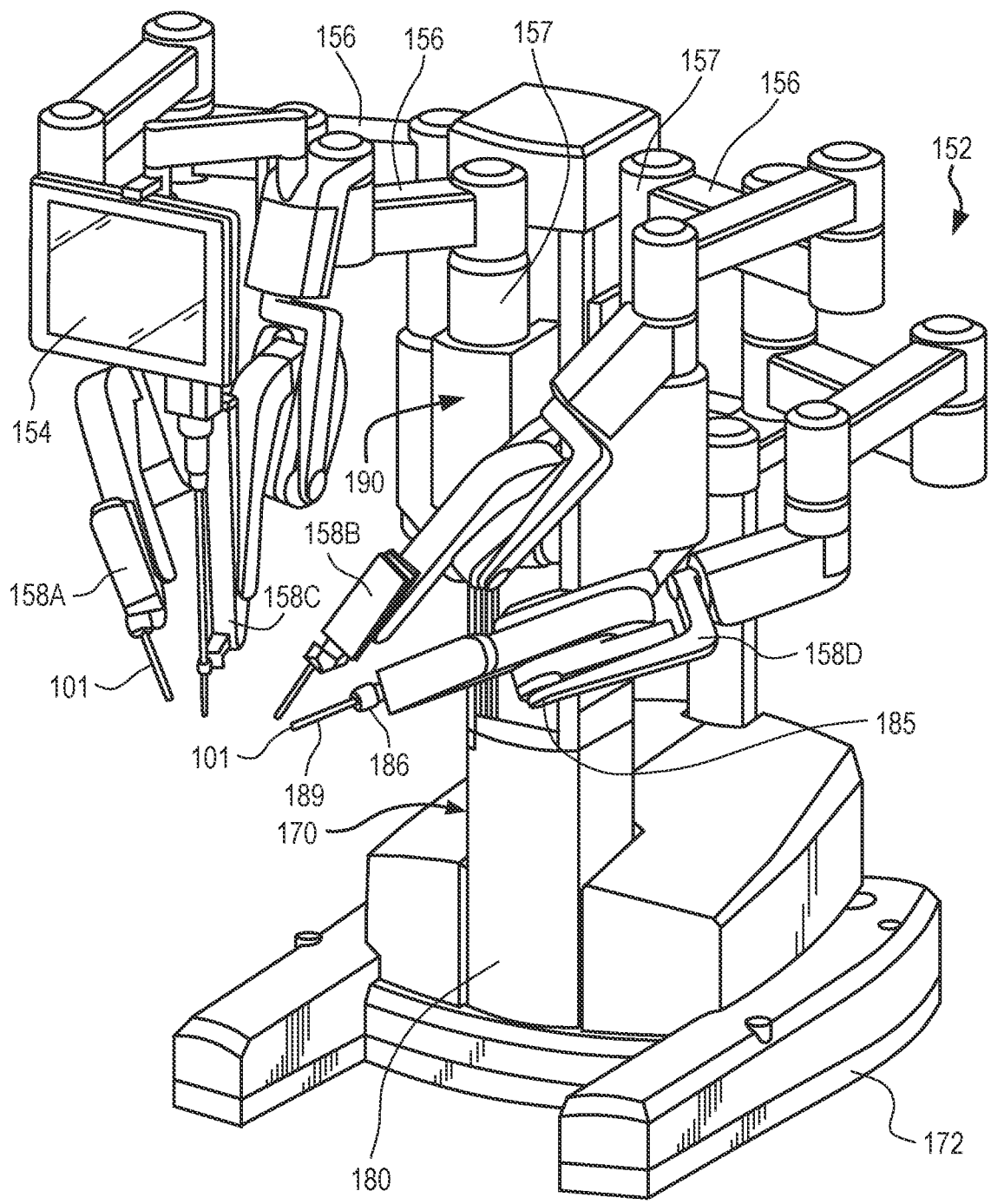
FIG. 6 is an illustrative perspective view of a patient-side system of the system of FIG. 5 in accordance with some embodiments.
Figure 30A:
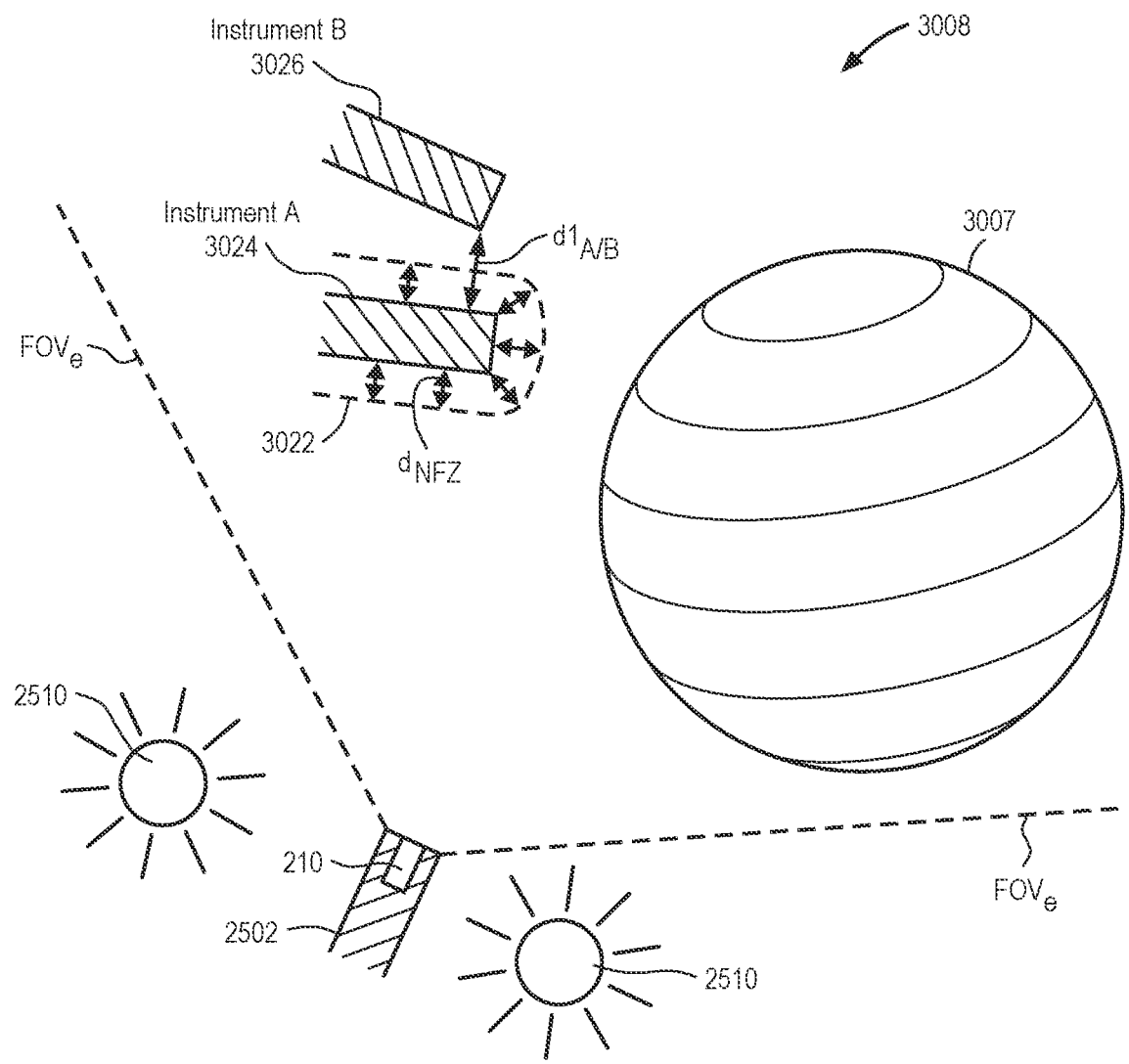
Figure 30B:
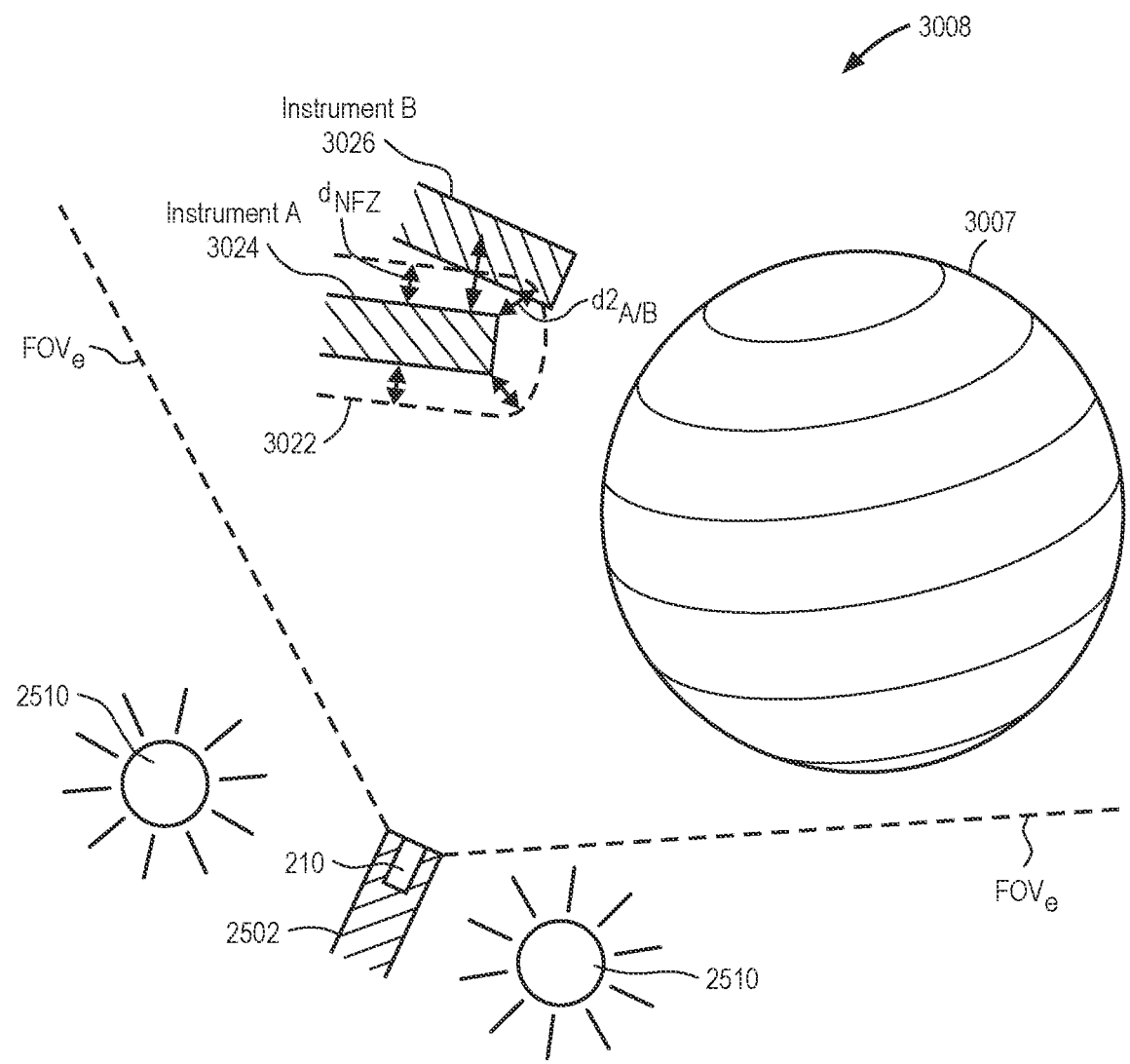

FIGS. 30A-30B are illustrative perspective views of a Q3D endoscope deployed as described in reference to FIGS. 5-6 and perspective views of instruments within the endoscope the field of view (FOV$_e$), displaying a respective no fly zone about one of the instruments in accordance with some embodiments.

Figure 31:
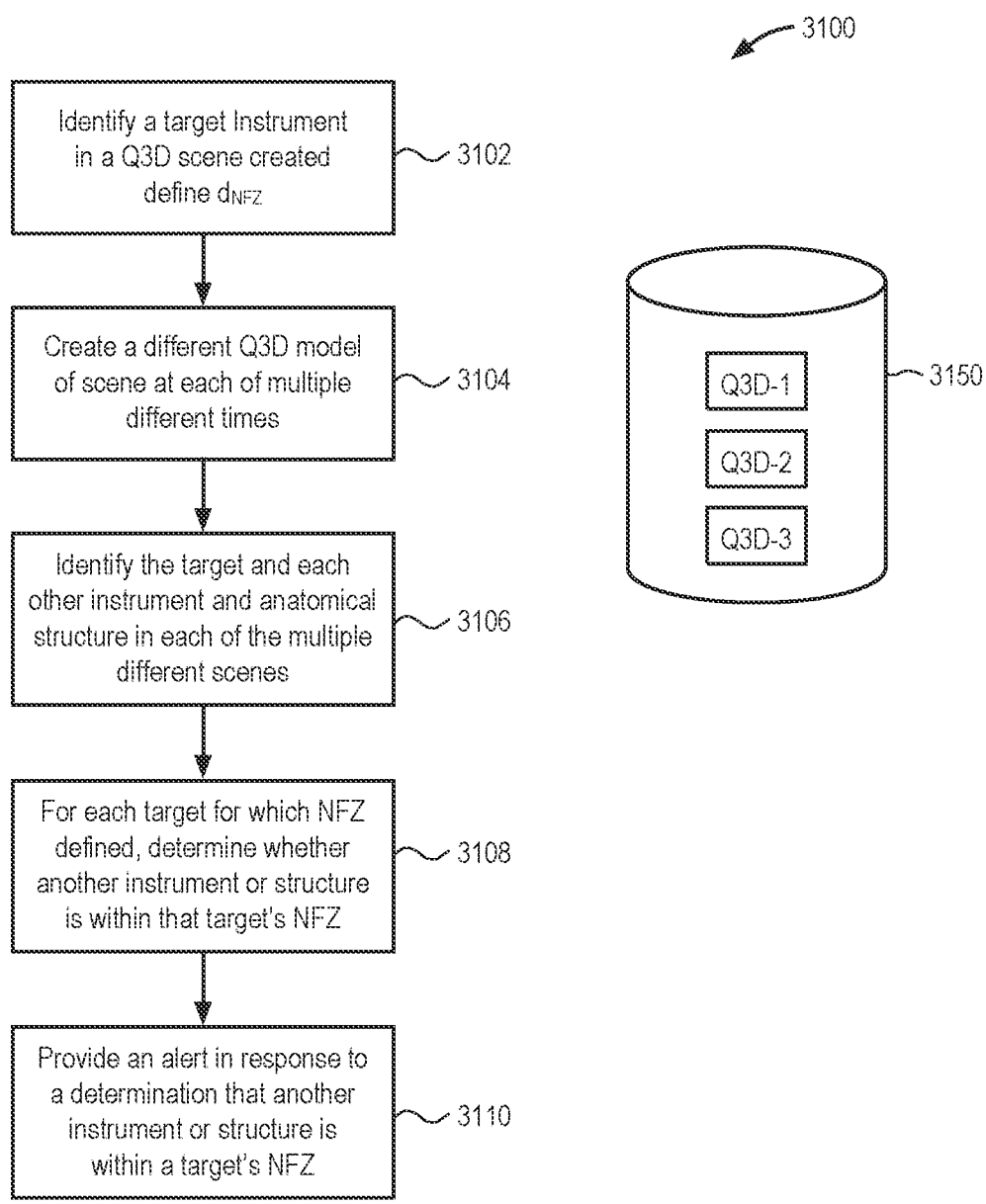

FIG. 31 is an illustrative flow diagram representing a process to define a no fly zone and to determine whether the no fly zone has been violated in accordance with some embodiments.

Figure 32:
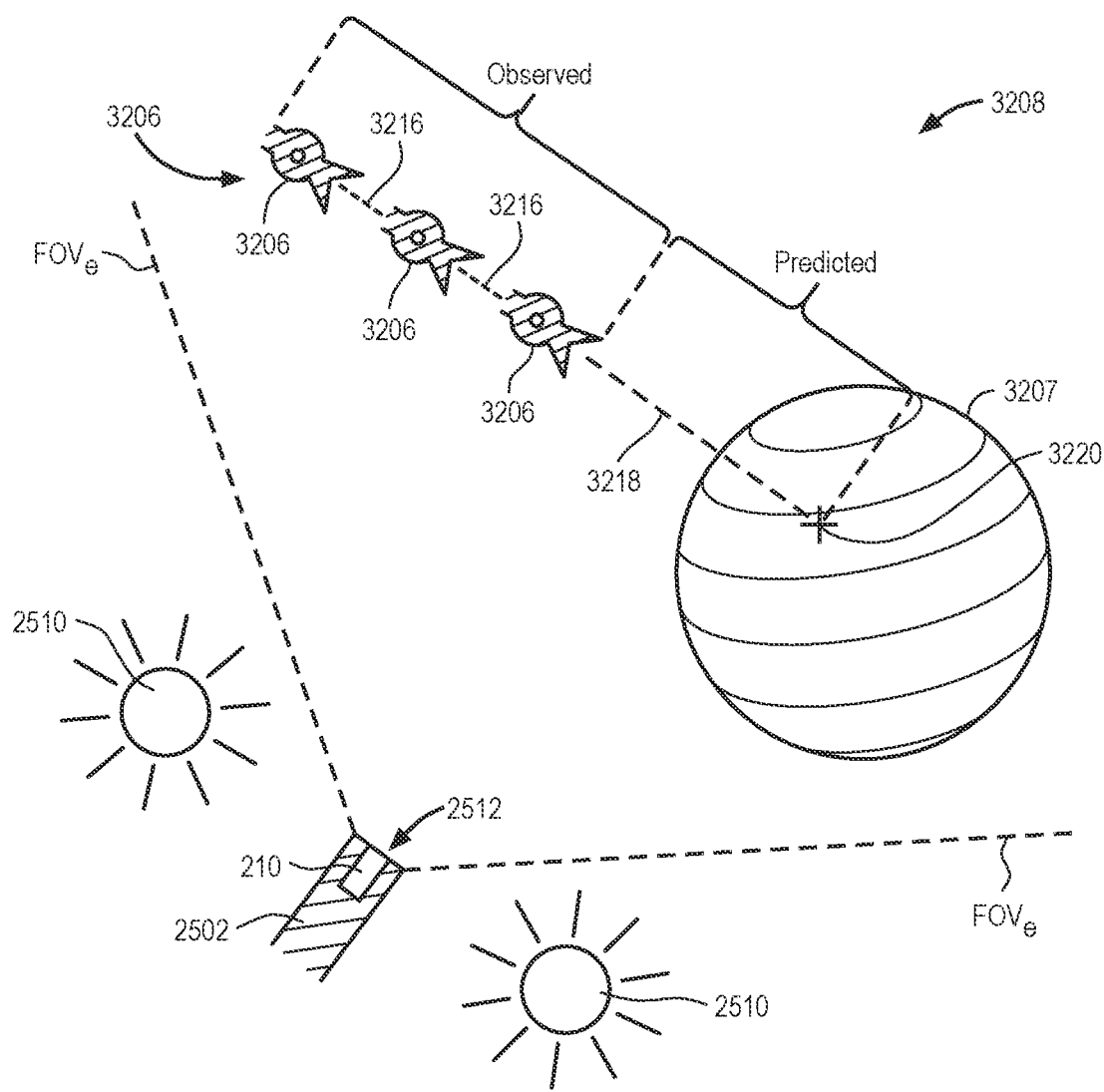

FIG. 32 is an illustrative drawing showing a Q3D endoscope having an endoscope field of view (FVO$_e$) and a portion of a surgical instrument, observed at multiple different positions on an observed trajectory, and an anatomical structure disposed in a surgical scene within the FOV$_e$ in accordance with some embodiments.

Figure 33:
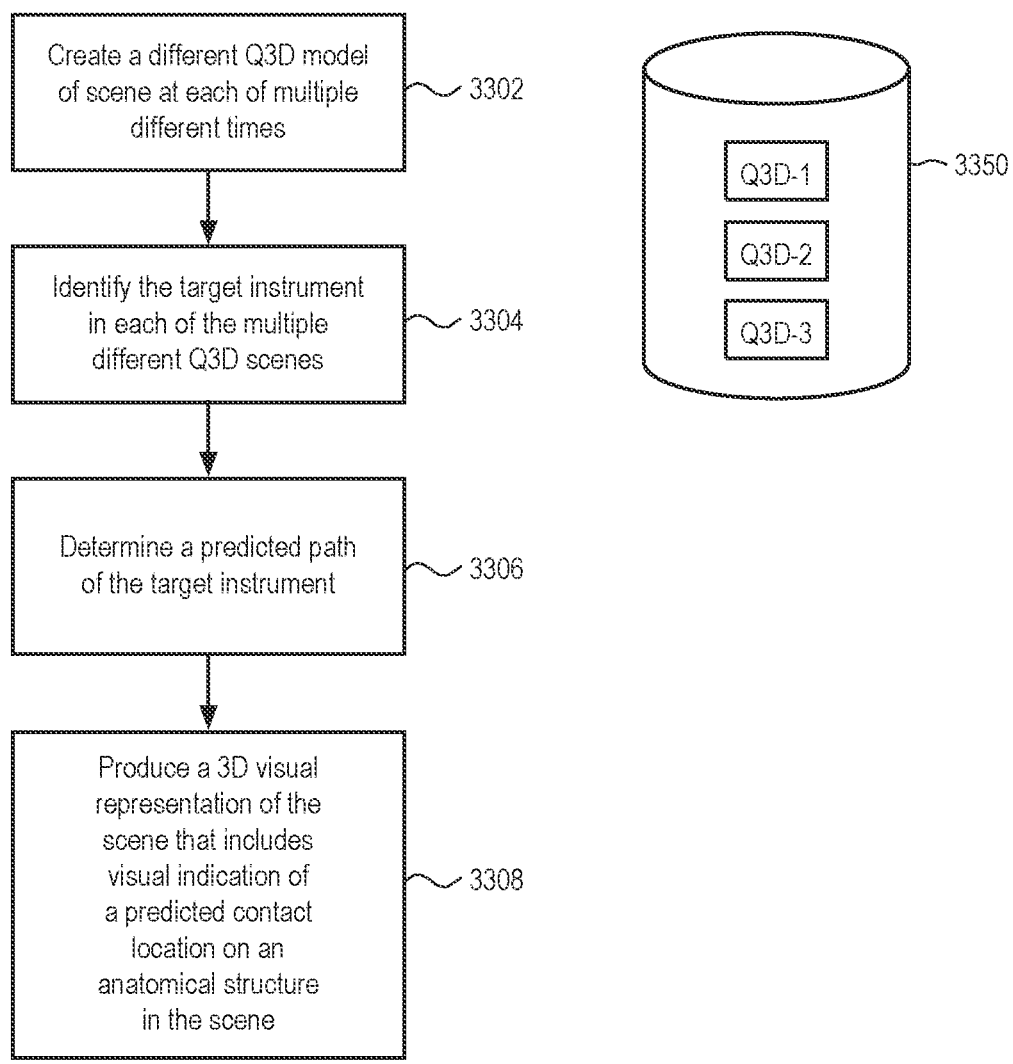

FIG. 33 is an illustrative flow diagram representing a process to track a target instrument on an observed path in a Q3D scene and to determine a predicted path and predicted contact location in accordance with some embodiments.

Figure 34:
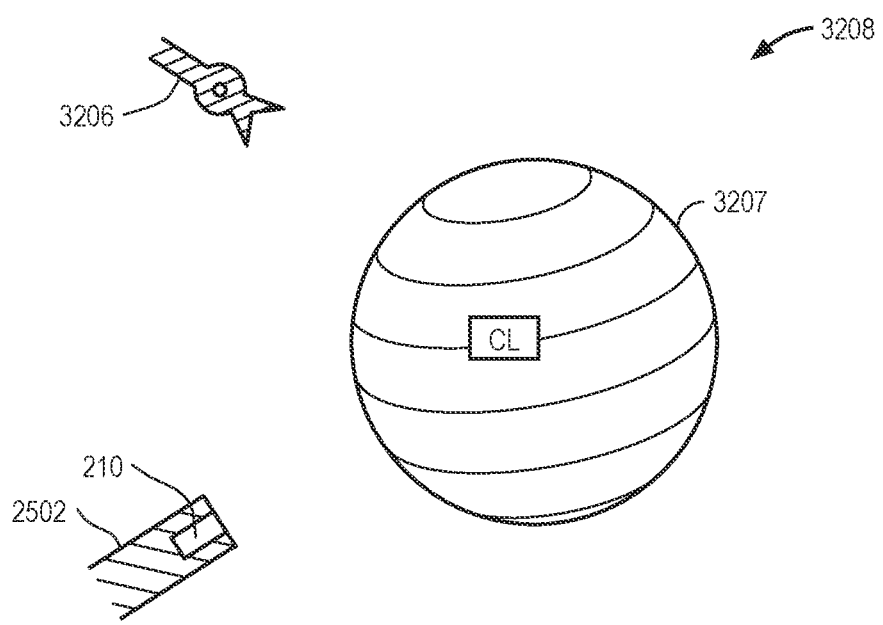

FIG. 34, there is shown an example 3D visual representation of the scene in which the target instrument in the third position is shown and a predicted contact location marked with a visual marker on the anatomical structure in accordance with some embodiments.

Figure 35:
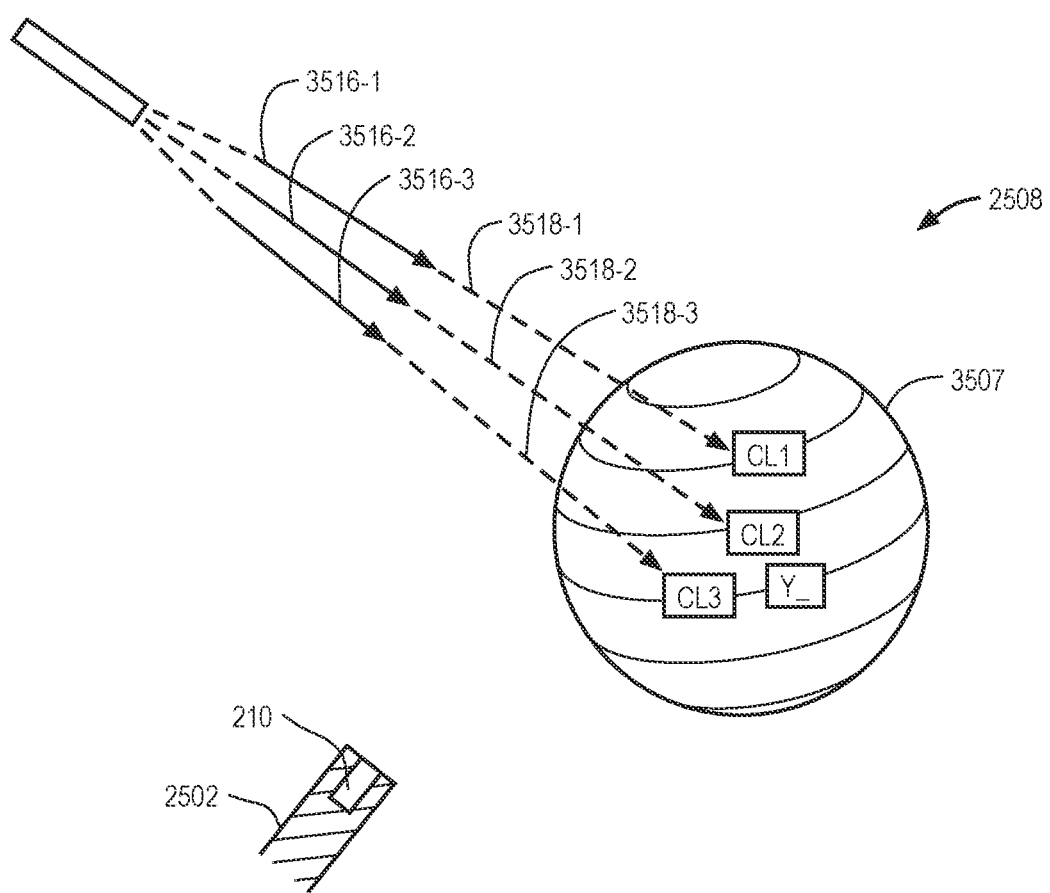

FIG. 35 is an illustrative drawing representing an example surgical scene in multiple different observed paths and corresponding predicted paths and contact locations plus a desired contact location in accordance with some embodiments.

Figure 36:
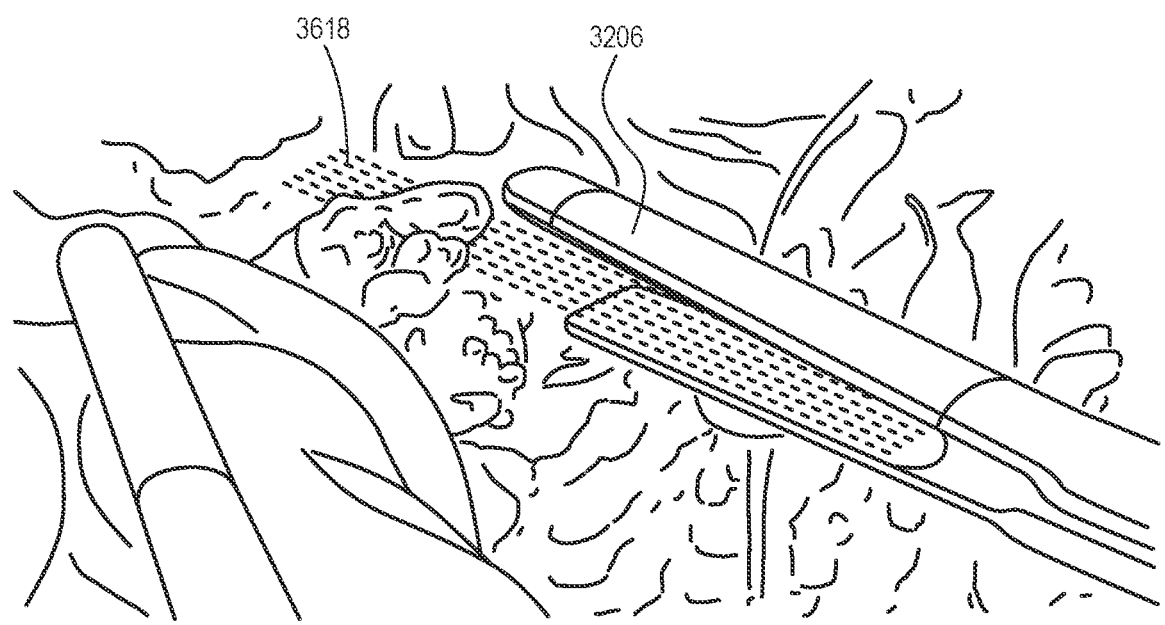

FIG. 36 is an illustrative drawing showing a 3D view of a surgical scene that includes a stapler and a predicted path representing an extension of the staple lines and knife channel in accordance with some embodiments.

Figure 37:
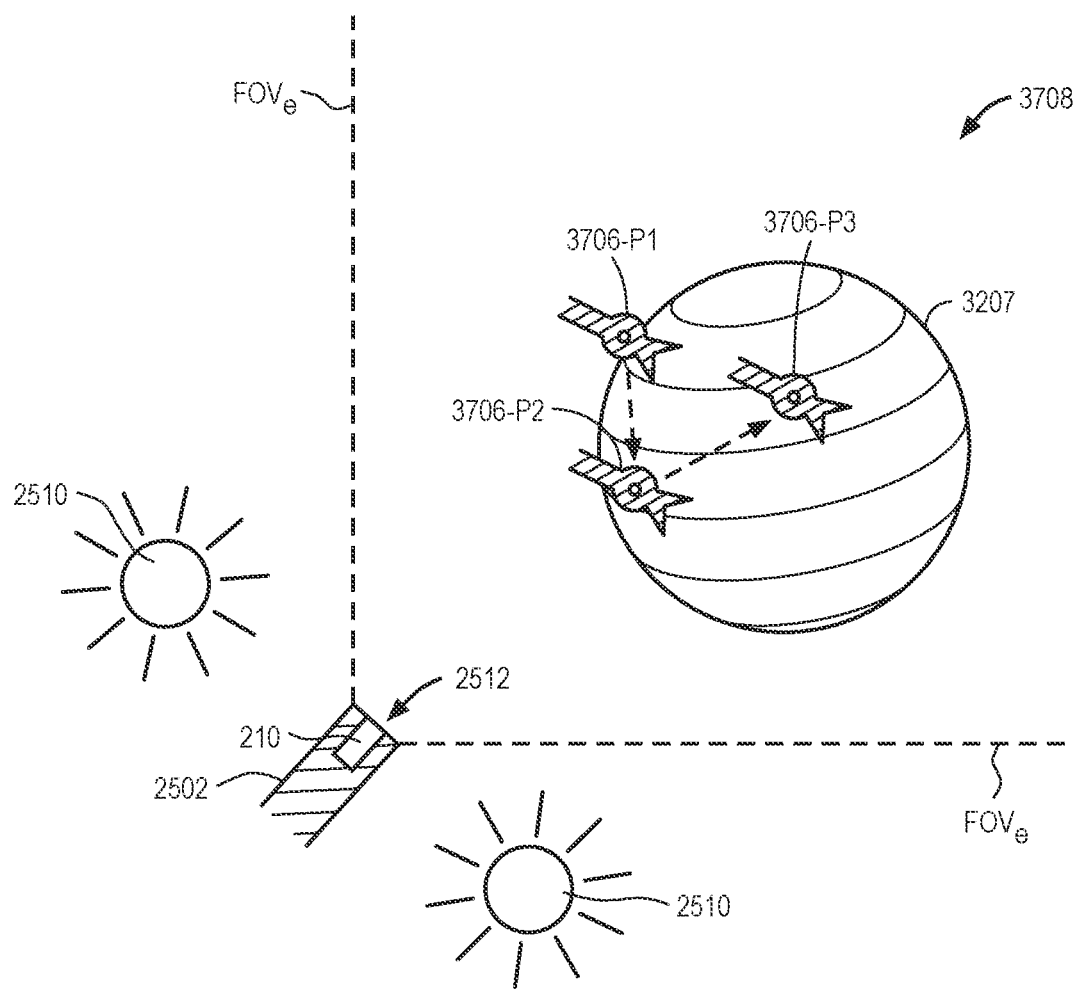

FIG. 37 is an illustrative drawing showing a Q3D endoscope having an endoscope field of view (FOV$_e$) and a portion of a surgical instrument, shown at multiple different positions, and an anatomical structure disposed in a surgical scene within the FOV$_e$ in accordance with some embodiments.

Figure 38A:
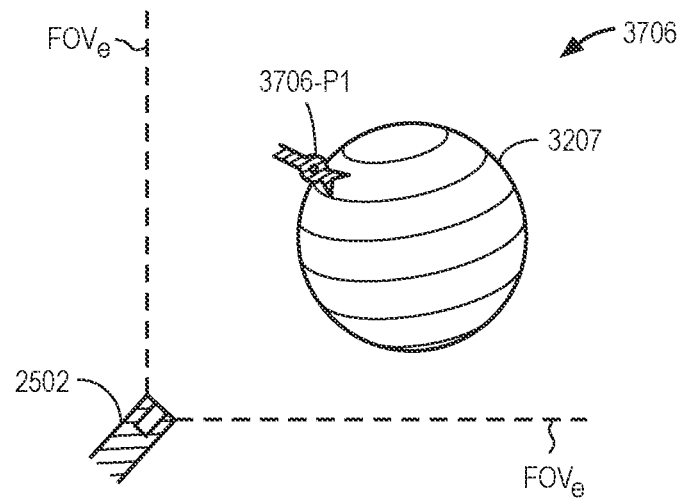
Figure 38B:
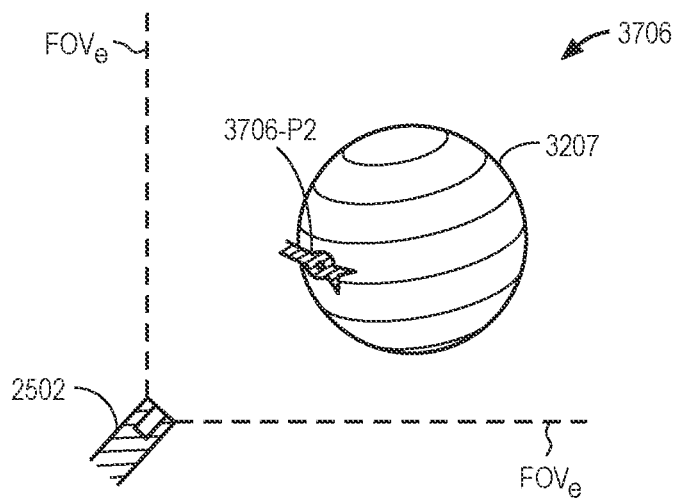
Figure 38C:
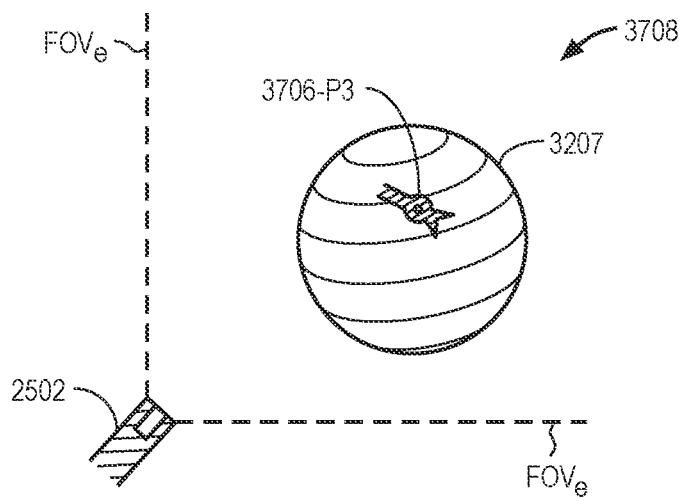

FIGS. 38A-38C are illustrative drawings representing changes in position of the target instrument from a position at a first point in time (FIG. 38A) to a position at a second point in time (FIG. 38B) to a position at a third point in time (FIG. 38C) in accordance with some embodiments.

Figure 39:
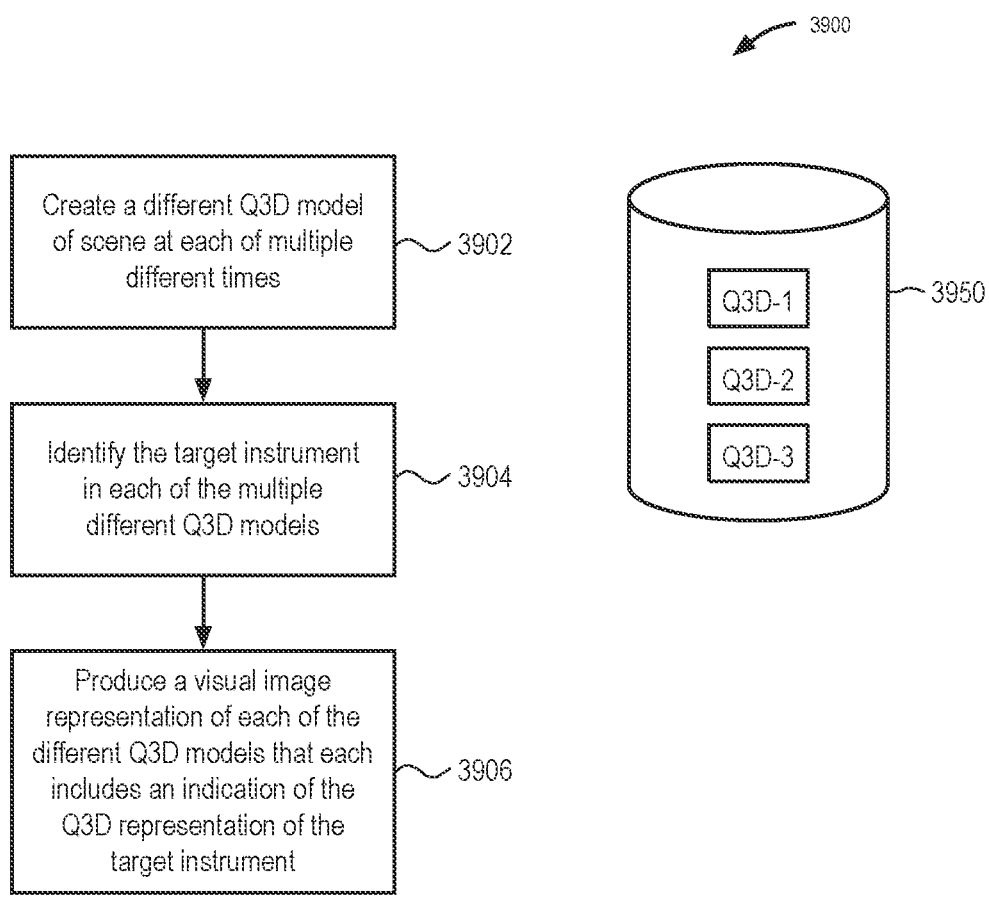

FIG. 39 is an illustrative flow diagram representing a process to track a target instrument in a Q3D in accordance with some embodiments.

Figure 40:
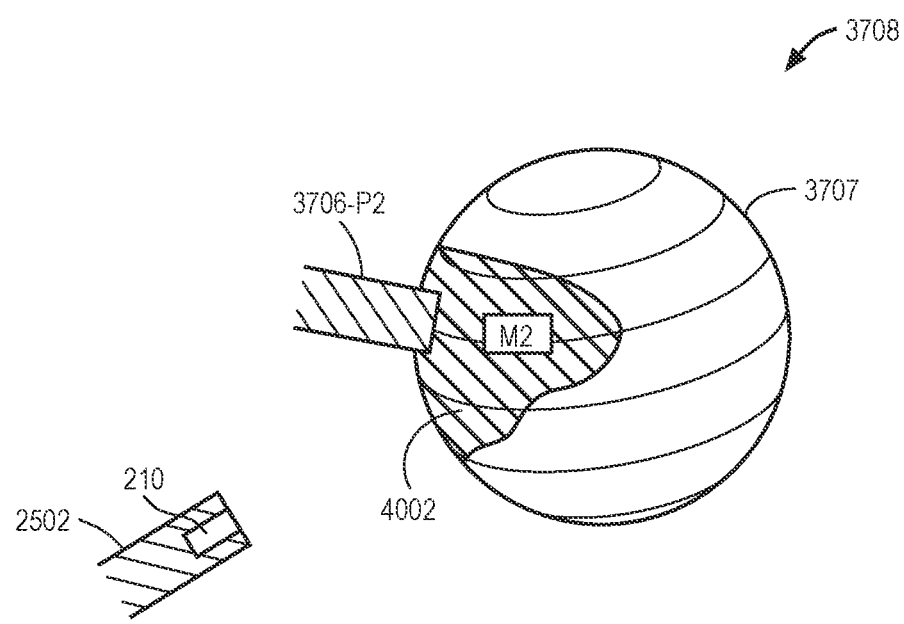

FIG. 40 is an illustrative drawing showing an example 3D visual representation of the scene in which the target instrument in the second position is shown associated with a visual marker in accordance with some embodiments.

DESCRIPTION OF EMBODIMENTS

The following description is presented to enable any person skilled in the art to create and use a surgical endoscopy system having multiple image sensors, each sensor including a pixel array that is separate from pixel arrays of other sensors, so as to determine three-dimensional coordinates of physical structures within a field of view of the image sensors. Various modifications to the embodiments will be readily apparent to those skilled in the art, and the generic principles defined herein may be applied to other embodiments and applications without departing from the spirit and scope of the inventive subject matter. Moreover, in the following description, numerous details are set forth for the purpose of explanation. However, one of ordinary skill in the art will realize that the inventive subject matter might be practiced without the use of these specific details. In other instances, well-known machine components, processes and data structures are shown in block diagram form in order not to obscure the disclosure with unnecessary detail. Identical reference numerals may be used to represent different views of the same item in different drawings. Flow diagrams in drawings referenced below are used to represent processes. A computer system may be configured to perform some of these processes. Modules within flow diagrams representing computer implemented processes represent the configuration of a computer system according to computer program code to perform the acts described with reference to these modules. Thus, the inventive subject matter is not intended to be limited to the embodiments shown, but is to be accorded the widest scope consistent with the principles and features disclosed herein.

Brief Overview

In accordance with some embodiments, an imager that includes a sensor array is associated with an endoscope. The image sensor array includes multiple sensors, and each sensor includes an array of pixels. A portion of the endoscope is inserted into a human body cavity, and a target object in a field of view of the image sensor array is illuminated using a light source. A physical location and/or dimensions of the target object is determined based upon images of the target object projected onto individual sensors of the array.

Figure 1:
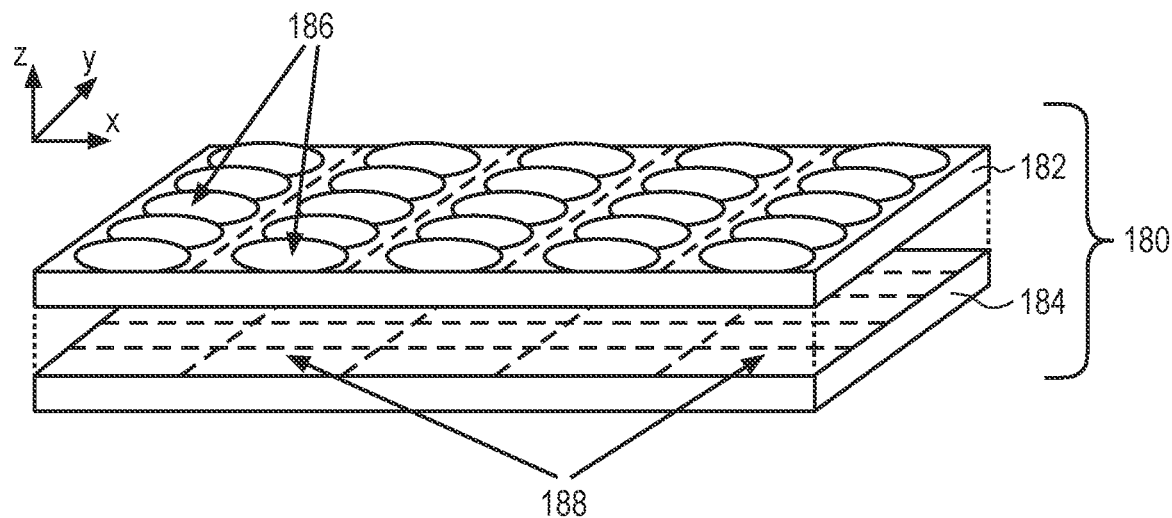
FIG. 1 is an illustrative drawing showing details of a known imager sensor.
Figure 2:
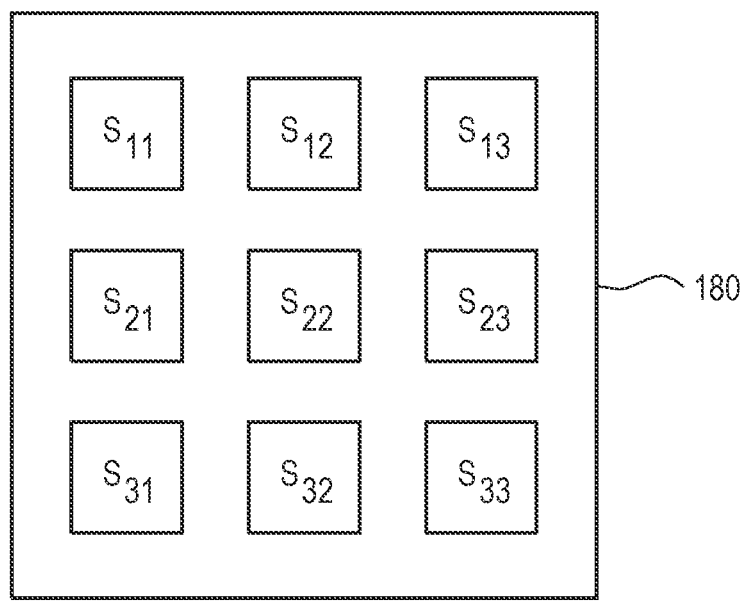
FIG. 2 is an illustrative drawing showing a simplified plan view of a known arrangement of sensors of the imager sensor of FIG. 1.
Figure 3:
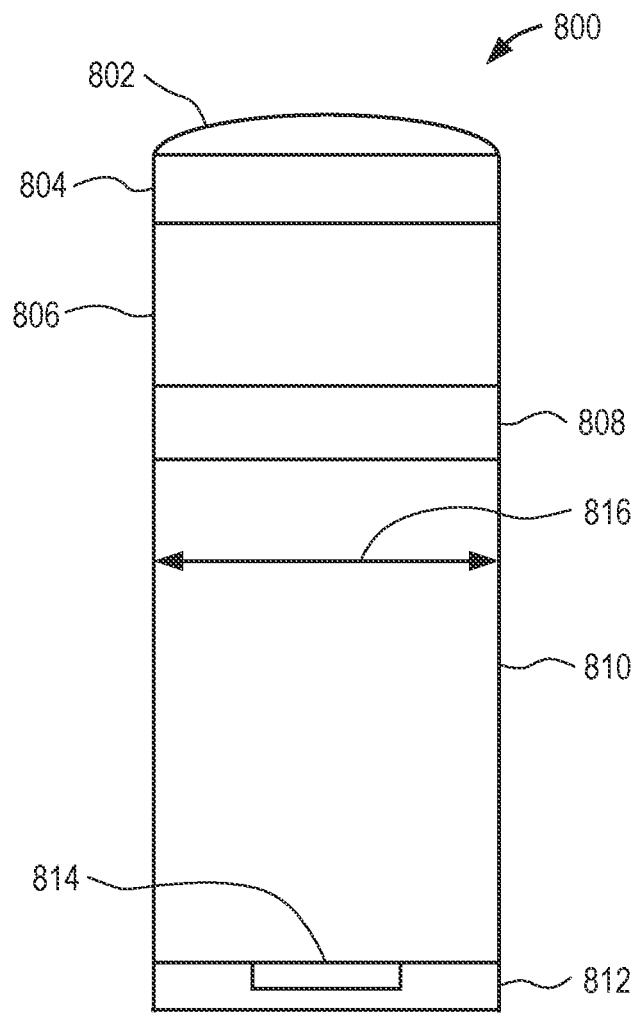
FIG. 3 is an illustrative drawing of a known microlens pixel stack of a pixel within a sensor of the sensor array of FIG. 2.
Figure 4:
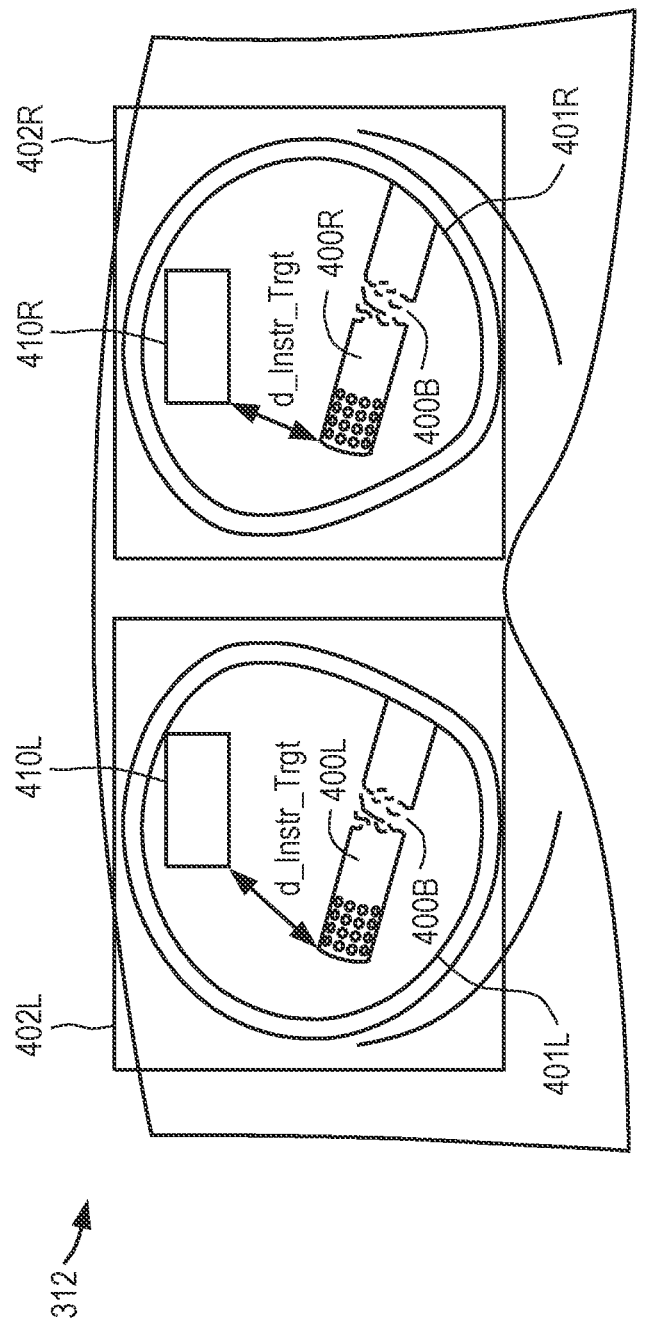
FIG. 4 is an illustrative drawing showing a perspective view of a surgical scene through a viewer in accordance with some embodiments.

FIG. 4 is an illustrative drawing showing a perspective view of a surgical scene through a viewer 312 in accordance with some embodiments. A viewing system having two viewing elements 401R, 401L can provide a good 3D viewing perspective. Numerical values representing physical dimension and/or location information for physical structures in the surgical scene are shown overlaid onto the surgical scene image. For example, a numerical distance value "d_Instr_Trgt" is shown displayed within the scene between instrument 400 and target 410.

Teleoperation Medical System

Teleoperation refers to operation of a machine at a distance. In a minimally invasive teleoperation medical system, a surgeon may use an endoscope that includes a camera to view a surgical site within a patient's body. Stereoscopic images have been captured, which allow the perception of depth during a surgical procedure. A camera system, which is mounted on an endoscope and which includes an imager sensor array, provides quantitative three-dimensional information plus color and illumination data that can be used to generate three-dimensional images in accordance with some embodiments.

FIG. 5 is an illustrative block diagram of a teleoperation surgery system 100 to perform minimally invasive surgical procedures using one or more mechanical arms 158 in accordance with some embodiments. Aspects of system 100 include telerobotic and autonomously operating features. These mechanical arms often support an instrument. For instance, a mechanical surgical arm (e.g., the center mechanical surgical arm 158C) may be used to support an endoscope with a stereo or three-dimensional surgical image capture device 101C, such as an endoscope associated a Q3D image sensor array. The mechanical surgical arm 158C may include a sterile adapter, or a clamp, clip, screw, slot/groove, or other fastener mechanism to mechanically secure an endoscope that includes the image capture device 101C to the mechanical arm. Conversely, the endoscope with image capture device 101C may include physical contours and/or structures complementary to those of the mechanical surgical arm 158C so as to securely interfit with them.

A user or operator O (generally a surgeon) performs a minimally invasive surgical procedure on patient P by manipulating control input devices 160 at a master control console 150. The operator can view video frames of images of a surgical site inside a patient's body through a stereo display device 164, which includes the viewer 312 described above with reference to FIG. 4. A computer 151 of the console 150 directs movement of teleoperated endoscopic surgical instruments 101A-101B via control lines 159, effecting movement of the instruments using a patient-side system 152 (also referred to as a patient-side cart).

The patient-side system 152 includes one or more teleoperated mechanical arms 158. Typically, the patient-side system 152 includes at least three mechanical surgical arms 158A-158C (generally referred to as mechanical surgical arms 158) supported by corresponding positioning set-up arms 156. The central mechanical surgical arm 158C may support an endoscopic camera 101C suitable for capture of Q3D information for images within a field of view of the camera. The mechanical surgical arms 158A and 158B to the left and right of center may support instruments 101A and 101B, respectively, which may manipulate tissue.

FIG. 6 is an illustrative perspective view of the patient-side system 152 in accordance with some embodiments. The patient-side system 152 comprises a cart column 170 supported by a base 172. One or more teleoperated mechanical manipulator surgical arms/links 158 are respectively attached to one or more set-up arms 156 that are a part of the positioning portion of the patient-side system 152. Situated approximately at a central location on base 172, the cart column 170 includes a protective cover 180 that protects components of a counterbalance subsystem and a braking subsystem from contaminants.

Excluding a monitor arm 154, each mechanical surgical arm 158 is used to control instruments 101A-101C. Moreover, each mechanical surgical arm 158 is coupled to a set-up arm 156 that is in turn coupled to a carriage housing 190 in one embodiment of the invention. The one or more mechanical surgical arms 158 are each supported by their respective set-up arm 156, as is illustrated in FIG. 6.

The mechanical surgical arms 158A-158D may each include one or more displacement transducers, orientational sensors, and/or positional sensors 185 to generate raw uncorrected kinematics information to assist in precise teleoperated control, as well as initial acquisition by a tracking system and tracking of instruments. The instruments may also include a displacement transducer, a positional sensor, and/or orientation sensor 186 in some embodiments of the invention. Moreover, one or more instruments may include a marker 189 to assist in acquisition and tracking of the instruments.

Additional information about a teleoperated medical system is provided in U.S. Pat. No. 5,631,973 (filed May 5, 1994), U.S. Pat. No. 5,696,837 (filed Apr. 20, 1995), U.S. Pat. No. 5,814,038 (filed Mar. 27, 1997), and U.S. Pat. No. 7,155,315 B2 (filed Dec. 12, 2005), and in U.S. Patent Application Pub. No. US 2012/0020547 A1 (filed Sep. 30, 2011).

Endoscopic Imager System

Figure 7A:
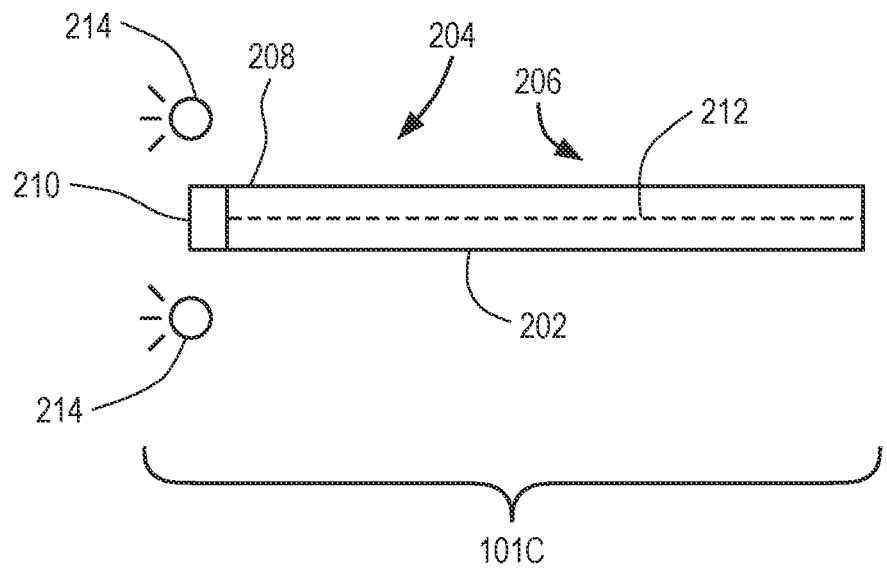
FIG. 7A is an illustrative drawing of a first endoscope that includes a first image capture system in accordance with some embodiments.

FIG. 7A is an illustrative drawing of a first endoscope with a first image capture system 101C in accordance with some embodiments. The image capture system 101C includes an endoscope that includes elongated portion 202, which includes a first end portion 204 and a second end portion 206 and a tip portion 208 of the first end portion 204. The first end portion 204 is dimensioned to be inserted into a human body cavity. A sensor array 210, which includes multiple image sensors (not shown), is coupled at the tip portion 208 of the first end portion 204. In accordance with some embodiments, each sensor in the sensor array 210 includes an array of pixels. The elongated portion 202 has a length sufficient to position the tip portion 208 close enough to a target object within the body cavity so that the object can be imaged by the imager sensor array 210. In accordance with some embodiments, the second end portion 206 may include physical contours and/or structures (not shown), as generally described above, so as to securely interfit with a mechanical arm (not shown). The elongated portion 202 also includes one or more electronic signal paths 212 to electronically communicate information with the imager sensor array 210. A light source 214 is disposed to illuminate the object to be imaged. In accordance with some embodiments, the light source 214 can be unstructured light, white light, color filtered light, or light at some selected wavelength, for example. In accordance with some embodiments the light source 214 is located at tip 208, and in other embodiments it is optionally located separately from endoscope 101C.

Figure 7B:
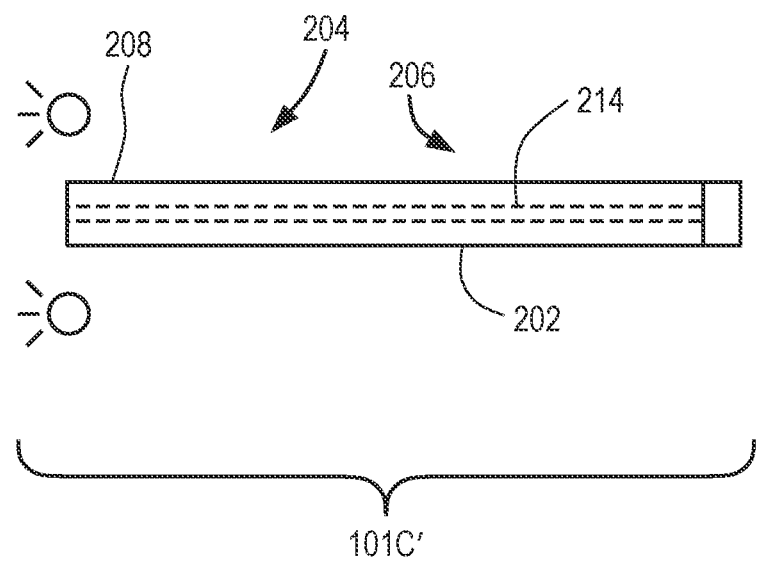
FIG. 7B is an illustrative drawing of a second endoscope that includes a second image capture system in accordance with some embodiments.

FIG. 7B is an illustrative drawing of a second endoscope with a second image capture system 101C2, in accordance with some embodiments. Aspects of the second image capture system 101C2 that are essentially the same as those of the first endoscope with the first image capture system 101C are indicated by identical reference numerals and are not described again. An input to a light pipe input, such as a rod lens, is disposed at the tip portion 208 of the first end portion 204. A light pipe body extends within the elongate portion 202 so as to transmit an image received as the light pipe input to the imager sensor array 210, which is physically displaced from the tip portion 208. In some embodiments, the imager sensor array 210 is displaced far enough from the tip portion 208 so that the imager sensor array 210 is located outside the body cavity during observation of objects within the cavity.

Figure 8:
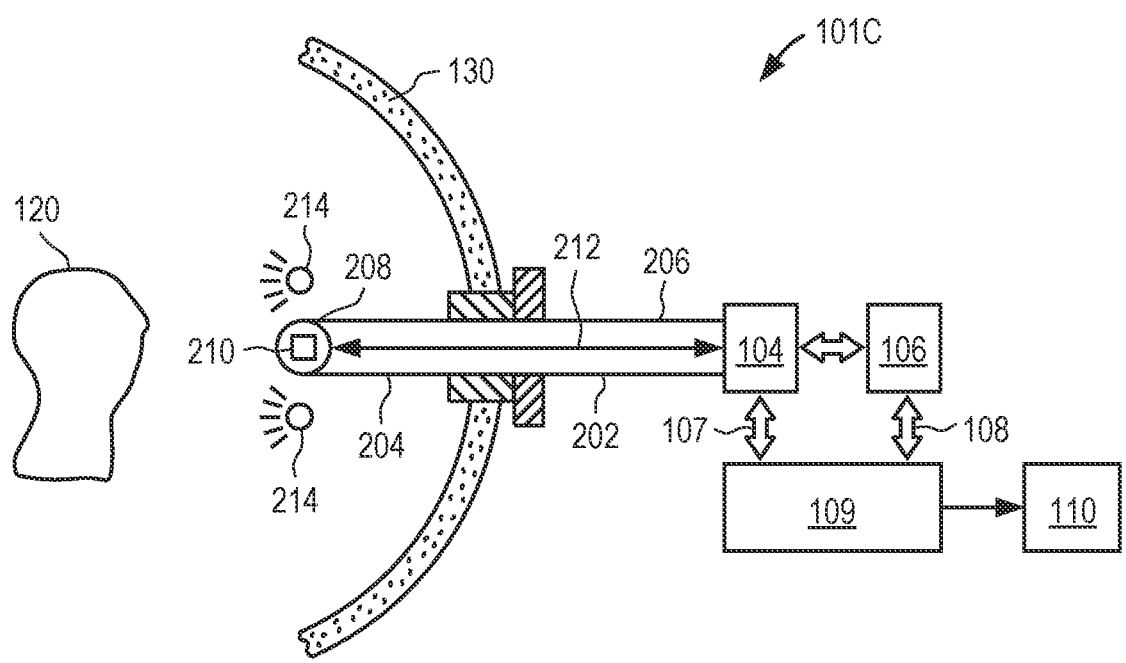
FIG. 8 is illustrative block diagram showing control blocks associated with the first endoscope that includes the first image capture system of FIG. 7A and showing the system in operation, in accordance with some embodiments.

FIG. 8 is illustrative block diagram showing control blocks associated with the first endoscope 101C with the first image capture system 101C of FIG. 7A and showing the system in operation, in accordance with some embodiments. Images captured by the imager sensor array 210 are sent over a data bus 212 to a video processor 104, which communicates via bus 105 with a controller 106. The video processor 104 may comprise a camera control unit (CCU) and a video signal detector (VSD) board. The CCU programs or controls various settings of the imaging sensor 210, such as brightness, color scheme, white balance, etc. The VSD processes the video signal received from the imaging sensor. Alternatively, the CCU and VSD are integrated into one functional block.

In accordance with some embodiments a processor system that includes one or more than one processor is configured to perform processor functions. In some embodiments the processor system includes multiple processors configured to operate together to perform the processor functions described herein. Thus, reference herein to at least one processor configured to perform one or more functions includes a processor system in which the functions may be performed by one processor alone or by multiple processors working together.

In one implementation, the controller 106, which includes a processor and a storage device (not shown), computes the physical quantitative 3D coordinates of the points in a scene adjacent the tip 208 of the elongate portion 202 and drives both the video processor 104 and a 3D display driver 109 to compose 3D scenes, which then can be displayed on a display 110, which can be a stereoscopic display or a volumetric (e.g., holographic) 3D display. In accordance with some embodiments. Q3D information about a surgical scene is generated, such as numerical indicia of dimensions of surface contours of objects in a scene or distances from objects within the surgical scene, for example. As explained more fully below, the numerical Q3D depth information can be used to annotate a stereoscopic image of a surgical scene with distance information or surface contour information.

Data buses 107 and 108 exchange information and control signals among the video processor 104, the controller 106, and the display driver 109. In some embodiments, these elements can be integrated with the image sensor array 210 inside the body of the endoscope. Alternatively, they can be distributed internally and/or externally to the endoscope. The endoscope is shown positioned, via a cannula 140, to penetrate body tissue 130 in order to provide visualize access to a surgical scene that includes a target 120. Alternatively, the endoscope and one or more instruments may also pass through a single opening—a single incision or natural orifice to reach a surgical site. The target 120 can be an anatomic target, another surgical instrument, or any other aspect of the surgical scene inside a patient's body.

An input system 112 receives the 3D visual representation and provide it to processor 106. The input system 112 may include a storage device coupled to an electronic communication bus (not show) that receives a 3D model such as a CRT or MRI from a system (not shown) that generates the 3D model. Processor 106, for example, can be used to compute the alignment intended between the Q3D model and the 3D visual representation. More particularly, without limitation, input system 112 may include a processor configured to establish an Ethernet communication connection between system 152 and an imaging system (not shown), such as a MRI, CT or ultrasound imaging system. Other imaging systems may be used. Other types of communication connections may be used, such as Bluetooth, WiFi, optical, etc. Alternatively, system 152 and the imaging system may be integrated in one larger system. The result of the alignment process may be saved in the storage device associated with processor 106, provided for further manipulation to external devices or system or displayed as shown in FIG. 25.

Example of Q3D Information Added to an Image of a Scene

Referring once again to FIG. 4 is an illustrative drawing showing a perspective view of a viewer 312 of the master control console 150 of FIG. 5 in accordance with some embodiments. In accordance with some embodiments, to provide a three-dimensional perspective, the viewer 312 includes stereo images for each eye. As shown, a left image 400L, and a right image 400R of the surgical site include any instruments 400 and a target 410 respectively in a left viewing element 401L and a right viewing element 401R. The images 400L and 400R in the viewing elements may be provided by a left display device 402L and a right display device 402R, respectively. The display devices 402L, 402R may optionally be pairs of cathode ray tube (CRT) monitors, liquid crystal displays (LCDs), or other type of image display devices (e.g., plasma, digital light projection, etc.). In the preferred embodiment of the invention, the images are provided in color by a pair of color display devices 402L, 402R, such as color CRTs or color LCDs. To support backward compatibility with existing devices, stereoscopic display devices 402L and 402R may be used with a Q3D system. Alternatively, the Q3D imaging system can be connected to 3D monitors, 3D TVs, or to autostereoscopic displays, such as a display that does not require use of 3D effect eye glasses.

A viewing system having two viewing elements 401R, 401L can provide a good 3D viewing perspective. The Q3D imaging system supplements this viewing perspective with physical dimension information for physical structures in the surgical scene. The stereo viewer 312 used in conjunction with a Q3D endoscopy system, can display Q3D information overlayed onto the stereo image of the surgical scene. Fax example, as shown in FIG. 4, the numerical Q3D distance value "d_instr_Trgt" between instrument 400 and target 410 can be displayed within stereo viewer 312.

An explanation of a video stereo viewing system that can be used to overlay physical location and dimension information onto a 3D perspective of a surgical scene is provided in U.S. Patent Application Pub. No. US 2012/0020547 (filed Sep. 30, 2011), paragraphs 0043-0053 and corresponding drawings, which is expressly incorporated herein by reference.

Processing Quantitative Three-Dimensional Physical Information

Figure 9:
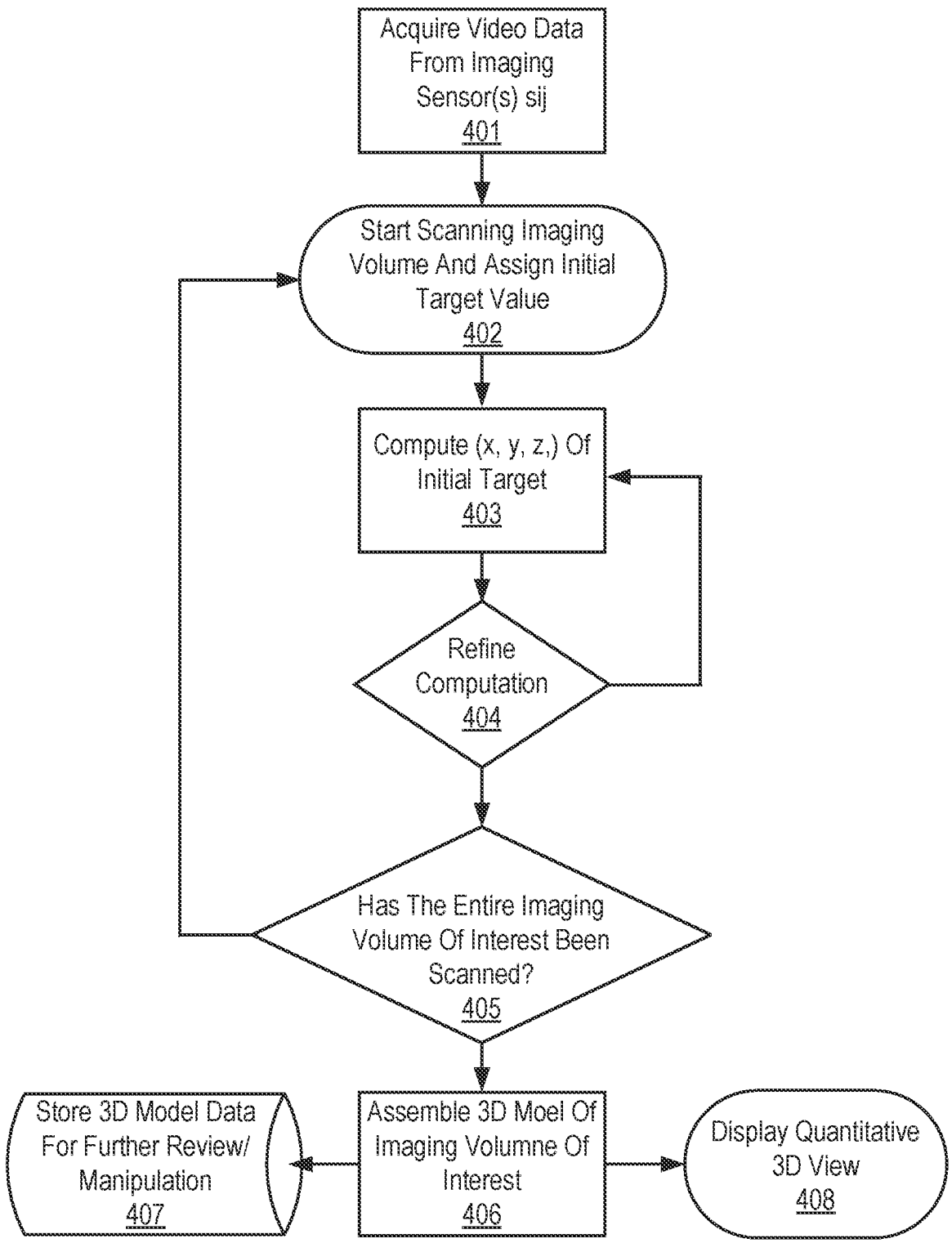
FIG. 9 is an illustrative flow diagram representing a process to determine a quantitative three-dimensional location of a physical target in accordance with some embodiments.

FIG. 9 is an illustrative flow diagram representing a process to determine a quantitative three-dimensional location of a physical target in accordance with some embodiments. The process is described with reference to the endoscope with image capture system 101C of the embodiment of FIG. 8. Module 401 configures the controller 106 to acquire video data from imaging sensors $S_{ij}$. It will be appreciated that although the image sensor array 210 "images" an entire field of view, different sensors and different pixels within different sensors in image sensor array 210 may be illuminated by image projections from different object points within the field of view. The video data, for example, may include color and light intensity data. Each pixel of each sensor may provide one or more signals indicative of the color and intensity of an image projected onto it. Module 402 configures the controller to systematically select targets from a selected region of interest in a physical world view. Module 403 configures the controller to continence the computation of the target 3D coordinates (x, y, z) with an initial $(x_0, y_0, z_0)$ set. The algorithm then checks the coordinates for consistency by using image diversity data from all sensors $S_{ij}$ that receive a projected image of the target. The coordinate computation is refined at decision module 404 until an acceptable accuracy is reached. Decision module 404 also configures the controller to determine whether the currently computed physical location is sufficiently accurate. In response to a determination that the currently computed location is not accurate enough, control flows back to module 403 to try a different possible physical location. In response to a determination that the currently computed location is sufficiently accurate, module 405 configures the controller to determine whether the entire region of interest has been scanned. In response to a determination that the entire region of interest has not been scanned, control flows back to module 402 and a different target is selected. In response to a determination that the entire region of interest has been scanned, control flows to module 406, which configures the controller to assemble a three-dimensional model of the imaging volume of interest. Assembly of a 3D image of a target based upon three-dimensional information indicating the physical position of structures of the target is known to persons of ordinary skill in the art and need not be described herein. Module 407 configures the controller to store the 3D model developed using the physical position information determined for multiple targets for further review and manipulation. For example, the 3D model could be used at a later time for surgical applications, such as sizing an implant for the particular dimensions of a patient's organ. In yet a different example, when a new surgical instrument 101 is installed on the robotic system 152, it may be necessary to call back the 3D model and display it on display 110 in order to reference the new instrument to the previous surgical scene. Module 407 may also store the result of the alignment between the 3D visual representation and the Q3D model. Module 408 configures the controller to use the physical position information determined for multiple targets to display a quantitative 3D view. An example of a Q3D view is the distance value "d_Instr_Trgt" shown in FIG. 4.

It is noted that a stereoscopic display creates the illusion of viewing in three dimensions. However, an actual 3D display presents a 3D image, such as a holographic image or an image projected onto a curved surface. Typically, a 3D display allows the view to move to change viewing perspective.

Figure 10:
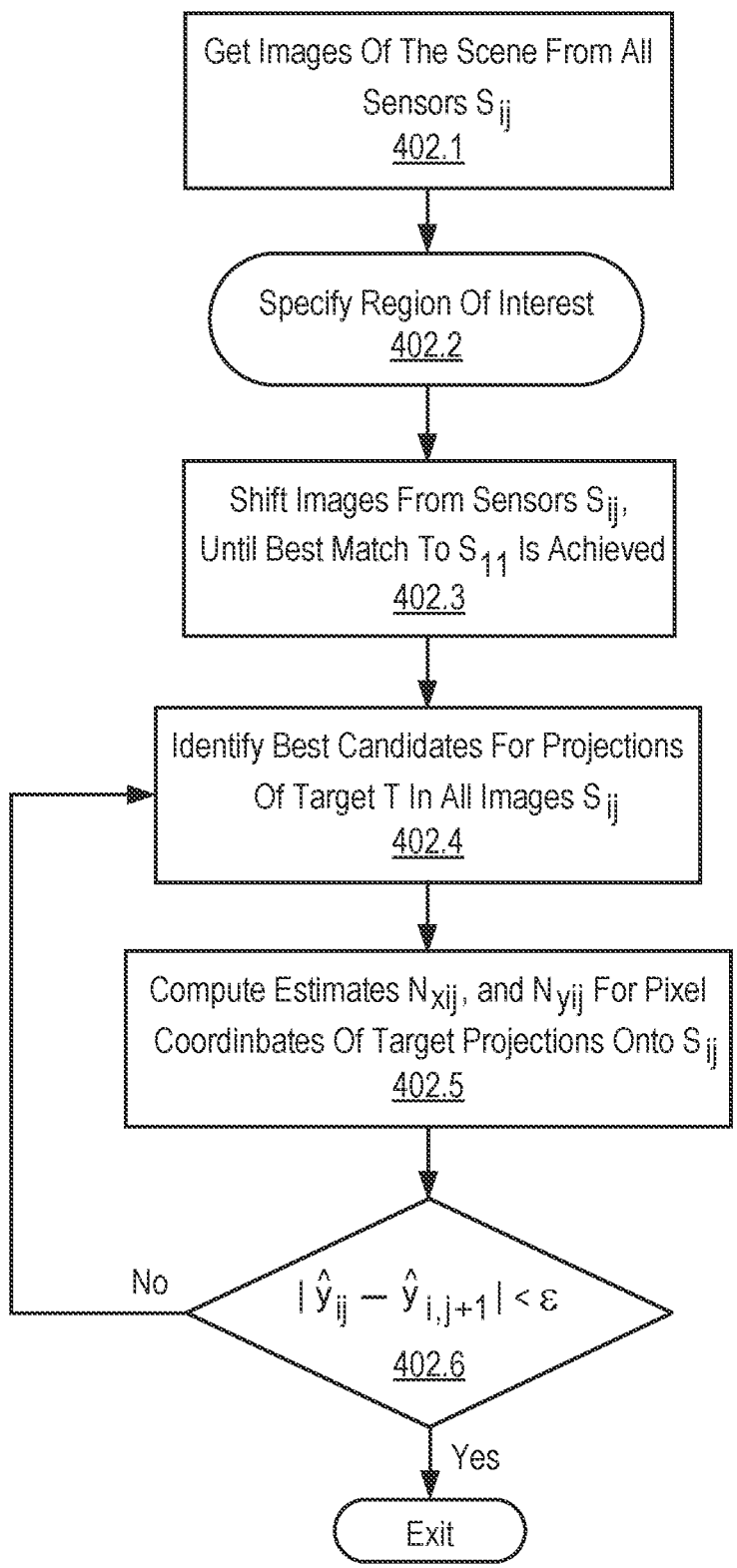
FIG. 10 is an illustrative flow diagram showing certain details of a process generally corresponding to module FIG. 9 to systematically select targets in accordance with some embodiments.

FIG. 10 is an illustrative flow diagram showing certain details of a process generally corresponding to module 402 of FIG. 9 in accordance with some embodiments. Module 402.1 configures the controller to capture images of a physical world scene from all sensors in the sensor array 210. Module 402.2 configures the controller to specify a region of interest from within the captured scene. Module 402.3 configures the controller to search for a best match as between scene images within the region of interest so as to identify pixel locations in different sensors that are illuminated by projections of the same target. As explained later, the best matching may be achieved, without limitation, by shifting the individual images from sensors $S_{ij}$ until maximizing two-dimensional cross-correlation function between the shifted image and a reference image. The reference image, for example, may be the scene image received from sensor Sit. Module 402.4 configures the controller to identify candidate pixels illuminated by projections from the same target. Module 402.5 configures the controller to compute two or more pixel coordinates ($N_x$, $N_y$) coordinates for the selected target to determine whether the candidate pixels are illuminated by a projection from the same target. Decision module 402.6 determines whether the computed 2D pixel coordinate values indicate that the candidate pixels are illuminated by a projection from the same target. The image diversity caused by viewing the same scene with multiple sensors $S_{ij}$ plays a role in correctly identifying ($N_x$, $N_y$) associated with a specific target in the various individual images. For example, in accordance with some embodiments, assuming a simplified scenario where only three sensors are used, $S_{11}$, $S_{12}$ and $S_{13}$, if the triplet of 2D pixel coordinates $[(Nx_{11}, Ny_{11}), (Nx_{12}, Ny_{12}), (Nx_{13}, Ny_{13})]$ are not corresponding to projections of the same target onto $[S_{11}, S_{12}$ and $S_{13})]$ then the quantities $\hat{y}_{12}$ and $\hat{y}_{13}$ (which are estimates of the projection shift in the y direction) will yield different values. According the equations presented later, $\hat{y}_{12}$ and $\hat{y}_{13}$ should be equal if pixel coordinates $(Nx_{11}, Ny_{11})$, $(Nx_{12}, Ny_{12})$, $(Nx_{13}, Ny_{13})$ come from projections of the same target.

$$\hat{y}_{12} = \frac{Ny_{11}}{Ny_{11} - Ny_{12}} \quad (402.5\text{-}1)$$

$$\hat{y}_{13} = 2 \cdot \frac{Ny_{11}}{Ny_{11} - Ny_{13}} \quad (402.5\text{-}2)$$

If $\hat{y}_{12}$ and $\hat{y}_{13}$ are not approximately equal then control flows back to module 402.4 and to refine the best candidates for target projections onto sensor planes $S_{ij}$. As mentioned, the above is just a simplified implementation of the algorithm. In general, as shown in FIG. 10 module 402.6, the norm of the difference between $\hat{y}_{i,j}$ and $\hat{y}_{i,j+1}$ should be less than an acceptable tolerance ε in order for module 402 to complete its iterations. A similar restriction should be met for the corresponding estimates for the x axis, $\hat{x}_{i,j}$ and $\hat{x}_{i,j+1}$. In response to a determination that the computed 2D pixel coordinate values ($N_x$, $N_y$) do indicate that the candidate pixels are illuminated by a projection from the same target, then control flows to module 403.

It will be appreciated that each pixel directly captures color and intensity information from a world scene. Moreover, in accordance with the above process, each pixel is associated with the (x, y, z) coordinates of the physical object in the world view that is projected onto the pixel. Thus, color information, illumination intensity information, and physical location information, i.e., the location of the physical object that projected the color and illumination, can be associated with a pixel in a non-transitory computer-readable storage device. The following Table 1 illustrates this association.

TABLE 1

| Pixel Identifier | Color Value | Illumination Value | Location (x, y, z) |
| --- | --- | --- | --- |

Examples of Determining Q3D Information
Example of Projection Matching

Figure 11:
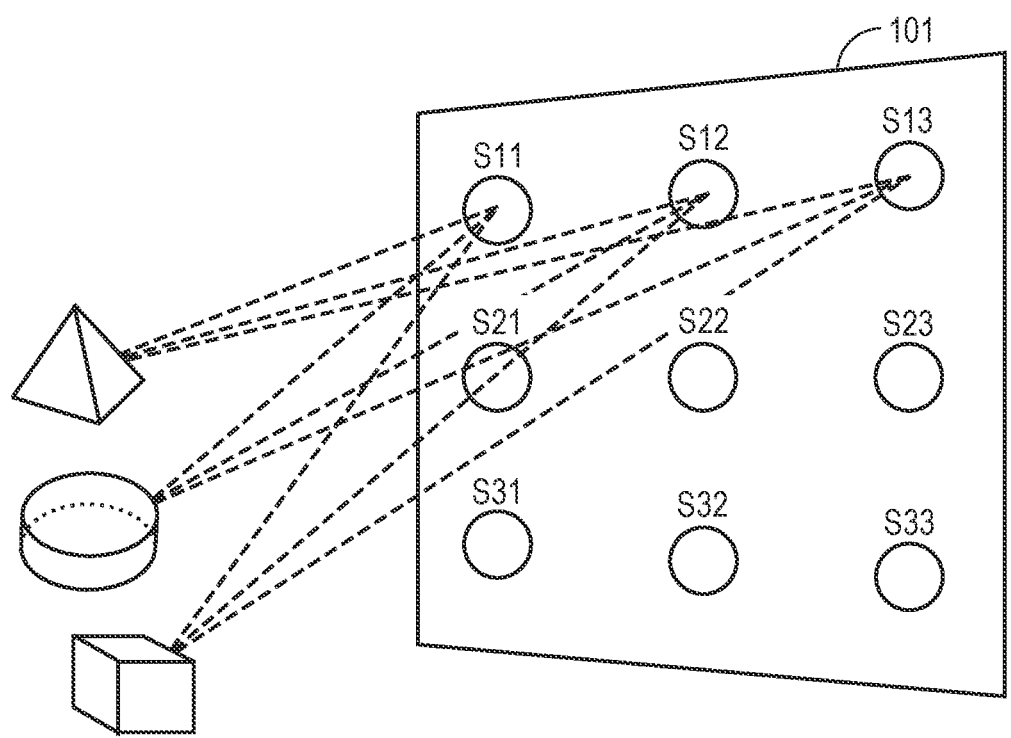
FIG. 11 is an illustrative drawing of an example sensor imager array that includes multiple sensors and that is disposed to have a field of view that encompasses an illustrative three dimensional physical world scene that includes three illustrative objects in accordance with some embodiments.

In accordance with some embodiments, FIG. 11 is an illustrative drawing of an example sensor array 210 that includes an array of sensors sensors $S_{11}$-$S_{33}$ that is disposed to have a field of view that encompasses an illustrative three-dimensional physical world scene that includes three illustrative objects. As described above, each sensor in the array includes a two-dimensional arrangement of pixels having at least two pixels in each dimension. Each sensor includes a lens stack that creates a separate optical channel that resolves an image onto a corresponding arrangement of pixels disposed in a focal plane of the lens stack. Each pixel acts as a light sensor, and each focal plane with its multiple pixels acts as an image sensor. Each sensor $S_{11}$-$S_{33}$ with its focal plane occupies a region of the sensor array different from regions of the sensor array occupied by other sensors and focal planes. Suitable known image sensor arrays are disclosed in U.S. Pat. No. 8,514,491 (filed Nov. 22, 2010) and in U.S. Patent Application Pub. No. US 2013/0070060 (filed. Sep. 19, 2012), which are described above.

In accordance with some embodiments, the sensors are characterized by a $N_x$ and $N_y$, their total number of pixels in the x and y directions, and by field of view angles, $\theta_x$ and $\theta_y$. In some embodiments, the sensor characteristics for the x and y axes are expected to be the same. However, in alternative embodiments, the sensors have asymmetric x and y axis characteristics. Similarly, in some embodiments, all sensors will have the same total number of pixels and the same field of view angle. The sensors are distributed across the sensor array 210 in a well-controlled manner. For example, the sensors may be at distance δ apart on the two-dimensional grid shown. The sensor placement pitch δ may be symmetric or asymmetric across such grid.

In the embodiment shown in FIG. 11, the sensors are arranged in a rectangular grid in which sensors $S_{11}$-$S_{13}$ occupy a top row, sensors $S_{21}$-$S_{23}$ occupy a middle row, and sensors $S_{31}$-$S_{33}$ occupy a bottom row. Each sensor includes N rows of pixels and N columns of pixels (not shown). Light rays produced by a light source are reflected from each of a triangular-shaped first object, a spherical-shaped second object, and a rectangular-shaped third object, to each sensor of the imager array as indicated by dashed lines. For illustration purposes, only rays to sensors $S_{11}$, $S_{12}$, and $S_{13}$ in the top row are shown. The light source may be non-structured white light or ambient light, for example. Alternatively, the light source may provide light at a selected wavelength, such as in the visible or infrared spectrums, or the light may be filtered or split to provide a selected wavelength (e.g., color) or range of wavelengths (e.g., range of colors), for example. It will be appreciated that light rays are similarly reflected from each of the objects to sensors $S_{21}$-$S_{33}$. However, in order to simplify the explanation, these other light rays are not shown. Further, it should be understood that in some implementations the light incident on the sensors originates at the objects, such as during fluorescence excited by an energy source, and the description of reflected light encompasses this situation.

Figure 12:
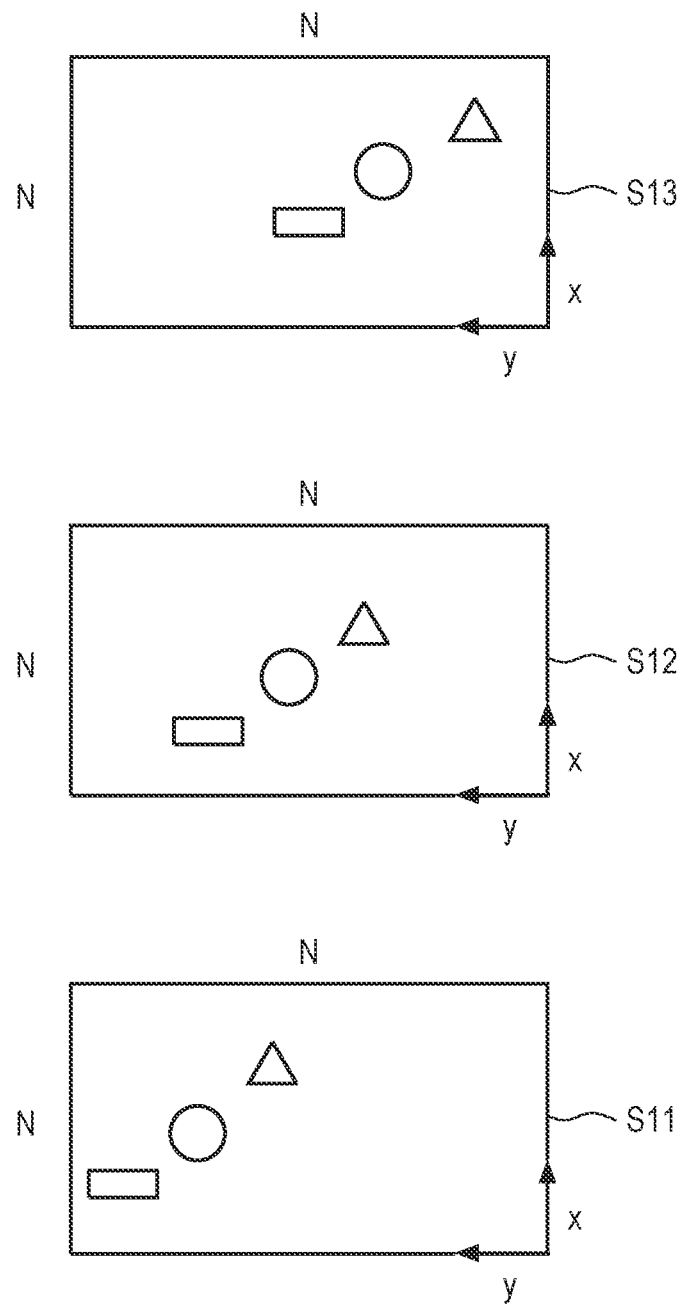
FIG. 12 is an illustrative drawing representing projections of the multiple physical objects of FIG. 11 onto multiple sensors in accordance with some embodiments.

In accordance with modules 401 and 402.1, sensors of the sensor array 210 separately capture images from a world view. FIG. 12 is an illustrative drawing representing projections of the three objects of FIG. 11 onto the sensors $S_{ij}$ (only $S_{11}$, $S_{12}$, and $S_{13}$ are shown) in accordance with some embodiments. A person of ordinary skill in the art will appreciate that the reflected light rays incident upon the sensors project images of the objects that are in the field of view. More specifically, the rays of light reflected from the objects in the field of view that are incident upon multiple different image sensors of the imager array produce multiple perspective projections of the objects from three dimensions to two dimensions, i.e., a different projection in each sensor that receives the reflected rays. In particular, the relative location of projections of the objects is shifted from left to right when progressing from $S_{11}$ to $S_{12}$ to $S_{13}$. Image sensor pixels that are illuminated by incident light rays produce electrical signals in response to the incident light. Accordingly, for each image sensor, a pattern of electrical signals is produced by its pixels in response to the reflected rays that indicates the shape and location of the image projection within that image sensor.

Figure 13:
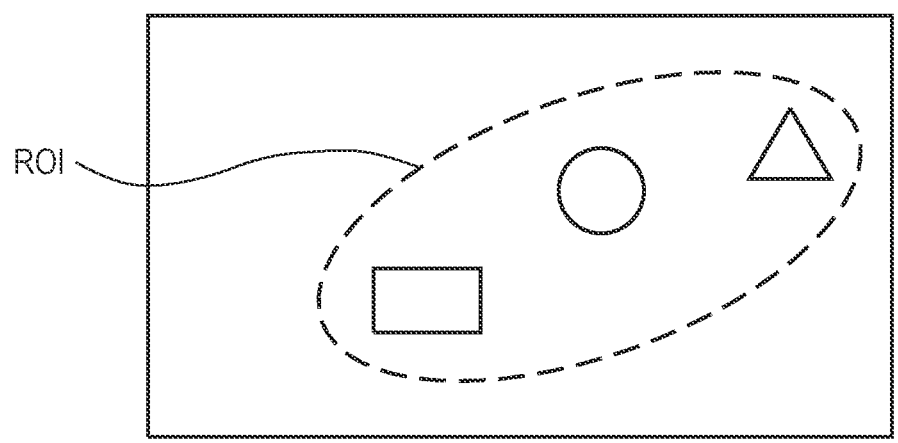
FIG. 13 is an illustrative drawing indicating selection of a region of interest from within a real-world scene in accordance with some embodiments.

In accordance with module 402.2, a region of interest is selected from the world scene. FIG. 13 is an illustrative drawing indicating selection of a region of interest (ROI) from within the scene. In this example, the triangular-shaped first object, spherical-shaped second object, and rectangular-shaped third object all are in the selected region of interest. This step can be achieved by accepting input from an operator, or it can be automatically performed using a computer configured by software in a prescribed manner, or by combination of operator inputs and automatic software-controlled selection. For example, in some embodiments, the world scene may show an internal cavity of the human anatomy, and the objects may be internal body organs, or surgical instruments, or portions thereof. A surgeon may receive real time visual imagery from within the internal cavity and may see tissue regions of the human anatomy and a portion of the surgical instruments projecting within the body cavity. The surgeon may specify those objects within the field of view fir which location information is to be determined through well-known techniques, such as a telestration video marker (see e.g., U.S. Pat. No. 7,907,166 B2 (filed Dec. 30, 2005)). Alternatively or in addition to such operator request, an automated process such as an edge detection algorithm can be used to specify a region of interest.

Figure 14:
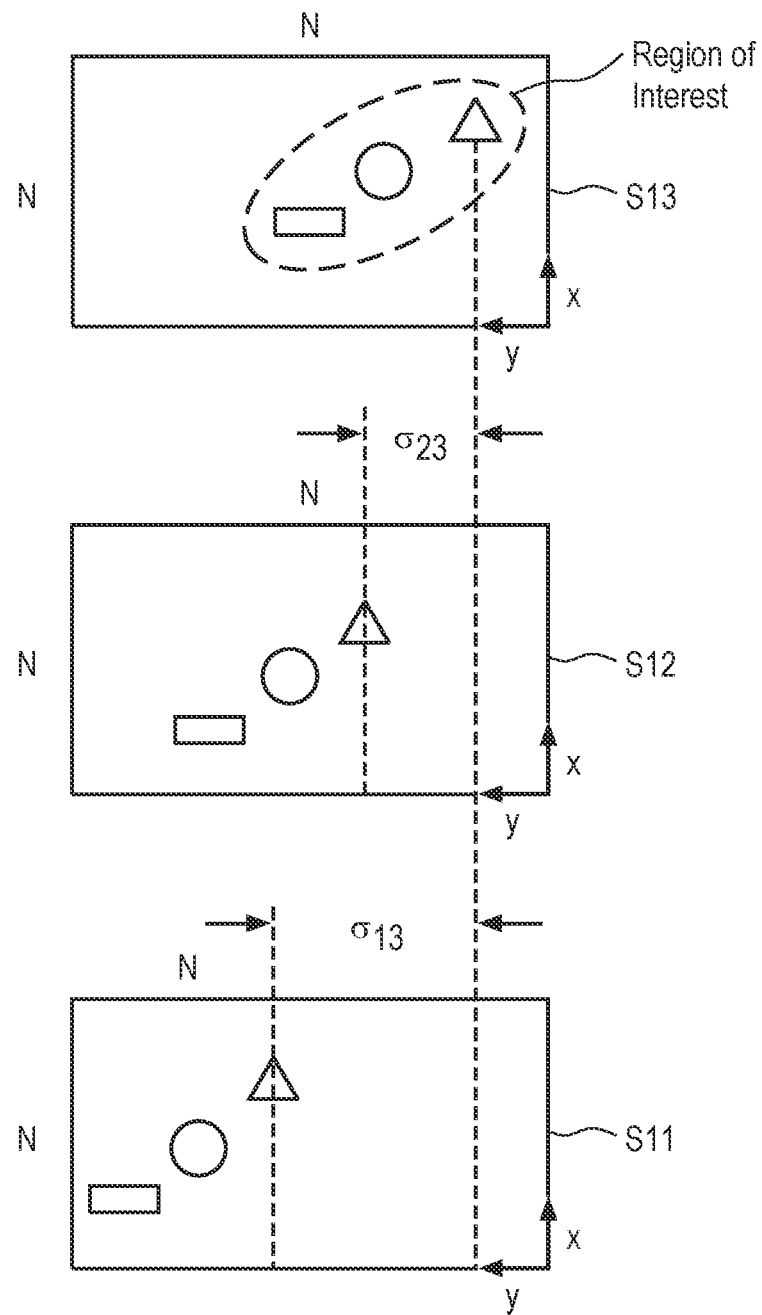
FIG. 14 is an illustrative drawing showing detail as to relative geometric offset of the projected images in sensors multiple sensors in accordance with some embodiments.

In accordance with module 402.3, a best match is determined between scene images within the region of interest so as to identify pixel locations in different sensors that are illuminated by projections of the same target object. FIG. 14 is an illustrative drawing showing additional detail about relative geometric offset of the projected images in sensors $S_{11}$, $S_{12}$, and $S_{13}$ in accordance with some embodiments. In accordance with some embodiments, an image from sensor $S_{13}$ is considered to be reference image, and the projections of the objects in the selected ROI are offset to the right by an amount $\sigma_{23}$ pixels in sensor $S_{12}$ relative to their location in sensor $S_{13}$. Similarly, the projections of the objects in the selected ROI are offset to the right by an amount $\sigma_{13}$ pixels in sensor $S_{11}$ relative to their location in sensor $S_{13}$. It will be appreciated that since the FOV viewing axes of sensors $S_{12}$, $S_{11}$ are each offset to the right of the FOV viewing axis of sensor $S_{13}$ (such viewing axes being perpendicular to plane of the sensors), the projected images from ROI are offset to the left in the sensors $S_{13}$ and $S_{11}$ relative to sensor $S_{11}$.

Figure 15:
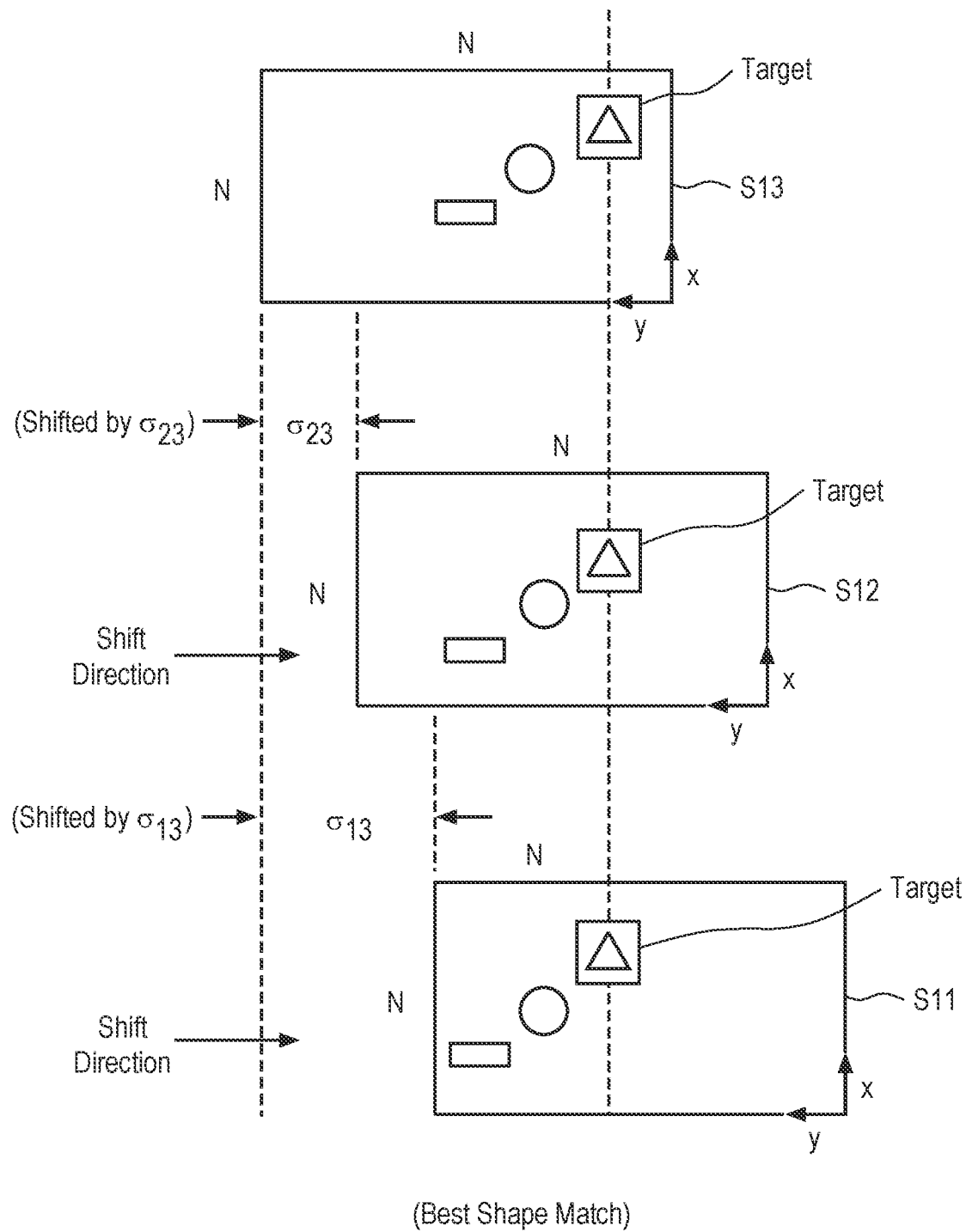
FIG. 15 is an illustrative drawing showing the projected images in certain example sensors within the region of interest (ROI) shifted to the right to align with the projected images in a designated reference sensor within the ROI in accordance with some embodiments.

FIG. 15 is an illustrative drawing showing the projected images in sensors $S_{11}$ and $S_{12}$ within the ROI shifted to the right to align with the projected images in sensor $S_{13}$ within the ROI in accordance with some embodiments. In the current example, sensor $S_{13}$ is designated to act as a reference sensor. It will be appreciated that other sensors can be chosen for use in determining alignment and geometric dimensions. Projections of the objects within the selected ROI are identified in the designated sensor, e.g., sensor $S_{13}$, and projections in the other sensors, e.g., in sensors $S_{11}$ and $S_{12}$, are shifted until they align with the projection in the designated sensor. In this manner, the corresponding projections of objects within the selected ROI can be identified within the other sensors, together with their offsets relative to the location of the projections in the designated sensor.

In particular, for example, the projections of the three example objects are shifted to the right by an amount $\sigma_{23}$ pixels in sensor $S_{12}$, and the projections of the three example objects are shifted to the right by an amount $\sigma_{13}$ pixels in sensor $S_{13}$. In this illustrative example, in order to simplify the explanation, it is assumed that the projections are offset in the y direction only and not in the x direction, although the same principles apply for x direction projection offsets as between sensors. Moreover, although this example shows a linear offsets, a person of ordinary skill in the art can apply other transformations such as rotation, for example, to align projections that have relative offsets in different sensors.

In accordance with some embodiments for example, two-dimensional (2D) cross-correlation techniques or principal component analysis (PCA), can be used to align the projections within the ROI in $S_{13}$ with the projections within the ROI in $S_{12}$ and to align the projections within the ROI in $S_{13}$ with the projections within the ROI in $S_{11}$. In general, the intent is to best match or align the images from sensors $S_{ij}$ with respect to the image from the sensor designated as reference. More specifically, the projected images within the ROI in $S_{12}$ are shifted and cross-correlated with the projected images within the ROI in $S_{13}$ until a highest correlation coefficient is achieved. Likewise, the projected images within the ROI in $S_{11}$ are shifted and cross-correlated with the projected images within the ROI in $S_{13}$ until a highest correlation coefficient is achieved. Thus, alignment of the projections of the ROI is used to identify the locations of the projections of the ROI in sensors $S_{11}$ and $S_{12}$ by determining the offset between the projection of the ROI in $S_{13}$ and the projection of the ROI in $S_{12}$ and by determining the offset between the projection of the ROI in $S_{13}$ and the projection of the ROI in $S_{11}$.

Example of Candidate Pixel Selection and Refinement

In accordance with module 402.4, candidate pixels are identified within different sensors, which according to the best match process, are illuminated by projections from the same target. Once the projections of objects within the ROI have been identified in each of the sensors $S_{11}$, $S_{12}$, and $S_{13}$, the physical (x, y, z) projections of individual target points within the ROI can be determined relative to the imager array. In accordance with some embodiments, for each of a multiplicity of target points within the ROI, one or more pixels within each of multiple sensors are identified that is illuminated by a projection from the target point. For each such target point, a physical (x, y, z) target point location is determined based at least in part upon the geometric relationships among pixels disposed in different sensors that are determined to be illuminated by projections from the target point.

It will be appreciated that a sequence of target points can be chosen automatically by systematically traversing the ROI (e.g., right to left with a certain step size and up to down with a certain step size), and a physical (x, y, z) target point location can be determined for each selected target point. Since $S_{11}$ and $S_{12}$ are best matched to $S_{13}$, the traversing is performed inside the shifted regions of interest. Selecting a target involves identifying a pixel in each of sensors $S_{11}$, $S_{12}$, and $S_{13}$ that is illuminated by a projection of the target. Thus, candidate pixels in each of $S_{11}$, $S_{12}$, and $S_{13}$ are identified as being the ones illuminated by a projection of the selected target point.

In other words, in order to select a target point T, a pixel is selected in each of the sensors $S_{11}$, $S_{12}$, and $S_{13}$ that is illuminated by a projection of the target point T. It will be appreciated that the (x, y, z) physical location of the target T is unknown at the moment of its selection. Moreover, it will be appreciated that inaccuracy of the above-described alignment process can result in inaccuracy in the determination of which pixels in each sensor are illuminated by the projection of a selected target T. Thus, as explained with reference to FIGS. 17, 18, and 19, a further determination is made as to the accuracy of the determination as to the pixels in each of $S_{11}$, $S_{12}$, and $S_{13}$ that are illuminated by the projection of a currently selected target T.

Continuing with the above example, assume that the triangular-shaped first object is the currently selected target point. FIG. 16 is an illustrative drawing showing projections of the selected triangle shaped target point onto sensors $S_{11}$, $S_{12}$, and $S_{13}$ in accordance with some embodiments. From these projections, the 2D pixel coordinates for target T are determined. $[(Nx_{11}, Ny_{11}), (Nx_{12}, Ny_{12}), (Nx_{13}, Ny_{13})]$. For simplification, FIG. 16 shows only the y-axis pixel coordinates. Using these 2D pixel coordinates, expressions (402.5-1) and (402.5-2) are applied and $\hat{y}_{12}$ and $\hat{y}_{13}$ computed as part of module 402.5. As part of module 402.6, the norm $|\hat{y}_{12}-\hat{y}_{13}|$ is computed and compared to the acceptable tolerance $\varepsilon$. Similarly, the x-axis pixel coordinates and location estimates are computed and compared against acceptable tolerances. If the condition of module 402.6 is met, then the process proceeds to module 403. Else, it returns to module 402.4 to further refine target candidates.

Figure 17:
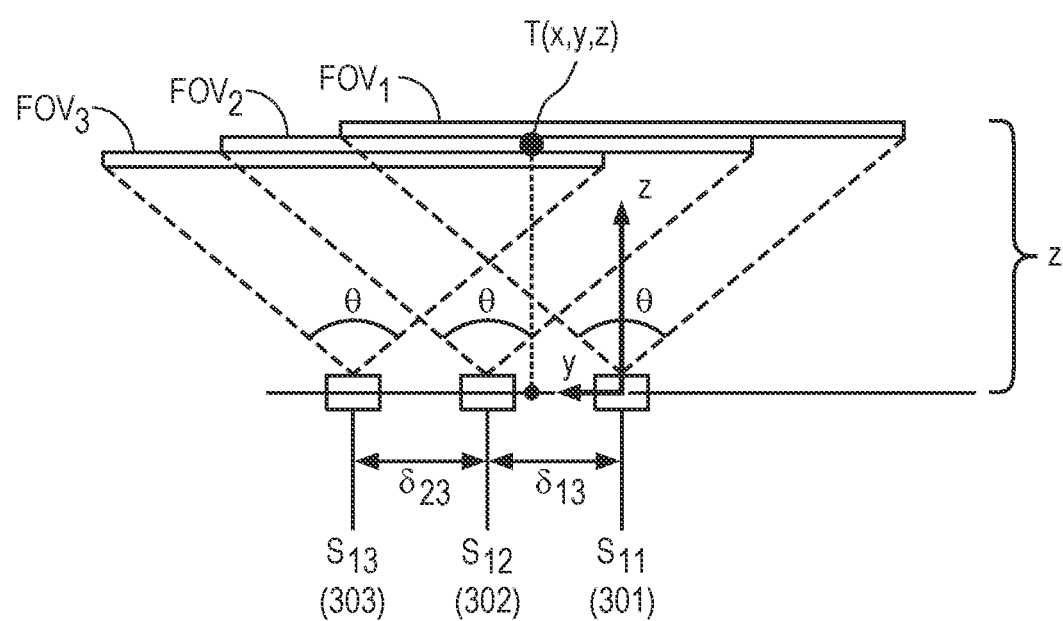
FIG. 17 is an illustrative drawing showing a portion of an imager array that includes the multiple sensors of FIG. 16 and the selected target point T disposed at location in physical space in accordance with some embodiments.

Referring to FIG. 17, there is shown a portion of an imager array that includes sensors $S_{11}$, $S_{12}$, and $S_{13}$ and the selected triangular-shaped first object target point T disposed at location (x, y, z) in physical space. Sensors within an imager array have a known spacing between them. The physical position spacing between $S_{11}$ and $S_{12}$ is $S_{12}$, and the physical position spacing between $S_{12}$ and $S_{13}$ is $\delta_{23}$. In some embodiments the spacing between all sensors is identical, equal to $\delta$, a constructional specification. Sensors $S_{ij}$ also have a known field of view angle $\theta$.

As explained above, in some embodiments, each sensor is constructed as a 2D imaging element with pixels arranged in a rectangular pattern of rows and columns. Alternatively, pixels can be arranged in a circular pattern, zigzagged pattern, scattered pattern, or an irregular pattern including sub-pixel offsets, for example. The angle and the pixel characteristics of these elements may be identical or, alternatively, may be different from sensor to sensor. However, these characteristics are assumed to be known. In order to simplify the explanation, it is assumed that the sensors are identical, although they may, however, be different.

For simplicity, let us assume that all sensors $S_{ij}$ have N×N pixels. At a distance z from sensor $S_{11}$, the N-pixel width of the sensor expands out to a y-dimension field of view of $S_{11}$ indicated by $FOV_1$. Likewise, at a distance z from sensor $S_{12}$, the y-dimension field of view of sensor $S_{12}$ is indicated by $FOV_2$. Also, at a distance z from sensor $S_{13}$, the y-dimension field of view of sensor $S_{13}$ is indicated by length $FOV_3$. The lengths $FOV_1$, $FOV_2$, and $FOV_3$ overlap each other, signifying that sensors $S_{11}$, $S_{12}$, and $S_{13}$ achieve a 3-way sampling diversity of target T physically located at some (unknown) distance z. Of course, if the sensors are identically built, as assumed in this example, length $FOV_1$, $FOV_2$, and $FOV_3$ will be identical as well. It will be appreciated that the three lengths $FOV_1$, $FOV_2$, and $FOV_3$ all have the same magnitude and are coplanar in that they are at the same (unknown) z-distance from the imager array, although for the purpose of illustration they are portrayed as if they were stacked adjacent to each other.

Referring to FIG. 18, there is shown an illustrative elevation view of the projection of the currently selected target point T onto the image sensors $S_{12}$, and $S_{13}$. For the sake of simplicity, it is assumed that the sensors include geometrically rectangular pixel arrays of size N×N pixels. It is also assumed that the x coordinates of the target T projections are all equal. In other words, it is assumed that for the projections of target T onto $S_{11}$, $S_{12}$, and $S_{13}$, $n_{x1}=n_{x2}=n_{x3}$. To simplify the explanation, it is also assumed that the geometric field of view angle θ is the same horizontally as it is vertically, $\theta_x=\theta_y$. A person of skill in the art would know how to modify the process presented below so that to compute the x, y, and z physical coordinates of target T if any of the above assumptions would change.

An image of the target T is projected to a physical point within sensor $S_{11}$ at geometric coordinates $(n_{x1}, n_{y1})$, in the plane of the image sensor $S_{11}$. More specifically, the projection of target point T onto sensor $S_{11}$ is located $n_{y1}$ pixels along the y axis, and $n_{x1}$ pixel along the x axis, taken from the origin. An image of the target T is projected to a physical point within sensor $S_{12}$ at geometric coordinates $(n_{x2}, n_{y2})$ in the plane of the image sensor $S_{12}$. An image of the target T is projected to a physical point within sensor $S_{13}$ at geometric coordinates $(n_{x3}, n_{y3})$ in the plane of the image sensor $S_{13}$. It will be appreciated that pixel locations $n_{x1}, n_{y1}$) within each sensor are determined relative to origin (0, 0) reference coordinates provided for the sensor. As shown in FIG. 17 or FIG. 19, a global system of coordinates (x, y, z) is defined and used to reference the target. For example, the origin of such system of coordinates may be placed, without limitations, at the geometrical center of sensor $S_{11}$.

Referring to both FIG. 16 and FIG. 18, it can be seen that the y pixel distance of the projection of the target is different in each sensor. The projection of a currently selected target T is disposed $n_{y1}$ pixels to the left of the origin in $S_{11}$. The projection of the selected target T is disposed $n_{y2}$ pixels to the left of the origin in $S_{12}$. The projection of the selected target T is disposed $n_{y3}$ pixels to the left of the origin in $S_{13}$. As mentioned above, to simplify the explanation, it is assumed that the projection of the target falls at the same x pixel distance from the origin in all three sensors.

Referring to FIG. 19, there is shown the disposition of the currently selected target T relative to sensors $S_{11}$, $S_{12}$, and $S_{13}$ as described above with reference to FIG. 17 and also showing y-direction pixel offsets for the candidate pixel in each of the sensors. It will be understood that the drawings of FIG. 19 present physical structures and an analytical framework for determining the (x, y, z) physical coordinates of the selected target point T. At an (unknown) distance z from the imager array plane, the y-direction field of view for each sensor extends over a length marked as $FOV_i$. This length, $FOV_i$, corresponds to the maximum pixel width of the sensor, which is N pixels, in some embodiments. Given that the working assumption was that the sensor has a field of view that is symmetric in the x and y directions, the length would also be $FOV_i$ vertically, along the x axis.

Recall that the candidate pixel selections are made based at least in part upon a correlation process that can have a level of uncertainty than can result in inaccuracy in determination of the physical location of the selected target. Thus, a further check of the accuracy of the target projection candidate selections, in accordance with some embodiments, is made as follows.

Example of Determining Target's Physical (x, y) Location and Checking Accuracy of Target Projection Candidate Selection In accordance with module 402.5, two or more two-dimensional ($N_x$, $N_y$) coordinate values are computed for the selected target to determine whether the candidate pixels actually are illuminated by a projection from the same target. Based on the assumptions discussed above and placing the origin of the 3D system of coordinates at the center of sensor $S_{11}$, the imager array and currently selected target T in the example in FIG. 19 have the following relationships:

$$z = \frac{N \cdot \delta}{2 \cdot (n_{y1} - n_{y2}) \cdot \tan\left(\frac{\theta}{2}\right)} \quad (1)$$

$$y = \frac{2n_{y1} - N}{2(n_{y1} - n_{y2})} \cdot \delta \quad (2)$$

$$x = \left(\frac{2n_{x1}}{N} - 1\right) \cdot z \cdot \tan\left(\frac{\theta}{2}\right) \quad (3)$$

Where:
N is the pixel dimension of the imaging sensors;
$n_{x1}$ is the position of a target point T expressed in number of pixels from the origin of the $S_{11}$ plane in the x direction;
$n_{y1}$ is the position of the target point T expressed in number of pixels from the origin of the $S_{11}$ plane in they direction;
$n_{y2}$ is the position of the target point T expressed in number of pixels from the origin of the $S_{12}$ plane in they direction; and
$n_{y2}$ is the position of the target point T expressed in number of pixels from the origin of the $S_{12}$ plane in they direction;
θ is the angle of the field of view.
Moreover, if performing the same math using sensors $S_{11}$ and $S_{13}$ and given that the separation between $S_{11}$ and $S_{13}$ is 2δ, we obtain:

$$z = \frac{2 \cdot N \cdot \delta}{2 \cdot (n_{y1} - n_{y3}) \cdot \tan\left(\frac{\theta}{2}\right)} \quad (4)$$

$$y = \frac{2n_{y1} - N}{2(n_{y1} - n_{y3})} \cdot 2\delta \quad (5)$$

$$x = \left(\frac{2n_{x3}}{N} - 1\right) \cdot z \cdot \tan\left(\frac{\theta}{2}\right) + 2\delta \quad (6)$$

Where:

$n_{x3}$ is the position of a target point T expressed in number of pixels from the origin of the $S_{13}$ plane in the x direction; and $n_{y3}$ is the position of the target point T expressed in number of pixels from the origin of the $S_{13}$ plane in the y direction.

Thus, determination of the physical x coordinate of the selected target T can be determined based upon expressions (3) or (6). A determination of the physical y coordinate of the selected target T can be determined based upon expressions (2) or (5). A determination of the physical z coordinate of the selected target T can be determined based upon equations (1) or (4).

More generally, in accordance with module 402.6, a determination is made as to whether the computed 2D coordinate values indicate that the candidate pixels are illuminated by a projection from the same target. It will be appreciated that a more reliable determination of the physical (x, y, z) coordinates of the target T can be obtained through the use of two formulations for each coordinate. For example, the y coordinate for the target T can be determined using both formulations (2) and (5). If the resulting y coordinate values computed using the two formulations differ by more than some acceptable tolerance value then a determination can be made that the matching process failed to resolve the offset between projections in the different sensors with sufficient accuracy, and as result that the candidate pixels do not correspond in that they do not receive projections from the same target T. In the event of a failure of the y computations to match, another iteration of the matching process may be performed in an effort to make an improved selection of candidate pixels within the sensors that each corresponds to a selected target T. It will be appreciated that the computed y values are unlikely to be equal since the different perspective projections onto different sensors can differ due to parallax effects, for example. Therefore, an acceptable tolerance value is prescribed according to the intended application. For surgical imaging applications, an ε of 0.1-0.3 mm typically offers an acceptable Q3D accuracy. A person of skill in the art may define different acceptable tolerance levels without departing from the spirit of this invention.

Given the assumed sensor symmetry around the x and y axes, persons skilled in the art will appreciate that the same kind of determination can be made for the x coordinates of the target T using formulations similar to those in (2) and (5), but using rixt instead of $n_{yt}$. Formulations (3) and (6) cannot be used part of 402.5 and 402.6 because they require knowledge of the z coordinate. However, the essence of modules 402.5 and 402.6 is to determine the correct target projections on the planes of sensors $S_{11}$, $S_{12}$, and $S_{13}$. For this purpose, formulations (2) and (5), adjusted for x and y axes, are sufficient. The complete set of coordinates (x, y, z) is computed part of modules 403 and 404, as described below.

Example of Determining Target's Physical z Location

As illustrated in FIG. 19, in accordance with modules 403 and 404, an initial estimate for the z coordinate $z_0$ is used to initiate the computation process. This initial value is defined automatically, according to the medical application. The medical application defines the intended world view to be visualized. The initial value $z_0$ starts at the edge of the field of view closest to the endoscope. Referring to FIG. 8, for a Q3D application involving surgical endoscopy, $z_0$ can be 1-5 mm off the distal end 208 of the Q3D endoscope 202, for example, Such initial estimate generally is sufficient for this application as it is unlikely to have any tissues or surgical instruments reside in such close proximity to the Q3D endoscope. Next, value $z_0$ is plugged into formulations (3) and (6). Given that the x coordinate of the target is unique, if $z_0$ were the true and correct z coordinate of the target, then formulations (3) and (6) would yield identical values, or approximately equal, within an acceptable level of tolerance, $\varepsilon_x$.

$$|x_{(3)} - x_{(6)}| < \varepsilon_x \quad (7)$$

If (3) and (6) are outside an acceptable tolerance $\varepsilon_x$, then the iteration continues and a new estimate $z_1$ for z is tried. In accordance with some embodiments, the new estimate is defined automatically. For example, $z_1 = z_0 \Delta$, where $\Delta$ is the size of the iteration step. In general, at $k^{th}$ iteration $z_k = z_{k-1} + \Delta$. The iterative process stops when condition (7) is met. A smaller $\Delta$ yields increased accuracy in determining the correct target coordinates, but it would also require more computational time to complete the process, hence an increased latency. An increased latency may result in delays between surgical instrument movement and its visualization by the operating surgeon. In other words, the surgeon may perceive the system as lagging behind commands (i.e., not operating in real time). For a surgical viewing space of 20-30 cm of depth, a $\Delta$ of 0.1-0.3 mm may be sufficient. Of course, a person skilled in the art would know to balance the size of $\Delta$ against the computational required to complete the iterative process.

The above explanation has been simplified for presentation reasons and, therefore, it included only three sensors, $S_{11}$, $S_{12}$, and $S_{13}$. In general, more sensors can be used to increase the accuracy of Q3D coordinate computations but also to reduce the overall number of iterations. For example, if more than three sensors are used, preferably an array of 3×3 sensors, then methods such as the steepest gradient may be employed to trend the direction of estimation errors made by modules 402.5 and 403. The iterative step size and direction can then be adjusted to match the progression towards the local extreme of the 3D error gradient surface.

Guiding Endoscopic Surgery with Q3D Information

FIG. 20 is an illustrative flow diagram representing a first process 2000 to use Q3D information during a surgical procedure in accordance with some embodiments. Computer program code configures the computer 151 to perform the process 2000. Module 2002 configures the computer to receive user input to select at least two objects within a surgeon's field of view when looking into the viewer 312. Module 2004 configures the computer to display a menu on a computer console in response to receipt of a user selection. Decision module 2006 configures the computer to determine whether user input to the menu is received to display a distance. In response to a determination that user input is received to display a distance, module 2008 configures the computer to display a numerical distance within the video image in the surgeon's field of view. Decision module 2010 configures the computer to wait for a prescribed time interval for receipt of user input to select distance display and to end operation of decision module 2006 in response to no receipt of user input within a "time out" interval.

Decision module 2012 configures the computer to determine whether user input to the menu is received to enter a proximity alarm limit. In response to a determination that user input is received to enter a proximity threshold, module 2014 configures the computer to use Q3D information to monitor proximity between two or more objects within the surgeon's field of view. Decision module 2016 determines whether the proximity threshold has been crossed. In response to a determination that the proximity threshold has been crossed, module 2018 configures the computer to activate an alarm. The alarm may include a sound, a visual queue such as a blinking light, locking of instrument movement to avoid collision, or other haptic feedback. In response to a determination that the proximity threshold has not been crossed, control flows back to monitoring module 2014. Decision module 2020 configures the computer to wait for the prescribed time interval for receipt of user input to enter the proximity threshold and to end operation of decision module 2012 in response to no receipt of user input within the "time out" interval.

FIG. 21 is an illustrative drawing showing menu selections displayed on a display screen 2102 in accordance with the process of FIG. 20 in 11) accordance with some embodiments. The display screen 2102 includes a viewing monitor associated with the computer 151. Alternatively, the display screen 2102 may include a region of the viewing elements 401R, 401L, of the viewer 312. In response to user input, module 2004 causes the display of a menu 2104 that includes a first menu item "Display Distance" 2106 and a second menu item "Set Proximity Alarm" 2108. In response to user input to select the "Display Distance" menu item 2106, module 2008 causes a display of Q3D distance between two or more objects. Referring again to FIG. 4, there is shown a display of a Q3D distance "d_Instr_Trgt" between an instrument 400 and target displayed using module 2008. In response to user input to select the "Set Proximity Alarm" menu item 2108, an "Enter Distance" UI input 2110 is displayed that includes a field in which a user can enter a proximity distance threshold value, e.g., one cm. In an alternative embodiment (not shown), a default proximity threshold may be set in advance for all instruments, and a user may change the proximity threshold using the menu of FIG. 21, for example. In the alternative embodiment, a user can choose to elect the default threshold value rather than enter a threshold value. In some embodiments, a user can select both to display the distance and set a proximity alert.

FIGS. 22A-22B are illustrative drawings representing certain details of receiving user input in accordance with the process of FIG. 20 in accordance with some embodiments. FIG. 22A shows example first highlighting areas 2202L, 2202R of a target 410L, 410R, such as body tissue, which can be created using video marker tool, such as telestration, or using the surgeon console manipulating control input devices 160 of FIG. 4. FIG. 22B shows example second highlighting areas 2206L, 2206R of an instrument tip 400L, 400R, which can be created using the video marker tool. In operation in accordance with some embodiments, a user creates the first highlighting areas 2202L, 2202R. Next, the user creates second highlighting areas 2206L, 2206R of the instrument tip 400L, 400R using video marker tool. It will be understood that the order in which items are highlighted is unimportant. The user then actuates a selector (not shown) (e.g., press the ENTER key) to enter the selection. Module 2002 interprets the received user input as selection of the target image 410L, 410R and the instrument image 400L, 400R.

FIG. 23 is an illustrative flow diagram representing a second process 2300 to use Q3D information during a surgical procedure in accordance with some embodiments. Computer program code configures the computer 151 to perform the process 2300. Module 2302 configures the computer to receive user input to select an object within a surgeon's field of view when looking in to the viewer 312. For example, referring again to FIG. 22A, user input is shown received to create the second highlighting areas 2206L, 2206R of the instrument tip 400L, 400R using the video marker tool. User input (not shown) is received to actuate a selector (not shown) (e.g., press the ENTER key) to enter the selection of the image of the instrument tip 400L, 400R.

Returning once again to FIG. 23, in response to receipt of a user selection, module 2304 configures the computer to display a menu on a computer console. Decision module 2306 configures the computer to determine whether user input to the menu is received to rotate an image of a selected object. In response to a determination that user input is received to rotate an image, module 2308 configures the computer to display rotate the image to show a different three-dimensional perspective of the object. Decision module 2310 configures the computer to wait for a prescribed time interval for receipt of user input to rotate an image and to end operation of decision module 2306 in response to no receipt of user input within a "time out" interval.

FIG. 24 is an illustrative drawing showing menu selections displayed on a display screen 2402 in accordance with the process of FIG. 23 in accordance with some embodiments. The display screen 2402 includes a viewing monitor associated with the computer 151. Alternatively, the display screen 2402 may include a region of the viewing elements 401R, 401L, of the viewer 312. In response to received user input, module 2304 causes the display of a menu 2404 that includes a third menu item "Rotate Left" 2406 and a fourth menu item "Rotate Right" 2408. In response to user input to select one or the other of the third or fourth menu items 2406, 2408, module 2308 uses the causes a rotation of the 3D model created and stored pursuant to module 407 of FIG. 9. It will be appreciated that the amount of rotation may be limited to a few degrees, less than 30 degrees for example, since the sensor imager array 210 has a limited overall field of view.

Virtual Q3D Perspective from an Instrument Tip

FIG. 25 is an illustrative drawing showing a perspective view of a Q3D endoscope 2502 associated with an image sensor array 210 and having an endoscope field of view (FOV$_e$). FIG. 25 also shows a perspective view of a portion of a surgical instrument 2506 and one or more anatomical structures 2508-1, 2508-2 disposed in a surgical scene 2508 within the field of view in accordance with some embodiments. A light source 2510 illuminates the surgical scene 2508. As explained with reference to FIGS. 7A-7B and FIGS. 8-10, an image sensor array 210 is positioned to capture image projections of the surgical instrument 2506 and the anatomical structures 2508-1, 2508-2 within the FOV$_e$ that expands from the tip 2512 of the endoscope 2502. As a result, a Q3D model of surgical scene 2508 is computed. As explained above with reference to FIG. 8, the endoscope 2502 penetrates body wall tissue via a cannula or enters the body through a natural orifice, and then it extends within a patient's body cavity in order to provide visual access to and capture images of the surgical scene 2508, which includes, as example targets, the surgical instrument 2406 and the anatomical structures 2508-1, 2508-2 inside the patient's body cavity.

FIG. 25 illustrates the field of view (FOV$_e$) of a Q3D endoscope 2502 deployed as described in reference to FIGS. 5-6 in accordance with some embodiments. As shown in FIGS. 5-6, instruments 101A-B and a Q3D endoscope 101C may be deployed through different cannulas during a surgical intervention. The surgical intervention may involve use of a teleoperated medical system, or it may be manual minimally-invasive intervention, or it may be an open surgery intervention, or a combination thereof. It will be appreciated that the endoscope field of view ($FOV_e$) is visible to a surgeon through a viewer 312, as described above with reference to FIG. 4, during a surgical procedure. FIG. 6 illustrates placement of endoscope 101C and instruments 101A-101B on the mechanical surgical arms 158A-158D of a patient side cart, in reference to a teleoperated surgical intervention that uses robotic technology.

For illustration purposes, a target surgical instrument 2506 is shown having an end effector in the form of a needle driver, such as the ENDOWRIST® Mega Needle Driver Instrument for the DA VINCI Si® Surgical System. However, alternate end effectors can be used to implement different surgical instrument functions during surgical interventions, such as scissors, grasper, scalpel, cautery electrode, stapler, or clip applier, for example. For illustration purposes, the example surgical scene 2508 within a patient's body cavity includes a first anatomic target 2508-1 that has a spherical shape that represents a first anatomical tissue structure, and a second anatomic target 2508-2 that has a pyramidal shape that represents a second anatomical tissue structure.

In accordance with some embodiments, a virtual Q3D perspective of the surgical scene 2508 is produced from a viewing perspective along longitudinal axis 2514 of the target surgical instrument 2506, which is disposed within the endoscope $FOV_e$ of the sensor array associated with the endoscope 2502. A determination is made as to transformations of orientation and position of the endoscope 2502 to align it with the axis 2514 of the target surgical instrument 2506. These orientation and position transformations are used as a basis for transformation of a Q3D rendering of the scene 2508 from a Q3D view within the $FOV_e$ of the endoscope 2502 to a Q3D view within an instrument field of view ($FOV_i$) along the axis 2514 of the surgical instrument 2506. The view of the surgical scene 2508 from the $FOV_i$ is may be visualized using the 3D viewer 312 of FIG. 4. Thus, the Q3D information is used to create still or moving images as if an image capture device was located at the tip of surgical instrument 2506 and having an $FOV_i$ aligned with the longitudinal axis of surgical instrument 2506 in a way similar to the way fields of view are aligned with dedicated endoscope instruments (e.g., 0° offset from the longitudinal axis, 30° offset from the longitudinal axis, etc.). Alternatively, the $FOV_i$ may be placed at another location on surgical instrument 2506, such as at or adjacent a fulcrum between jaws. Yet another way of describing this aspect is to consider endoscope 2502 and surgical instrument 2506 coincident with each other, so that an endoscopic image is generated from surgical instrument 2506's perspective.

FIG. 26 is an illustrative flow diagram representing a process 2600 to convert a Q3D scene from an endoscope viewing perspective to a Q3D scene from a perspective of a target instrument within the endoscope viewing perspective in accordance with some embodiments. In order to perform certain geometrical transformations in accordance with some embodiments, it is assumed that the Q3D endoscope tip 2512 is located at the origin of a 3D system of coordinates, x, y, z, as illustrated in FIG. 25. Module 2602 configures the computer 151 (or controller 106; references to computer 151 apply to controller 106 as well in the following descriptions) from FIG. 8, to create a Q3D model 2650 of the scene 2508. As explained above with reference to FIGS. 9-19, the computer 151 is configured to determine the (x, y, z) coordinates of points determined in the endoscope $FOV_e$. In doing so, the system creates a Q3D model 2650 of the scene 2508. The Q3D model 2650 is stored in a non-transitory computer-readable storage device 2652. As shown in FIG. 25, a distal portion of instrument 2506 is captured within the $FOV_e$ of the sensor 210 associated with the endoscope 2502.

Module 2604 configures the computer 151 from FIG. 8, to determine a distance $d_1$ between the tip 2512 of the endoscope 2502 and the scene 2508. Distance $d_1$ represents the length from tip 2512 to the closest point of scene 2508. In the example provided in FIG. 25, $d_1$ is distance from Q3D endoscope tip 2512 to the closest point on target 2508-1. Similarly, module 2604 configures the computer 151 to determine a distance $d_2$ between a tip 2516 of the target surgical instrument 2506 and the surgical scene 2508. Distance $d_2$ represents the length from tip 2516 to the closest point of scene 2508. In the example provided in FIG. 25, $d_2$ is distance from instrument tip 2516 to the closest point on target 2508-1. Distances $d_1$ and $d_2$ can be determined by the system based upon the details of the Q3D model. Distances $d_1$ and $d_2$ can be computed using algorithms described with reference to FIGS. 9 and 20. The algorithm described for FIG. 9 determines the coordinates of all points in $FOV_e$. The algorithm described for FIG. 20 can then be used to determine the distance between any two objects, such as between 2512 and 2508-1, or such as between 2516 and 2508-1. As explained more fully below, these distance parameters are used when the rendering of the 3D perspective is described.

Next, a series of geometric transformations are performed based upon information in the Q3D model of the scene 2508 to virtually "move" the Q3D endoscope 2502 so that it takes the 3D pose of instrument 2506. As used herein, the term "pose" refers to the position of an object or a portion of an object in at least one translational degree of freedom and to the orientation of that object or portion of the object in at least one rotational degree of freedom (up to the six total degrees of freedom in Cartesian space (i.e., surge, heave, sway, roll, yaw, pitch)). Although this description is in Cartesian terms, other coordinate systems (polar, cylindrical, spherical, etc.) may be used in practice.

Module 2606 configures the computer 151, or controller 106, to determine the (x, y, z) coordinates of at least two points located on a visible portion of the instrument 2506 from the Q3D model 2650. Preferably, for increased accuracy, more points can be determined. Assume, for example, that these points are $P_1$ and $P_2$ shown in FIG. 25. As discussed above, it is assumed that endoscope 2502 lies on the z-axis 2518 of the 3D system of coordinates, with its tip at the origin. Consequently, the axis 2518 of endoscope 2502 can be described as 3D line defined by the following equation:

$$x=0; y=0 \quad (8)$$

Module 2608 configures the computer system 151 to determine the axis 2514 of instrument 2506, which includes a 3D line defined by the following equation, in relation to points $P_1(x_1, y_1, z_1)$ and $P_2(x_2, y_2, z_2)$:

$$\frac{x-x_1}{x_2-x_1} = \frac{y-y_1}{y_2-y_1} = \frac{z-z_1}{z_2-z_1} \quad (9)$$

where Eq. (9) defines any point (x, y, z) on the axis 2514 of the instrument 2506.

Module 2610 configures the computer system 151 to compute transformations that virtually "move" endoscope 2502 to the pose of the instrument 2506. This "move" includes a series of virtual rotations and virtual translations that virtually align the z-axis 2518 of the endoscope 2502 with the axis 2514 of the target instrument 2506.

FIGS. 27A-27C are illustrative drawings representing virtual orientation transformations (FIG. 27A), virtual location transformation (FIG. 27B), and a resulting virtual alignment (FIG. 27C) in accordance with some embodiments. Such transformations are known to a person of skill in the art, and their implementation details can vary, including the sequence, number, or magnitude of such transformation. Also, persons of ordinary skill in the art will understand that different 3D systems of coordinates, other than Cartesian, can be used. For example, polar, parametric, or spherical system of coordinates can be employed without changing the results.

Referring to FIG. 27A, for example, segment $l_1$ represents a pose of the endoscope 2502, and segment $l_2$ represents a pose of the target instrument 2506. More particularly, segment $l_2$ represents position and orientation of the endoscope axis 2518, and segment $l_2$ represents position and orientation of the target instrument axis 2514. Module 2610 configures the computer 151 to virtually rotate segment $l_1$ around the x-axis by employing a rotation matrix $M_x$ defined by rotation angle $\alpha$. Module 2610 configures the computer 151 to then virtually rotate segment $l_1$ around the y-axis by employing a rotation matrix $M_y$ defined by rotation angle $\beta$. Lastly, if needed, module 2610 configures the computer 151 to virtually rotate segment $l_1$ around the z-axis by employing a rotation matrix $M$ defined by rotation angle $\gamma$. The use of rotation matrices is well known to persons skilled in the art and need not be described in detail herein.

As illustrated in FIG. 27B, the objective and result of these virtual rotations, in accordance with some embodiments, are such that the transformed segment $l_1'$ is now parallel to segment $l_2$, the axis 2514 of instrument 2506. The resulting overall rotation matrix M equals:

$$M = M_x \cdot M_y \cdot M_z \quad (10)$$

or, in trigonometric format:

$$M = \begin{bmatrix} \cos\alpha\cos\beta & \cos\gamma\sin\alpha + \sin\gamma\sin\beta\cos\alpha & \sin\gamma\sin\alpha - \cos\gamma\sin\beta\cos\alpha \\ -\cos\alpha\cos\beta & \cos\gamma\cos\alpha - \sin\gamma\sin\beta\cos\alpha & \sin\gamma\cos\alpha + \cos\gamma\sin\beta\cos\alpha \\ \sin\beta & -\sin\gamma\cos\beta & \cos\gamma\cos\beta \end{bmatrix} \quad (11)$$

Module 2610 further configures the computer 151 to determine a virtual position translation $T_v$ to move segment $l_1'$ to an overlapping position relationship with segment $l_2$, to which it is parallel. The geometric position translation is defined by a vector $\bar{v}$, shown in FIG. 27B. Vector $\bar{v}$ is defined by the tips of segments $l_1'$ and $l_2$, and it is oriented to point from $l_1''$ to $l_2$.

As shown in FIG. 27C, the resulting parallel segment $l_1''$ is virtually moved to a position in which it is overlapping $l_2$. Geometric translations are well known to persons skilled in the art and need not be described in detail herein.

In accordance with some embodiments, a virtual view of the Q3D model of scene 2508 from the viewing perspective of the tip 2516 of instrument 2506 is produced by transforming the Q3D model according to operations $T_v$, $M_z$, $M_y$, and $M_x$ described above, but in a reverse order. Module 2612 configures the computer 151 to first transform the Q3D model by applying a location translation of vector $-\bar{v}$. Module 2612 configures the computer 151 to perform a sequence of orientation rotations $M_z$, $M_y$, and $M_x$, of respective angles $-\gamma$, $-\beta$, and $-\alpha$, respectively.

Module 2614 configures the computer 151 to use the transformed Q3D model to display the surgical scene from the virtual perspective of the target instrument 2506. Based on distance $d_2$, the virtual perspective is created using a known perspective drawing algorithm. FIGS. 28A-28B are example Q3D views of the surgical scene 2508 from a perspective of the endoscope tip 2512 (FIG. 28A) and from a perspective of the target surgical instrument 2516 (FIG. 28B), in accordance with some embodiments. It will be appreciated that the surgical scenes of FIGS. 28A-28B can be made visible to a surgeon through a viewer 312, as described above with reference to FIG. 4, during a surgical procedure. Moreover, in accordance with some embodiments, the surgeon can selectively change the virtual perspective. From the endoscope perspective of FIG. 28A, the target instrument 2506 is visible together with the first (spherical) anatomical structure 2508-1 and the second (triangular) anatomical structure 2508-2. From the target instrument perspective of FIG. 28B, the first (spherical) anatomical structure 2508-1 and the second (triangular) anatomical structure 2508-2 are visible, but from a perspective different from that of FIG. 28A. The perspective illustrated in FIG. 28B can be generated using algorithm 2600 from FIG. 26.

FIG. 29 is an illustrative drawing showing details of a process to produce a 3D rendering of the Q3D model in accordance with some embodiments. Once the transformed Q3D model has be computed, it can be displayed on the 3D display 110 of the system. A number of 3D video algorithms and hardware implementations can be used for this purpose. The computer Module 2902 configures the system of FIG. 8, which comprises the video processor 104, controller 106, and display driver 109 to separate the Q3D model into a right-eye view 2904R and left-eye view 2004L, given an average human interpupillary distance (IPD) of 62-65 mm. To achieve this step, known details of stereoscopy and human IPD are applied. In accordance with some embodiments, module 2906 configures the 3D video controller 106 of 3D display driver 109 to alternately switch between providing video frames to the left eye 2908L and providing frames to the right eye 2908R at known frame rates in order to give the viewer the impression of a 3D scene. The approach described in FIG. 29 employs 3D viewing goggles, such as those present on a teleoperated surgery system, such as that described with reference to FIGS. 4-6. However, other 3D video display mechanism can be used. U.S. Pat. No. 4,562,463 (filed May 15, 1981) issued to Lipton and U.S. Pat. No. 6,008,839 (filed Nov. 27, 1995) issued to Nagele et al., provide additional implementation details, which are incorporated herein in their entirety by this reference.

No Fly Zone (NFZ)

FIGS. 30A-30B are illustrative drawings showing a perspective view of an endoscope 2502 associated with an image sensor array 210 having an endoscope field of view ($FOV_e$). Also shown are portions of a first surgical instrument 3024 associated with a no fly zone 3022, a second surgical instrument 3026, and an anatomical structure 3007 disposed in a surgical scene 3008 within the $FOV_e$, in accordance with some embodiments. A light source 2510 illuminates the surgical scene 3008. As explained with reference to FIGS. 7A-7B and FIGS. 8-10, an image sensor array 210 is positioned to capture image projections of the surgical instrument 2506 and the anatomical structure 3007 within the $FOV_e$ that illuminate a tip portion 2512 of the endoscope 2502. Although the image sensor array 210 is shown disposed adjacent the endoscope tip 2512, it will be appreciated that alternatively, the image sensor array can be displaced from the tip 2512 as explained with reference to FIG. 7B, for example. As explained above with reference to FIG. 8, the endoscope 2502 is positioned to penetrate body wall tissue or to enter a natural orifice and extend within a patient's body cavity in order to provide visual access to the surgical scene 3008 that includes, as example targets, the first and second surgical instruments 3024, 3026 and the anatomical structure 3007 inside the patient's body cavity. Additional explanation of some embodiments of the endoscope and its operation are provided above and will not be repeated.

FIGS. 30A-30B illustrate the field of view ($FOV_e$) of a Q3D endoscope 2502 deployed as described in reference to FIGS. 5-6 in accordance with some embodiments. As shown in FIGS. 5-6, instruments 101A-101B and a Q3D endoscope 101C may be deployed though different cannulas during a surgical intervention. It will be appreciated that the endoscope field of view ($FOV_e$) is visible to a surgeon through a viewer 312, as described above with reference to FIG. 4, during a surgical procedure. The NFZ region may appear in the scene in various ways, such as through numerical annotations showing a distance $d_{NFZ}$ or as a projected surface or "bubble" about instrument 3204, for example. The surgical intervention may involve use of a teleoperated medical system, or it may be manual minimally invasive intervention, or it may be an open surgery intervention, or a combination thereof. FIG. 6 illustrates placement of endoscope 101C and instruments 101A-101B on the mechanical surgical arms 158A-158D of a patient side cart, in reference to a teleoperated medical system surgical intervention. For clarity of presentation, a Q3D endoscope that comprises an image sensor array is discussed. However, the scope of the invention includes other types of Q3D endoscopes, such as those based on time-of-flight imaging sensors. U.S. Pat. No. 8,262,559 (the "559 Patent") describes such a Q3D endoscope, and it is incorporated herein by reference. The '559 Patent specification from column 8, line 45 to column 10, line 27 and corresponding Figures are incorporated herein by this reference.

An illustrative no fly zone (NFZ) represented by dashed lines 3022 is defined about the first instrument (Instrument A) 3024. The term "no fly zone" is used herein to refer to a region of space about a structure. In some embodiments, the NFZ is a region that is intended to be occupied solely by the object for which the NFZ is defined. In order to secure a patient's safety or the efficacy of the procedure, other instruments, such as instrument 3026 (Instrument B), or adjacent tissues are not desired to become located within the limits of the NFZ region. For example, if instrument 3024 is a Monopolar Curved Scissors (MCS), the NFZ region would be defined such that energy could not be inadvertently delivered from instrument 3024 to instrument 3026 or to adjacent tissue structures which are not targeted for therapy delivery. Sometimes, depending on the amount of moisture around an MCS, minor arcs or sparks may develop as energy is delivered to targeted tissues. Therefore, NFZ limits 3022 may be chosen to define a clearance of 1-2 mm or more around MCS instrument 3024. Hence, any arcs or sparks that may develop during energy delivery would not reach inadvertently to instrument 3026 or to other adjacent tissues. The NFZ limits may be selected automatically, by the system (for example, based on the type of instrument 3024 in use), or by the operator, according to the operator's knowledge about the procedure and about the instruments. The instruments may be indirectly (e.g., with computer assistance) or manually actuated. An NFZ changes location as the object for which it is defined changes location.

The example NFZ 3022 in FIGS. 30A-30B is defined as a space within a distance $d_{NFZ}$ from the first instrument 3024. In the scene in FIG. 30A, the distance between the first instrument (Instrument A) 3024 and the second instrument (Instrument B) 3026 is $d_{1A/B}$, which is greater than $d_{NFZ}$, and this condition indicates that the second instrument 3026 is outside the no fly zone of the first instrument 3024. In the scene in FIG. 30B, however, the distance between the first instrument (Instrument A) 3024 and the second instrument (Instrument B) 3026 is $d_{2A/B}$, which is less than $d_{NFZ}$, and this condition indicates that the second instrument 3026 is within the no fly zone of the first instrument 3024.

FIG. 31 is an illustrative flow diagram representing a process 3100 to define a no fly zone and to determine whether the no fly zone has been violated, in accordance with some embodiments. The process 3100 is described with reference to the surgical scene 3008 of FIGS. 30A-30B.

Module 3102 configures the computer 151 to identify a target in a Q3D scene for which an NFZ is to be created and to define respective NFZ regions based upon distance ($d_{NFZ}$), around one or more targets, which may include instruments and/or anatomical structures. In other words, an NFZ can be defined as a region within a distance of $d_{NFZ}$ from the target. Stated differently, the NFZ can be defined by a virtual bubble that surrounds the target at distance $d_{NFZ}$ from the target surface. For example, dashed lines 3022 in FIGS. 30A-30B indicate an NFZ around Instrument A 3024. In some embodiments, a user can manually indicate an object within a surgical scene that is to have an NFZ, and the user can manually enter $d_{NFZ}$ information. Referring to FIGS. 22A-22B, for example, a user may use a video marking tool, such as telestration, to identify a structure that is to have an NFZ. Alternatively, the system can define the NFZ based on characteristics of the instrument 3024, or of structure 3007, or use NFZ settings which are general or specific to the procedure if the system receives such information. It will be appreciated that although the example in FIGS. 30A-30B shows creation of an NFL for an instrument, alternatively, an NFZ can be created for an anatomical structure 3007. Also, although the example in FIGS. 30A-30B shows creation of a single NFZ, multiple NFZs can be created different NFZs for different instruments, or one NFZ for an instrument and another NFZ for an anatomical structure, for example.

Module 3104 configures the computer 151 to create a different Q3D model, Q3D-1, Q3D-2, and Q3D-3, for each of multiple corresponding changes in position of the first and second instruments 3024, 3026. The Q3D models are stored in a non-transitory storage device 3150.

Module 3106 configures the computer system 151 to identify the target instrument, e.g., the first instrument 2524 for which the NFZ region, defined based upon a ($d_{NFZ}$) distance defined about the target instrument, and each other instrument, e.g., instrument 3026, in each of the multiple different Q3D models. In some embodiments, instrument shape information is matched with Q3D model distance information to identify the target instrument. For example, the shape of the target instrument is stored in the non-transitory storage device. The stored shape of the instrument may be known from its computer-aided-design (CAD) model. Alternatively, the instrument may be previously scanned, and the resulting scans stitched so as to combine them to form a 3D shape model. A best match algorithm can be employed to detect the section of the Q3D model that best matches the stored shape of the target instrument. As previously described, best match algorithms use 2D or 3D correlation functions to compare the stored instrument shape with best match candidates extracted by traversing the Q3D model.

Module 3108 configures the computer system 151 to determine for each of the Q3D models whether the distance ($d_{A/B}$) between an instrument for which a $d_{NFZ}$ has been defined (e.g., Instrument A) and another instrument (e.g., Instrument B) is less than the $d_{NFZ}$ distance. In other words, assuming that a $d_{NFZ}$ is defined for Instrument A, a determination is made as to whether $d_{NFZ} >= d_{A/B}$.

Alternatively, for example, if an NFZ (not shown) is applied to anatomical structure 3007, module 3108 determines whether there has been a violation of that NFZ by one or both of Instrument A and Instrument B. For example, assume that the anatomical structure 3007 is a delicate blood vessel for which a $d_{NFZ}$ is defined. In that case, the respective NFZ limits would be used to prevent any instrument from getting too close and perforating the blood vessel. As a further alternative, for example, if anatomical structure 3007 is of lower clinical criticality (e.g., fat, bone, etc.), then some but not all instrument types may be prevented from entering the NFZ (e.g., sharp instruments, energy delivery instruments, etc.). And so, for an instrument of a first type and another instrument of a second type, the instrument types being identified to the surgical system in one or more various ways such as operator designation, machine vision, or direct sensing of instrument data, the instrument of the first type (e.g., a blunt dissection instrument) is permitted to enter the NFZ and the instrument of the second type (e.g., a cautery shears instrument) is not permitted to enter the NFZ. The determination of whether the NFZ limits were violated may be performed by direct comparison of $d_{NFZ}$ distances specified for different instruments and/or anatomical structures and the actual $d_{A/B}$ distances between them.

Referring again to the example scenes of FIGS. 30A-30B, a determination for the Q3D model created for the example scene of FIG. 30A would indicate that there has been no violation of the example NFZ 3022 defined for the first instrument 3024. But, a determination for the example scene of FIG. 30B would indicate that the NFZ 3022 has been breached by the second instrument 3026.

Module 3110 configures the computer 151 to provide an alert in response to a determination that the NFZ has been violated. The alarm may include a sound, a visual cue (such as a blinking light), or a locking or blocking or increased stiffness of instrument movement to avoid collision by using a haptic wall).

Projected Runway

FIG. 32 is an illustrative drawing showing an endoscope 2502 associated with an image sensor array 210 having an endoscope field of view ($FOV_e$). It will be appreciated that the endoscope field of view ($FOV_e$) is visible to a surgeon through a viewer 312, as described above with reference to FIG. 4, during a surgical procedure. Also shown is a portion of a surgical instrument 3206, observed at multiple different positions on an observed trajectory, and an anatomical structure 3207 disposed in a surgical scene 2508 within the $FOV_e$, in accordance with some embodiments. As explained more fully below, the same instrument 3206 is observed as it moves between multiple instrument positions 3206-p1, 3206-p2, and 3206-p3 so as to ascertain its trajectory, and the projected trajectory runway is extrapolated from that movement.

A light source 210 illuminates the surgical scene 2508. As explained with reference to FIGS. 7A-7B and FIGS. 8-10, an image sensor array 210 is positioned to capture image projections of the surgical instrument 3206 and the anatomical structure 3207 within the $FOV_e$ that illuminate an image sensor array 210 associated with a tip portion 2512 of the endoscope 2502. Although the image sensor array 210 is shown disposed adjacent the endoscope tip 2512, it will be appreciated that the image sensor array can alternatively be displaced from the tip 2512 as explained with reference to FIG. 7B, for example. As explained above with reference to FIG. 8, the endoscope 2502 is positioned to penetrate body wall tissue or a natural orifice and extend within a patient's body cavity in order to provide visual access to the surgical scene 2508 that includes, as example targets, the surgical instrument 3206 and the anatomical structure 3207 inside the patient's body cavity. Additional explanation of some embodiments of the endoscope and its operation are provided above and will not be repeated.

FIG. 32 illustrates the field of view $FOV_e$ of a Q3D endoscope 2601 deployed as described in reference to FIGS. 5-6, in accordance with some embodiments. As shown in FIGS. 5-6, instruments 101A-101B and Q3D endoscope 101C may be deployed though different cannulas during a surgical intervention. The surgical intervention may involve use of a teleoperated medical system, or it may be a manual minimally invasive intervention, or it may be an open surgery intervention, or a combination thereof. FIG. 6 illustrates placement of endoscope 101C and instruments 101A-101B on the mechanical surgical arms 158A-158D of a patient side cart, in reference to a teleoperated medical system surgical intervention.

For illustration purposes, a target surgical instrument 3206 is shown having an end effector in the form of a needle driver, such as the Mega Needle Driver ENDOWRIST® Instrument for the DA VINCI Si® Surgical System. Alternate end effectors, such as a stapler, vessel sealer, scissors, grasper, scalpel, cautery electrode, or clip applier, can be used to implement different surgical instrument functions during surgical interventions. In the illustrative scene 3208, the same target instrument 3206 changes position along an observed trajectory, also referred to as a path, from position 3206-p1 to position 3206-p2 to position 3206-p3. The dashed lines 3216 between positions 3206-p1, 3206-p2, and 3206-p3 represent the path followed by the instrument as it moves closer and closer to the anatomical structure 3207. During a medical intervention for example, a surgeon may cause the target instrument to follow the observed path 3216 that changes target instrument position from position 3206-p1 to position 3206-p2 to position 3206-p3, for example. It will be appreciated that in practice, some surgeons have difficulty precisely aligning a surgical instrument with an anatomical structure that is to be contacted using the instrument. For example, a surgeon may need to align a linear stapler with a tissue structure, such as the bowel, that is to be stapled together using the device. Proper alignment of the stapler and the bowel tissue prior to firing the stapler is critical, for example. Surgeons sometimes have difficulty envisioning how the instrument will be aligned once they insert the instrument into a region where it is to be used. For example, a surgeon may have difficulty envisioning the position and orientation of a stapler end effector as it is inserted into a resectioned bowel to perform an anastomosis. In accordance with some embodiments, a highly visible virtual projection that indicates a predicted path of the instrument path is provided within a surgeon's field of view. The surgeon can use the predicted path to perceive in advance how the instrument is aligned relative to an anatomical structure and how to best manipulate the instrument to get it into a desired position and orientation. For example, the surgeon can perceive in advance whether a stapler is in a proper alignment to create a staple line for anastomosis.

A predicted path, also referred to as a "runway", indicated by dashed line 3218 extends from the end of the observed path 3216. The predicted path may extend up to a predicted contact location 3220 (marked "X") on a surface of the anatomical object where the instrument 3206 is predicted to first contact the anatomical object. The predicted path 3218 and the predicted contact location 3220 are determined based upon the observed path 3216. More particularly, the image sensor array 210 is used to observe, i.e., produce a Q3D model of, the target instrument 3206 at each of a sequence of multiple positions, e.g., 3206-$p1$, 3206-$p2$, and 3206-$p3$, as an operator causes the instrument to move closer to the anatomical object 3207. Based upon that sequence of positions, determined at a sequence of points in time, the observed path 3216 is determined and based upon the observed path, the predicted path is determined. For example, the predicted path may be a linear extrapolation of the observed path. Alternatively, the predicted path may be a curved line that estimates the trajectory of certain parts of the target instrument. For example, if the target instrument is a Monopolar Curved Scissors or a HARMONIC ACE® Curved Shears instrument, the curved line may predict the trajectory of the curved blades. The predicted contact location 3220 is determined based upon the predicted path 3218. For example, the geometrical intersection between the predicted path 3218 and the surface of the Q3D model representing the target anatomical structure 3207 defines the predicted contact location 3220.

FIG. 33 is an illustrative flow diagram representing a process 2600 to track a target instrument on an observed path in a Q3D scene and to determine a predicted path and predicted contact location in accordance with some embodiments. The process 2600 is described with reference to the surgical scene 3208.

Module 3302 configures the computer 151 to create a different Q3D model for each of multiple corresponding changes in position of the target instrument 3206. The number of positions and corresponding models may be two or more. For example, as shown along the observed trajectory from 3206-$p1$ to 3206-$p2$ to 3206-$p3$, corresponding different Q3D models Q3D-1, Q3D-2, and Q3D-3 are created. The Q3D models are stored in a non-transitory storage device 3350. Alternatively, when the predicted path is just an extension of certain features of the target instrument, a single Q3D model is created and saved in the non-transitory storage device.

Module 3304 configures the computer system 151 to identify the target instrument in each of the multiple different Q3D models. In some embodiments, target instrument shape information is matched with Q3D model distance information to identify the target instrument. For example, the shape of the target instrument is stored in the non-transitory storage device. The stored shape of the instrument may be known from its computer-aided-design (CAD) model. Alternatively, the instrument may be previously scanned and the resulting scans stitched to form a 3D shape model. A best match algorithm can be employed to detect the section of the Q3D mode that best matches the stored shape of the target instrument. As previously described, best match algorithms use 2D or 3D correlation functions to compare the stored instrument shape with best match candidates extracted by traversing the Q3D model.

Module 3306 configures the computer 151 to determine a predicted path of a target instrument.

Module 3308 configures the computer 151 to produce a 3D visual representation of the scene that includes a visual indication of the predicted contact location 3220 on the anatomical structure 3206. The predicted path acts as a virtual geometric extension of the current path or current position of a target instrument. A surgeon may experiment with several different target instrument paths and/or deployment orientations, for example, before causing the target instrument to actually make physical contact with an anatomical structure. In accordance with some embodiments, a surgeon's changing the position of the target instrument results in module 3302 creating different Q3D models of a scene that correspond to the different positions or orientations. Modules 3306 and 3308, in turn, ascertain and display different predicted paths or extensions of the target instrument for different Q3D scene or series of Q3D scenes. The surgeon can use the visually displayed path information to determine the path or positioning of the target instrument that is most likely to result in its intersection with an anatomical structure at a desired location. Hence, the surgeon will be able to optimize the path and/or orientation of the target instrument so as to achieve a desired clinical goal.

More particularly, in some embodiments, a predicted path is determined based upon extrapolation of an observed path of the target instrument. The observed path may be observed over the course of multiple Q3D scenes. Referring to FIG. 32, for example, module 3306 configures the computer 151 to determine the predicted path 3218 of a target instrument based upon the observed path 3216 of the target instrument 3206. In accordance with some embodiments, the observed path is determined based upon the changes in position of a target instrument of the location of the instrument, e.g., from position 3206-$p1$, followed by 3206-$p2$, followed by 3206-$p3$, from one Q3D model to the next, e.g., from Q3D-1 to Q3D-2 and from Q3D-2 to Q3D-3. For example, at least one point or region of located on the target instrument is determined. In the case of a needle driver instrument, for example, this point may represent the tip of the instrument. The location of this point or region is sequentially determined in models Q3D-1, Q3D-2 and Q3D-3. A trajectory is constructed based on a best fit curve. For example, a least square error algorithm can be employed to generate a best fit linear trajectory passing through the sequential locations of the target instrument. This trajectory is then extrapolated to determine the predicted path, 3218, of the instrument. Thus, the predicted path 3218 is determined based upon the observed path 3216. In particular, the predicted path 3218 is determined by extrapolation from the observed path 3216.

Alternatively, in some embodiments, a predicted path is determined based upon module 3307 determining a geometrical extension of features of interest of a stationary target instrument. Thus, rather than observing changes in position of a target instrument over the course of multiple Q3D scenes to determine a predicted path of the target instrument, a predicted path is determined based upon the Q3D observation of the orientation of a stationary target instrument in conjunction with an extrapolation of the target contour into the scene based upon its observed orientation. In FIG. 36, for example, the target instrument is a stapler, and the predicted path represents an extension of the staple lines or an extension of a stapler knife channel. By observing a 3D representation of the Q3D extension, or the estimated "runway" of these features, the surgeon may obtain a much more accurate and quantitative understanding of where the staples and/or the knife cut will eventually be placed. For example, the 3D representation may assist the surgeon in properly aligning and advancing the stapler instrument with reference to an anatomical body when performing various surgical procedures, such as aligning with the bowel to perform an anastomosis. In addition, the quantitative aspect of these Q3D instrument runways allows the surgeon to measure, if needed, features of the predicted path (e.g., clearance between estimated knife cut line and adjacent tissues). Further, assuming that the predicted path 3218 intersects with the anatomical object 3207, a determination can be made as to the intersection location 3220. As described above, location 3220 may be computed as the geometrical intersection between the curve representing the predicted path 3218 and the surface of the Q3D model representing the target anatomical structure 3207. As explained above with reference to FIGS. 22A-22B, for example, the visual image representation of a Q3D contact location 3220 model can include a displayed visual marker that is associated with a target shown in a visual 3D video representation of the scene 2508.

Referring to FIG. 34, there is shown an example 3D visual representation of the scene 3208 in which the target instrument 3206 is assumed to be in the third position 3206-p3 shown in FIG. 32, and a predicted contact location marked in the image with a visual marker "CL" on the anatomical structure 3207 in accordance with some embodiments. It will be appreciated that an endoscope field of view is visible to a surgeon through a viewer 312, as described above with reference to FIG. 4, during a surgical procedure. The marker "CL" is provided based upon the predicted path 3218 of FIG. 32. Thus, a visual representation of the predicted contact location 3220 of an instrument 3206 with an anatomical structure 3207 can be produced based upon multiple observed Q3D positions of the instrument before, an operator can more readily guide the instrument 3206 to make contact with the anatomical structure at a desired contact location.

Although contact location 3220 is discussed in detail herein, other characteristics derived from the predicted path 3218 are equally important. As already mentioned above, it may be important to display the estimated stapler staple line (i.e., the lines along which surgical staples are applied) and/or cut line (i.e., the tissue separation resulting from driving a stapler knife between staple lines). For Monopolar Curved Scissors or HARMONIC ACE® Curved Shears, it is important to display the distance from the predicted path 3218 to adjacent tissues. These instruments, or others, deliver energy to tissue for therapeutic purposes. To minimize unintended tissue damage, it is important to help operators understand how far the tissues not targeted for therapy delivery are from the predicted path.

FIG. 35 is an illustrative drawing representing an example surgical scene 2508 in which an operator has attempted multiple different observed paths 3516-1 to 3516-3, and the process 3300 has produced corresponding predicted paths 3518-1 to 3518-3 and contact locations CL1 to CL3, plus a desired contact location "Y", in accordance with some embodiments. The surgical scene 2508 includes a portion of the endoscope 2502 and the anatomical structure 3507. It will be appreciated that an endoscope field of view is visible to a surgeon through a viewer 312, as described above with reference to FIG. 4, during a surgical procedure. Numerous details explained with reference to other drawings herein are omitted from the FIG. 35 in order to simplify the explanation.

A system operator, such as a surgeon, may use a trial-and-error technique to determine an optimal path to cause a target instrument 3506 follow to ensure that the instrument 3506 contacts the anatomical structure 3507 at a desired contact location "Y". In doing so, the operator may move the instrument along multiple different observed paths in sequence. The process 3300 of FIG. 33 produces a predicted contact location marker on a visual image of the anatomical structure for each observed path. The operator can use the contact location marker information to decide which path to use to make contact with the desired contact location "Y".

More particularly, for example, solid line arrow 3516-1, dashed line arrow 3518-1, and contact location marker CL1 represent a first observed path of instrument, a first predicted path of instrument, and a first predicted contact location of the target instrument 3506, respectively. Similarly, solid line arrow 3516-2, dashed line arrow 3518-2, and contact location marker CL2 represent a second observed path of instrument 3206, a second predicted path of instrument 3506, and a second predicted contact location of instrument 3506, respectively. Likewise, solid line arrow 3516-3, dashed line arrow 3518-3, and contact location marker CL3 represent a third observed path of instrument 3506, a third predicted path of instrument 3506, and a third predicted contact location of instrument 3506, respectively. It is noted that none of the observed paths 3516-1, 3516-2, and 3516-3 tried by the operator results in the instrument 3506 contacting the anatomical structure 3507 in the desired location "Y". Accordingly, in accordance with some embodiments, the operator can try yet another predicted path (not shown).

This trial-and-error technique may be similarly employed when a characteristic of interest, e.g., a shape of the instrument or a portion of the instrument, is geometrically (virtually) extended to determine the predicted paths 3518-1, 3518-2, and 3518-3, as displayed in 3D as illustrated in FIG. 35, for example.

It will be appreciated that different paths can be used to position a tool at different positions relative to a tissue structure so that energy, such as a laser burst, can be applied to the tissue at different locations and from different distances from the tissue, for example.

FIG. 36 illustrates an example where a predicted path image 3618, also referred to as a Q3D runway, represents a visible geometrical virtual extension of an instrument feature based upon the current location and orientation of the instrument. The example target instrument is a stapler instrument 3620, which is shown in a position and orientation before closing onto anatomical tissue and firing staples. Surgeons may spend time maneuvering the stapler around in order to understand where it will land during deployment. The dashed line images illustrate an extension of a staple line feature of the example stapler that includes six staple lines. The virtual extension image 3618 includes an image indicating the physical space occupied by the example stapler 3620 if its shape is extended by some distance given its current position and orientation. Given that the Q3D endoscope can be used to produce a model that includes the 3D dimensions and orientation of the stapler and of the target tissue, the predicted path of the staple lines that extends beyond the actual current location of the stapler and towards the target tissue (e.g. a colorectal structure in FIG. 36) can be determined. It will be appreciated that an endoscope field of view is visible to a surgeon through a viewer 312, as described above with reference to FIG. 4, during a surgical procedure. Therefore, a surgeon can simulate several stapler deployment orientations before the stapler even touches the target tissue. This way, the surgeon can understand more precisely where on the target tissue the stapler cartridge and anvil will land when clamped on target tissue for stapling and resection. Hence, the surgeon will be able to optimize the orientation of the staple line and that of the staple knife trajectory to achieve the desired therapeutic goal.

Instrument Tracking in Q3D Space

FIG. 37 is an illustrative drawing showing an endoscope 2502 associated with an image sensor array 210 having an endoscope field of view ($FOV_e$). FIG. 37 also shows a portion of the same surgical instrument, shown at multiple different positions 3706-$p1$, 3706-$p2$, 3706-$p3$, and an anatomical structure 3707 disposed in a surgical scene 3708 within the $FOV_e$, in accordance with some embodiments. It will be appreciated that the endoscope field of view is visible to a surgeon through a viewer 312, as described above with reference to FIG. 4, during a surgical procedure. A light source 2510 illuminates the surgical scene 3708. As explained with reference to FIGS. 7A-7B and FIGS. 8-10, an image sensor array 210 is positioned to capture image projections of the surgical instrument 3706 and the anatomical structure 3707 within the $FOV_e$ that illuminate a sensory array 210 associated with a tip portion 2512 of the endoscope 2502. Although the image sensor array 210 is shown disposed adjacent the endoscope tip 2512, it will be appreciated that alternatively, the image sensor array can be displaced from the tip 2512 as explained with reference to FIG. 7B, for example. As explained above with reference to FIG. 8, the endoscope 2502 is positioned to penetrate body wall tissue (e.g., via a cannula) or to enter a natural orifice and extend within a patient's body cavity in order to provide visual access to the surgical scene 3708 that includes, as example targets, the surgical instrument 3706 and the anatomical structure 3707 inside the patient's body cavity. Additional explanation of some embodiments of the endoscope and its operation are provided above and will not be repeated.

FIG. 37 illustrates the field of view ($FOV_e$) of a Q3D endoscope 2502 deployed as described in reference to FIGS. 5-6 in accordance with some embodiments. As shown in FIGS. 5-6, instruments 101A-101B and a Q3D endoscope 101C may be deployed though different cannulas during a surgical intervention. As mentioned above, alternatively, the endoscope and one or more instruments may also pass through a single opening—a single incision or natural orifice—to reach a surgical site. Thus, the use of a cannula is not mandatory. The surgical intervention may involve use of a teleoperated medical system, or it may be a manual minimally invasive intervention, or it may be an open surgery, intervention, or a combination thereof. FIG. 6 illustrates placement of endoscope 101C and instruments 101A-101B on the mechanical surgical arms 158A-158D of a patient side cart, in reference to a teleoperated medical system surgical intervention.

For illustration purposes, a target surgical instrument 3706 is shown having an end effector in the form of a needle driver, such as the Mega Needle Driver for the DA VINCI Si® Surgical System. However, alternate end effectors, such as scissors, grasper, scalpel, cautery electrode, or clip applier, can be used to implement different surgical instrument functions during surgical interventions. In the illustrative scene 3708, the same target instrument 3706 changes position, as indicated by the dashed line arrows, from its position 3706-$p1$ to its position 3706-$p2$ and then to its position 3706-$p3$. During a medical intervention for example, a surgeon may cause the target instrument to move from position 3706-$p1$ to position 3706-$p2$ and then to position 3706-$p3$, for example.

FIGS. 38A-38C are illustrative drawings representing changes in position of the target instrument from a position 3706-$p1$ at a first point in time (FIG. 38A) to a position 3706-$p2$ at a second point in time (FIG. 38B) and then to a position 3706-$p3$ at a third point in time (FIG. 38C), in accordance with some embodiments. Referring to FIG. 4, in accordance with some embodiments, a surgeon can view video frames of images of a surgical site inside a patient's body through a stereo display device 164, which includes the viewer 312. At the first point in time, the surgeon views the scene shown in FIG. 38A. At the second point in time, the surgeon views the scene shown in FIG. 38B. At the third point in time, the surgeon views the scene shown in FIG. 38C. From time to time in the course of a surgical procedure, the instrument 3706 can become obscured by blood, for example, and the surgeon may momentarily have difficulty distinguishing the target instrument 3706 from the surrounding tissue structure of the anatomical object 3707.

FIG. 39 is an illustrative flow diagram representing a process 2700 to track a target instrument by using a Q3D system in accordance with some embodiments. The process 3900 shall be described with reference to the surgical scene 3708.

Module 3902 configures the computer 151 to create a different Q3D model, Q3D-1. Q3D-2, and Q3D-3, for each of multiple corresponding changes in position of the target instrument 3706, from 3706-$p1$ to 3706-$p2$ to 3706-$p3$. Alternatively, the first Q3D model may be updated with incremental information related to the changing locations of instrument 3706. The Q3D models, or the respective incremental updates, are stored in a non-transitory storage device 3950.

Module 3904 configures the computer system 151 to identify the target instrument in each of the multiple different Q3D models. In some embodiments, target instrument shape information is matched with Q3D model distance information to identify the target instrument. For example, the shape of the target instrument is stored in the non-transitory storage device 3950. The stored shape of the instrument may be known from its computer-aided-design. (CAD) model. Alternatively, the instrument may be previously scanned and the resulting scans stitched to form a 3D shape model. A best match algorithm can be employed to detect the section of the Q3D mode that best matches the stored shape of the target instrument. As previously described, best match algorithms use 2D or 3D correlation functions to compare the stored instrument shape with best match candidates extracted by traversing the Q3D model.

Module 3906 configures the computer system 151 to produce a visual representation of each of the Q3D models that each includes a visual indication of the target instrument 3706. As explained above with reference to FIGS. 22A-22B, for example, the visual image representation of a Q3D model can include a visual marker displayed associated with a target shown in a visual 3D video representation of the scene 3708.

Referring to FIG. 40, there is shown an example visual representation of the scene 3708 in which the target instrument 3706, in the second position 3706-$p2$, is shown associated with a visual marker "M2", in accordance with some embodiments. It will be appreciated that the endoscope field of view ($FOV_e$) is visible to a surgeon through a viewer 312, as described above with reference to FIG. 4, during a surgical procedure. The visual image of the target instrument 3706 is partially obscured from view by body fluids, 4002 such as blood, for example. Nevertheless, the marker "M2", provided based upon the Q3D-2 model, indicates the location of the target instrument 3706 at position 3706-p2. Thus, multiple Q3D visual representations can be produced to show the target instrument location at different times, which permits an operator to track the target instrument within the scene 3708 even if the instrument becomes obscured from view by body fluids, for example.

Alternatively, a visual marker in the form of contoured features that are raised or recessed in a known pattern can be employed. For example, an instrument may be embossed with a pattern that a Q3D endoscope can recognize. The pattern may be embossed so as to provide an indication of the orientation of the instrument that it is embossed upon. By capturing information indicative of the contour pattern, a Q3D model can be generated that indicates the position and orientation of the instrument even if it is visually obscured by fluids such as blood, for example.

The foregoing description and drawings of embodiments in accordance with the present invention are merely illustrative of the principles of the invention, Therefore, it will be understood that various modifications can be made to the embodiments by those skilled in the art without departing from the spirit and scope of the invention, which is defined in the appended claims. Particularly, the systems and methods described above were presented in implementations that involved a Q3D endoscope which comprised an image sensor array. However, the scope of the invention includes other types of Q3D endoscopes, such as those based on nine-of-flight imaging sensors. Those skilled in the art would know how to substitute Q3D endoscope 2502 with others.

The invention claimed is:

1. A system for visualizing three dimensional images of an anatomical structure from a viewpoint of a target instrument, comprising:
    a quantitative three-dimensional (Q3D) endoscope disposed to image a scene within a field of view of the Q3D endoscope; and
    at least one processor configured to:
        determine a Q3D model of the scene imaged by the Q3D endoscope;
        identify at least one target instrument within the scene and a 3D pose of the at least one target instrument;
        identify at least one tissue structure within the scene;
        determine a geometric transformation from the field of view of the endoscope to a virtual field of view of said at least one target instrument, the geometric transformation comprising orientation and position transformations to transform the Q3D model to take on the 3D pose of the at least one target instrument and to align a z-axis of the Q3D endoscope along a longitudinal axis of the least one target instrument; and
        produce, based at least in part upon said geometric transformation, a three-dimensional (3D) view of said at least one tissue structure within the Q3D model as represented from the virtual field of view of said at least one target instrument.

2. The system of claim 1, wherein the system comprises a 3D display that displays said 3D view.

3. The system of claim 1, wherein the system comprises a viewer to display quantitative measurements based upon, at least in part, said 3D view.

4. The system of claim 1, wherein the system comprises a control input device for a user to select said at least one instrument from a set of instruments.

5. The system of claim 1, wherein determining a geometric transformation from the field of view of the endoscope to the virtual field of view of said at least one instrument includes:
    determining a geometric orientation of the Q3D endoscope;
    determining a geometric orientation of at least one instrument;
    determining one or more geometric transformations so as to move the Q3D endoscope
    into a virtually overlapping position with the at least one instrument and so as to align the Q3D endoscope with the determined orientation of the at least one instrument.

6. The system of claim 1, wherein the 3D pose comprises at least a portion of the least one target instrument in at least one translation degree of freedom and orientation of at least the portion of the least one target instrument in at least rotational degree of freedom.

7. The system of claim 1, wherein the geometric transformation uses one of a following coordinate system: Cartesian, polar, cylindrical and spherical.

8. The system of claim 1, wherein the geometric transformation is configured to virtually move the Q3D endoscope within the scene to take on the 3D pose of the least one target instrument.

9. A system for maneuvering a surgical instrument, comprising:
    a quantitative three-dimensional (Q3D) endoscope disposed to image a scene within its field of view;
    at least one processor configured to:
        determine a Q3D model of the scene imaged by the Q3D endoscope;
        identify an anatomical structure as a first target within the scene;
        identify a surgical instrument as second target within the scene;
        determine, based at least on a type of the surgical instrument and one or more characteristics of at least one of the first or second targets, a Q3D no fly zone associated with at least one of the first or second targets; and
        determine whether a distance between the first target and the second target is within the no fly zone.

10. The system of claim 9, wherein the processor is configured to determine whether said Q3D no fly zone has been violated, based at least in part upon the Q3D model; and provide an output signal in response to a determination that Q3D no fly zone was violated.

11. The system of claim 9, wherein the determination whether the Q3D no fly zone has been violated is based at least in part on a closest distance between the first and second targets that is less than a threshold distance.

12. The system claim 9, wherein the processor produces an alert in response to, at least in part, said output signal.

13. The system claim 12, wherein the alert can be one of the following: visual, video, audio, haptic, graphic, or textual.

14. The system of claim 9,
    wherein the first target includes a surgical instrument;
    wherein the no fly zone associated with the first target; and wherein the processor is configured to determine whether a distance between the first target and the second target is small enough that the second target is within the no fly zone.

15. The system of claim 9, wherein the Q3D no fly zone comprises a region to be occupied solely by the at least one of the first or second targets associated with the Q3D no fly zone.

16. The system of claim 9, wherein the at least one processor is further configured to select one or more limits of the Q3D no fly zone based at least on the type of surgical instrument.

17. The system of claim 9, wherein the at least one processor is further configured to determine the Q3D no fly zone based at least on a shape of the surgical instrument.

18. The system of claim 9, wherein the at least one processor is further configured to identify the type of surgical instrument based on designation by an operator of the surgical instrument.

* * * * *